(12) United States Patent
Harper et al.

(10) Patent No.: US 12,090,340 B2
(45) Date of Patent: Sep. 17, 2024

(54) FLASH DOSE RADIOTHERAPY SYSTEMS AND METHODS

(71) Applicant: RefleXion Medical, Inc., Hayward, CA (US)

(72) Inventors: Brent Harper, New Glarus, WI (US); David Quentin Larkin, Menlo Park, CA (US); Peter Demetri Olcott, Los Gatos, CA (US); George Andrew Zdasiuk, Portola Valley, CA (US); David Nett, Danville, CA (US); Victor Carboni, San Mateo, CA (US)

(73) Assignee: RefleXion Medical, Inc., Hayward, CA (US)

( * ) Notice: Subject to any disclaimer, the term of this patent is extended or adjusted under 35 U.S.C. 154(b) by 167 days.

(21) Appl. No.: 17/696,662

(22) Filed: Mar. 16, 2022

(65) Prior Publication Data
US 2022/0305292 A1    Sep. 29, 2022

Related U.S. Application Data

(63) Continuation of application No. PCT/US2020/052036, filed on Sep. 22, 2020.
(Continued)

(51) Int. Cl.
*A61N 5/10* (2006.01)
*H05H 9/00* (2006.01)

(52) U.S. Cl.
CPC ......... *A61N 5/1048* (2013.01); *A61N 5/1045* (2013.01); *A61N 5/1081* (2013.01);
(Continued)

(58) Field of Classification Search
None
See application file for complete search history.

(56) References Cited

U.S. PATENT DOCUMENTS

| 3,794,840 A | 2/1974 | Scott |
| 7,902,530 B1 | 3/2011 | Sahadevan |

(Continued)

FOREIGN PATENT DOCUMENTS

| WO | WO-2018/093933 A1 | 5/2018 |
| WO | WO-2018/093937 A1 | 5/2018 |
| WO | WO-2019/032911 A1 | 2/2019 |

OTHER PUBLICATIONS

International Search Report mailed on Feb. 4, 2021, for PCT Application No. PCT/US2020/052036, filed on Sep. 22, 2020, 4 pages.
(Continued)

*Primary Examiner* — Marcus H Taningco
(74) *Attorney, Agent, or Firm* — Cooley LLP

(57) ABSTRACT

Disclosed herein are systems and methods for rapidly delivering high doses of radiation, also known as, flash dose radiotherapy or flash radiotherapy. One variation of a system for flash radiotherapy has a plurality of therapeutic radiation sources on a support structure (e.g., a gantry or arm) and configured to toward a patient target region, and a controller in communication with all of the therapeutic radiation sources. The controller is configured to activate the plurality of therapeutic radiation sources simultaneously so that the patient target region rapidly receives a high dose of radiation, e.g. the entire prescribed dose of radiation. In some variations, a flash radiotherapy system has a pulsed, high-power source that may be used to generate an X-ray pulse that delivers a dose having a dose rate from about 7.5 Gy/s to about 70 Gy/s. Flash radiotherapy systems may also include one or more imaging systems mounted on the support structure.

19 Claims, 31 Drawing Sheets

Related U.S. Application Data

(60) Provisional application No. 62/905,644, filed on Sep. 25, 2019.

(52) U.S. Cl.
CPC .............. *A61N 5/1083* (2013.01); *H05H 9/00* (2013.01); *H05H 2277/11* (2013.01)

(56) References Cited

U.S. PATENT DOCUMENTS

| | | | |
|---|---|---|---|
| 8,618,521 | B2 | 12/2013 | Loo et al. |
| 9,931,522 | B2 | 4/2018 | Bharadwaj et al. |
| 10,500,416 | B2 | 12/2019 | Larkin et al. |
| 2010/0027744 | A1 | 2/2010 | Brown et al. |
| 2011/0201919 | A1* | 8/2011 | Allen ................... A61N 5/1045 600/411 |
| 2016/0193481 | A1 | 7/2016 | Tantawi et al. |
| 2018/0133518 | A1* | 5/2018 | Harper ................. A61N 5/1049 |
| 2018/0161600 | A1 | 6/2018 | Bowman et al. |
| 2019/0022409 | A1 | 1/2019 | Vanderstraten et al. |
| 2019/0022411 | A1 | 1/2019 | Parry et al. |
| 2019/0069856 | A1* | 3/2019 | Achkire ................ A61B 6/0487 |
| 2020/0368557 | A1* | 11/2020 | Harper .................. A61N 5/1049 |

OTHER PUBLICATIONS

Maenchen, J. et al. (1999). "Inductive voltage adder driven X-ray sources for hydrodynamic radiography," Digest of Technical Papers. 12th IEEE International Pulsed Power Conference. (Cat. No. 99CH36358), vol. 1, pp. 279-282.

Montay-Gruel, P. et al. (Sep. 2017). "Irradiation in a flash: Unique sparing of memory in mice after whole brain irradiation with dose rates above 100 Gy/s," Radiother. Oncol. 124:365-369.

Smith, I.D. (Jun. 2004). "Induction voltage adders and the induction accelerator family," Phys. Rev. ST Accel. Beams 7:064801, 41 total pages.

Written Opinion of the International Searching Authority mailed on Feb. 4, 2021, for PCT Application No. PCT/US2020/052036, filed on Sep. 22, 2020, 8 pages.

\* cited by examiner

402

LTspice netlist                                                                               Page 1

```
* Run name:Marx with IVA 3A
* Description: Marx/waterlines/IVA/diode

* Marx 10 stages open circuit output voltage 960kv (96kv per stage, 80%
+ of rating, 120kv rated)
CM 0 1 67n
LM 1 2 1250n
RM 2 3 3
CIS 3 0 25n
*CPFL 4 0 30n; 6 each 25nsec 1 way waterlines at 5 ohms 5nf each
RP 7 0 .83
LSPFL 3 3a 500n

*water line 50 nsec FWHM
TWL1 4 0 5 0 Z0=.83 Td=25n
TWL2 6 0 7 0 Z0=0.83 Td=125n

*Load
Swlswo 3a 4 9 0 SMOD2
.MODEL SMOD2 SW (RON=0.01 ROFF= 1E+06)
V2 9 0 PWL (0,0V 420n, 0V 420.5n, .33V 420.8n, .66V 421n, 1V)

Swlswo1 5 6 11 0 SMOD3
.MODEL SMOD3 SW (RON=0.01 ROFF= 1E+06)
V3 11 0 PWL (0,0V 675n, 0V 675.5n, .33V 680n, .66V 680.5n, 1V)

.tran 0 5u 0.1n UIC
.ic v(1) -960kv
*.ic v(2) 0
*.ic v(3) 0
*.ic v(4) 0
.END
```

FIG. 4D

Marx/water line/diode

504

```
*Run name:Tline with Marx driver with diode varying 4A
*Description: Marx/waterline/output switch/diode

*Marx 30 stages charged to 2.5MV (83kV per stage)
Cp    0 1 14.6n ; 4 parallel .22u @ 50kV
Lp    1 2 3.6u
Rp    2 3 12
Rfiller 3 6 .01|

*Water line 45 nsec FWHM
TWL 6 0 7 0 Z0=6 Td=22.5n

*Load
Swlswo 7 8 9 0 SMOD2
.MODEL SMOD2 SW (RON=.01 ROFF=1E+06)
V2 9 0 PWL(0, 0V 302.5n, 0V 303n, .33V 303.5n, .66V 304n,1V)

Swlswo1 8 0 11 0 SMOD3
.MODEL SMOD3 SW (RON=100 ROFF=1E+04)
V3 11 0 PWL(0, 0V 304n, 0V 304.5n, .33V 305n, .66V 306n,1V)

Swlswo2 8 0 12 0 SMOD4
.MODEL SMOD4 SW (RON=.01 ROFF=1E+06)
V4 12 0 PWL(0, 0V 351n, 0V 352n, .33V 353n, .66V 354n,1V)

.tran 0 20u 0 .1n UIC
.ic V(1) -2.50MegV
.END
```

FIG. 5C

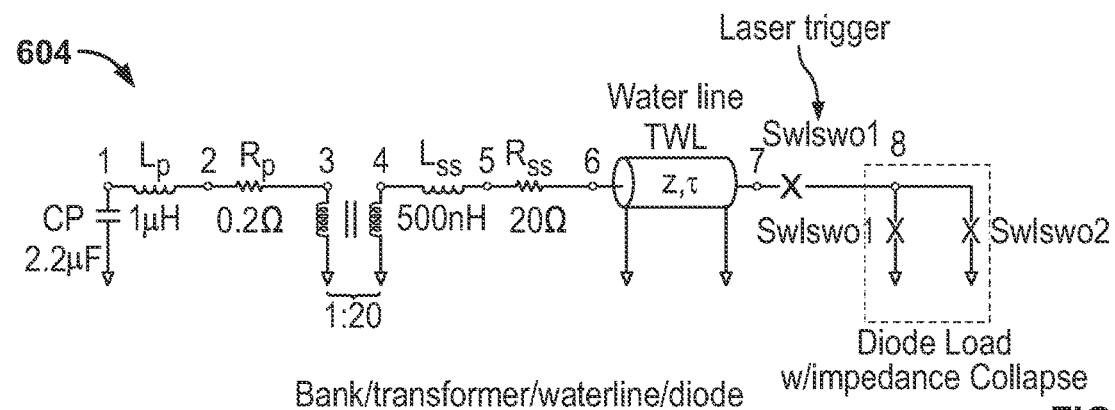

FIG. 6C

Bank/transformer/waterline/diode

606 ⟶

*Run name: Tline with transformer with diode varying 3A
*Description: Capacitor bank/transformer/waterline/output switch/diode

*Capacitor bank
Cp  0  1  2.2u
LP  1  2  1u
Rp  2  3  .2

*Transformer 1:20
Ltp  3  0  50u
Lts  4  0  20000u
K  Ltp  Lts  0.99999

*Secondary output circuit elements
Lss  4  5  500n
Rss  5  6  20

*Water line 45 nsec FWHM
TWL  6  0  7  0  Z0=6  Td=22.5n

*Load
Swlswo  7  8  9  0  SMOD2
.MODEL  SMOD2  SW (RON=.01 ROFF=1E+06)
V2  9  0  PWL(0, 0V  3024n, 0V  3024.3n, .33V  3024.6n, .66V  3025n, 1V)

Swlswo1  8  0  11  0  SMOD3
.MODEL  SMOD3  SW (RON=100 ROFF=1E+04)
V3  11  0  PWL(0, 0V  3025n, 0V  3025.5n, .33V  3026n, .66V  3027n, 1V)

Swlswo2  8  0  12  0  SMOD4
.MODEL  SMOD4  SW (RON=.01 ROFF=1E+06)
V4  12  0  PWL(0, 0V  3067n, 0V  3067.5n, .33V  3068n, .66V  3068.5n, 1V)

.tran 0 20u 0 .1n UIC
.ic V(1) -170kV
.END

FIG. 6D

FLASH DOSE RADIOTHERAPY SYSTEMS AND METHODS

CROSS-REFERENCE TO RELATED APPLICATIONS

This application is a continuation of International Patent Application No. PCT/US2020/052036, filed on Sep. 22, 2020, which claims priority to U.S. Provisional Patent Application No. 62/905,644, filed on Sep. 25, 2019, the disclosure of each of which is hereby incorporated by reference in its entirety.

BACKGROUND

Radiation therapy involves delivering a prescribed dose of radiation to a tumor (e.g., lesion) with the goal of reducing the dose delivered to healthy tissue adjacent to the tumor. In some radiation therapy systems, a radiation source mounted on a gantry moves or rotates around a patient on a table or couch, and directs radiation toward the patient's tumor(s). As the radiation source rotates around the patient, the patient table or couch may be moved in a direction that is parallel to the axis of rotation of the radiation source. In this manner, radiation may be applied to the patient's tumor(s) from various gantry angles and at various patient table or couch positions, based on images of the patient and the tumor(s) generated by various imaging modalities in advance of the treatment session.

Conventional systems are unable to achieve sufficient dose rates for delivering an entire prescribed dose over a short period of time (e.g., about 10 seconds or less, about 5 seconds or less, a breath hold). For example, conventional linear accelerators (e.g., linacs) are incapable of delivering a full dose in a single breath hold. As an illustrative example, assume a breath hold is about ten seconds. Eight seconds of that time may be used for patient/tumor imaging and verification, and the remaining two seconds may be allocated for dose delivery. Then, for a prescription dose of 10 Gy and a modulation factor of 1.5, a dose rate of about 450 Gy/min or about 7.5 Gy/sec is required. In contrast, a conventional 6 MV linac is capable of generating a dose rate of about 15 Gy/min or about 0.25 Gy/sec.

Since conventional radiation therapy systems have limited dose delivery rates, a patient may be required to receive a series of radiation pulses over time periods that may last several minutes over multiple sessions and/or fractions in order for the patient to receive a prescribed dose. For example, a prescribed dose may be delivered to a patient as three fractions of 15 gray (Gy) each up to about thirty fractions of 2 Gy each. Within these fractions, patient motion during and after pulse delivery may create uncertainty about the amount and location of dose delivery. For example, one or more of patient breathing, gross patient movement, system calibration, changes in patient anatomy between sessions, and exposure of healthy tissue to non-specific/scatter radiation may all increase the risk of irradiating and/or damaging healthy tissue. Accordingly, additional systems and methods for radiation therapy may be desirable.

SUMMARY

Disclosed herein are systems and methods for rapidly delivering high doses of radiation, also known as, flash dose radiotherapy or flash radiotherapy. Systems for flash radiotherapy may comprise a plurality of therapeutic radiation sources that are arranged or oriented on a support structure (e.g., gantry, robotic arm, gimbal) such that they are directed toward a patient target region and a controller in communication with all of the therapeutic radiation sources. The controller may be configured to activate the plurality of therapeutic radiation sources simultaneously and/or in rapid succession so that the patient target region rapidly receives a high dose of radiation, for example, the entire prescribed dose of radiation. Alternatively, or additionally, a system for flash radiotherapy may comprise a therapeutic radiation source that is configured to emit a high dose of radiation in a brief period of time. In one variation, a flash radiotherapy system may comprise a pulsed, high-power source that may be used to generate an X-ray pulse that delivers a dose having a dose rate from about 7.5 Gy/s to about 70 Gy/s. In some variations, a therapeutic radiation source for flash radiotherapy may comprise a pulsed, high-power source having an inductive voltage adder that generates an electron beam, and an X-ray converter target that converts the energy from the electron beam into a photon (e.g., X-ray) beam pulse that delivers radiation dose at a rate from about 7.5 Gy/s to about 70 Gy/s. Flash radiotherapy systems may also comprise one or more imaging systems mounted on a support structure (e.g., the same or different support structure as the therapeutic radiation source(s)). The field-of-view of an imaging system may include a region where the radiation beams generated by the therapeutic radiation sources converge or intersect, e.g., the system isocenter. The imaging system may be used to confirm the location of the target region before the delivery of a high dose of radiation. Flash radiotherapy systems may be configured to deliver the entire prescribed dose of a target region in a single pulse or in a series of pulses over about 10 seconds or less, such as within a single breath hold of the patient.

One variation of a flash radiotherapy system may comprise a support structure, an imaging system mounted on the support structure, a therapeutic radiation source mounted on the support structure, wherein the therapeutic radiation source is powered by a pulsed high-power source and is configured to generate an X-ray beam pulse that delivers radiation at a dose rate from about 7.5 Gy/s to about 70 Gy/s, and a beam-shaping assembly disposed over the therapeutic radiation source and in a path of the X-ray beam pulse. The therapeutic radiation source may be configured to generate an X-ray beam pulse that delivers dose value from about 1 Gy to about 200 Gy, e.g., about 60 Gy. The X-ray beam pulse may have a duration of about 200 ns or less, e.g., about 40 ns to about 50 ns. The X-ray beam pulse may have a pulse energy of at least about 1 MeV. The support structure may be rotatable or may be stationary. In some variations, the high-power source may comprise an inductive voltage adder (IVA) that generates an electron beam, and the therapeutic radiation source may further comprise an X-ray converter target that converts the electron beam into the X-ray beam pulse. The IVA may be configured to generate X-ray beam pulses having an energy of about 2 MV. The IVA may comprise an energy storage capacitor or capacitor bank. The high-power source may comprise a Marx generator configured to supply power to the IVA. The system may further comprise a high-voltage insulant disposed between the Marx generator and the IVA, and in some variations, the insulant may comprise a water cable and/or an oil-filled coaxial cable. The Marx generator may be configured to generate a pulse having an amplitude of about 500 kV and a pulse width (FWHM) of about 50 ns. The high-power source may comprise a plurality of serially-arranged Marx generators that are configured to discharge synchronously to supply power to the IVA. In some variations of a flash radiotherapy system, the beam-shaping assembly may comprise a dynamic multi-leaf collimator having a plurality of movable leaves. Alternatively, or additionally, a beam-shaping assembly may comprise a variable circular collimator. The therapeutic radiation source may be a first therapeutic radiation source and the system may further comprise a second therapeutic radiation source. The support structure may comprise a gantry, and/or a robotic arm, and/or a gimbal.

A radiotherapy system for rapidly delivering high doses of radiation (also known as a flash radiotherapy system) may comprise multiple non-coplanar therapeutic radiation sources. One variation of a flash radiation therapy system may comprise a gantry, a first therapeutic radiation source mounted on the gantry and having a first radiation beam axis, a second therapeutic radiation source having a second radiation beam axis and mounted on the gantry such that the second radiation beam axis is oriented at an angle with respect to the first radiation beam axis, and an imaging system mounted on the gantry between the first and second therapeutic radiation sources. The imaging system may have a field-of-view having an imaging central axis, and the first radiation beam axis, the second radiation beam axis, and the imaging central axis may intersect at a system isocenter. The system may comprise a controller in communication with the first therapeutic radiation source, the second therapeutic radiation source, and the imaging system, and the controller may be configured to activate the first and second therapeutic radiation sources simultaneously to deliver an entire prescribed radiation dose in one pulse. The gantry may define a bore with a longitudinal axis that intersects the system isocenter. The first therapeutic radiation source may be located at a first longitudinal position along the bore, the second therapeutic radiation source may be located at a second longitudinal position along the bore, and the imaging system may be located at a third longitudinal position between the first and second longitudinal positions. The gantry may be a circular gantry. The bore may have a first diameter at the first longitudinal position, a second diameter at the second longitudinal position, and a third diameter at the third longitudinal position, where the third diameter may be less than or equal to the first and/or second diameters. The first therapeutic radiation source may be located at a first circumferential position about the circular gantry, the second therapeutic radiation source may be located at a second circumferential position about the circular gantry. The imaging system may be located at a third circumferential location about the circular gantry. In some variations, the first circumferential location is the same as the second circumferential location. The third circumferential location may be the same as the first and second circumferential locations. The field-of-view of the imaging system may define an imaging plane, and the mounting locations of the first and second therapeutic radiation sources may not be coplanar with the imaging plane. In some variations, the gantry may comprise three concentric rings including a first ring, a second ring, and third ring between the first and second rings. The first therapeutic radiation source may be mounted on the first ring, the imaging system may be mounted on the third ring, and the second therapeutic radiation source may be mounted on the second ring.

The first therapeutic radiation source may comprise a first linear accelerator (linac), the second therapeutic radiation source may comprise a second linac that is thermally tuned to the first linac, and the system may further comprise a RF source that supplies radio frequency power to the first and second linacs. The system may comprise a first electron gun configured to provide electrons to the first linac, and a second electron gun configured to provide electrons to the second linac. A first beam-shaping assembly may be disposed over the first therapeutic radiation source along the first radiation beam axis, and a second beam-shaping assembly may be disposed over the second therapeutic radiation source along the second radiation beam axis. The first and second beam shaping-assemblies may each comprise a dynamic multi-leaf collimator. In some variations, the dynamic multi-leaf collimator may be a two-dimensional multi-leaf collimator or a binary multi-leaf collimator. For example, the two-dimensional multi-leaf collimator may be a variable circular collimator, such as an iris collimator. The system may optionally comprise a first MV detector mounted on the gantry opposite the first therapeutic radiation source, and a second MV detector mounted on the gantry opposite the second therapeutic radiation source. The imaging system may be an imaging system selected from the list consisting of a MRI imaging system, kVCT imaging system, PET imaging system, CT/PET imaging system, and MVCT imaging system. The first and second therapeutic radiation sources may be configured to emit radiation beams having an energy of at least about 1 MV. The first and second therapeutic radiation sources may be configured to emit radiation beams having an energy of about 6 MV or more, e.g., about 9 MV. Alternatively, or additionally, one or more the therapeutic radiation sources may be configured to emit radiation beams having an energy of about 1 MV, about 2 MV, about 3 MV, about 4 MV, or more.

A flash radiotherapy system may comprise arrays of therapeutic radiation sources on multiple gantries. For example, a flash radiation therapy system may comprise a gantry, an imaging system mounted on the gantry, wherein the imaging system has a field-of-view with an imaging central axis, a first array of therapeutic radiation sources each having a radiation beam axis and where the radiation beam axes of each of the therapeutic radiation sources in the first array are oriented toward a first focal point within the field-of-view, and a second array of therapeutic radiation sources each having a radiation beam axis and where the radiation beam axes of each of the therapeutic radiation sources in the second array are oriented toward a second focal point within the field-of-view. The imaging system may be located between the first and second arrays of therapeutic radiation sources. The imaging central axis, the first focal point, and the second focal point intersect at a system isocenter. The gantry may comprise three concentric rings including a first ring, a second ring, and third ring between the first and second rings. The first array of therapeutic radiation sources may be mounted on the first ring, the imaging system may be mounted on the second ring, and the second array of therapeutic radiation sources may be mounted on the third ring. Each of the radiation beam axes of the first array of therapeutic radiation sources may be at a non-zero angle relative to the imaging central axis, and each of the radiation beam axes in the second array of therapeutic radiation sources may be at a non-zero angle relative to the imaging central axis. The non-zero angle may be from about 10° to about 60°. The system may further comprises a MV detector corresponding to each of the therapeutic radiation sources in the first array of therapeutic radiation sources and may be located across its corresponding therapeutic radiation source. In some variations, the system may further comprise a MV detector corresponding to each of the therapeutic radiation sources in the second array of therapeutic radiation sources and may be located across its corresponding therapeutic radiation source. The imaging system may be an imaging system selected from the list consisting of an MRI imaging system, kVCT imaging system, PET imaging system, CT/PET imaging system, and MVCT imaging system. The field-of-view of the imaging system may define an imaging plane, and the first and second arrays of therapeutic radiation sources may not be coplanar with the imaging plane. The gantry may define a bore with a longitudinal axis that intersects the system isocenter, and the first array of therapeutic radiation sources may be located at a first longitudinal position along the bore, the second array of therapeutic radiation sources may be located at a second longitudinal position along the bore, and the imaging system may be located at a third longitudinal position between the first and second longitudinal positions. The bore may have a first diameter at the first longitudinal position, a second diameter at the second longitudinal position, and a third diameter at the third longitudinal position, where the third diameter may be less than or equal to the first and/or second diameters. The first array of therapeutic radiation sources may comprise a first array of linear accelerators (linacs) that are thermally tuned to each other, the second array of therapeutic radiation sources may comprise a second array of linacs that are thermally tuned to each other, and the system may further comprise a first RF source that supplies radio frequency power to the first array of linacs and a second RF source that supplies radio frequency power to the second array of linacs. A system may further comprise a first electron gun configured to provide electrons to the first array of linacs, and a second electron gun configured to provide electrons to the second array of linacs. A flash radiotherapy system may comprise a plurality of beam-shaping assemblies, where each beam-shaping assembly may be disposed over each therapeutic radiation source of the first and second arrays of therapeutic radiation sources and within a beam path of each therapeutic radiation source. Each beam shaping-assembly may comprise a dynamic multi-leaf collimator, such as a two-dimensional multi-leaf collimator or a binary multi-leaf collimator. The two-dimensional multi-leaf collimator may be a variable circular collimator, for example, an iris collimator. In some variations, the gantry may be a circular gantry. A flash radiotherapy system may further comprise a controller in communication with the first array of therapeutic radiation sources, the second array of therapeutic radiation sources, and the imaging system. The controller may be configured to activate the first and second arrays of therapeutic radiation sources simultaneously to deliver an entire prescribed radiation dose in one pulse.

A flash radiotherapy system may comprise a pulsed high-power source. One variation of a flash radiotherapy system may comprise a gantry, a therapeutic radiation source mounted on the gantry, the therapeutic radiation source comprising an inductive voltage adder (IVA) and an X-ray converter target, and a multi-leaf collimator disposed over the therapeutic radiation source and in a path of an X-ray beam pulse from the therapeutic radiation source. The IVA may be configured to generate an electron beam pulse and the X-ray converter target may be disposed in a path of the electron beam pulse such that when the electron beam pulse strikes the converter target, an X-ray beam pulse is generated. The X-ray beam pulse may have a duration of about 200 ns or less, e.g., from about 40 ns to about 50 ns. The X-ray beam pulse may deliver a dose value from about 1 Gy to about 200 Gy, e.g., the dose value may be about 60 Gy. The X-ray beam pulse may have a pulse energy of at least about 1 MeV, e.g., about 3 MeV. The gantry may be rotatable or not rotatable. In some variations, the therapeutic radiation source may be a first therapeutic radiation source and the system further comprises a second therapeutic radiation source. The IVA may be configured to generate X-ray beam pulses having an energy of about 1 MeV or 2 MeV. The therapeutic radiation source may further comprise a Marx generator configured to supply power to the IVA. Optionally, the system may comprise a high-voltage insulant disposed between the Marx generator and the IVA. The high-voltage insulant may comprise a water cable and/or an oil-filled coaxial cable. The IVA may comprise an energy storage capacitor or capacitor bank. Alternatively, or additionally, the IVA may comprise three or more serially-arranged stages, where each stage comprises a voltage source, a current loop, and a switch. The therapeutic radiation source may further comprise a Marx generator configured to supply power to each voltage source in the three or more stages of the IVA. The switch may be a laser-triggered switch and the system may further comprise a controller in communication with the Marx generator and a plurality of lasers. Each laser may correspond to a laser-triggered switch of each IVA stage, and the controller may be configured to serially activate the lasers to serially close the laser-triggered switches of each stage of the IVA. The Marx generator may be configured to generate a pulse having an amplitude of about 500 kV and a pulse width (FWHM) of about 50 ns. The multi-leaf collimator may be a dynamic multi-leaf collimator having a plurality of movable leaves. The system may optionally comprise a movable patient platform, where a pitch, roll, and/or yaw configuration of the patient platform may be adjustable. The therapeutic radiation source may further comprise a plurality of serially-arranged Marx generators that are configured to discharge synchronously to supply power to the IVA. The therapeutic radiation source may further comprise three or more Marx generators configured to supply power to each corresponding voltage source in the three or more stages of the IVA.

A method of flash dose delivery may comprise generating a first indicator to a patient on a platform of a radiotherapy system to pause breathing motion after an inhale, acquiring imaging data of the patient while breathing is paused, combining acquired imaging data with treatment planning imaging data to calculate a patient position offset, adjusting a treatment plan radiation delivery parameter according to the calculated patient position offset, generating a second indicator to the patient to pause breathing after an inhale, and emitting a radiation pulse to the patient in accordance with the adjusted treatment plan radiation delivery parameter while breathing is paused. The first indicator and the second indicator may comprise one or more indicators selected from the list consisting of: a visual indicator, an audio indicator, a tactile indicator. A method may further comprise determining whether the patient position offset exceeds a pre-determined threshold value and generating a third indicator if the patient position offset exceeds the pre-determined threshold value. Emitting a radiation pulse may comprise emitting radiation from a plurality of therapeutic radiation sources mounted on a gantry disposed around the platform. Alternatively, or additionally, emitting a radiation pulse may comprise delivering a dose from about 1 Gy to about 200 Gy in one pulse. The emitted radiation pulse may have a pulse energy of about 3 MeV.

A method of flash dose delivery may comprise confirming the position of a patient target region on a patient platform of a radiotherapy system, and activating the first and second therapeutic radiation sources simultaneously to generate a dose of radiation to the patient target region, wherein the dose has a dose rate from about 7.5 Gy/s to about 70 Gy/s.

The radiotherapy system may further comprise a support structure (e.g., gantry, arm, robotic arm, C-arm, gimbal) disposed about the patient platform, a first therapeutic radiation source, a second therapeutic radiation source, and an imaging system, wherein the first and second therapeutic radiation sources and the imaging system are mounted on the support structure. Activating the first and second therapeutic radiation sources may comprise generating a single pulse from each radiation source. Activating the first and second therapeutic radiation sources may comprise generating a plurality of pulses from each radiation source over about 10 seconds such that the cumulative dose rate is from about 7.5 Gy/s to about 70 Gy/s. Activating the first and second therapeutic radiation sources may comprise generating a plurality of pulses from each radiation source over about 2 seconds such that the cumulative dose rate is from about 7.5 Gy/s to about 70 Gy/s.

BRIEF DESCRIPTION OF THE DRAWINGS

FIG. 4D depicts a PSPICE netlist of the circuit model of FIG. 4C.

FIG. 5C depicts a PSPICE netlist for simulation that corresponds to the circuit model of FIG. 5B.

FIG. 6C depicts an equivalent circuit diagram or model of a high-dose therapeutic radiation source.

FIG. 6D depicts a PSPICE netlist for simulation that corresponds to the circuit model of FIG. 6C.

DETAILED DESCRIPTION

Figure 1A:
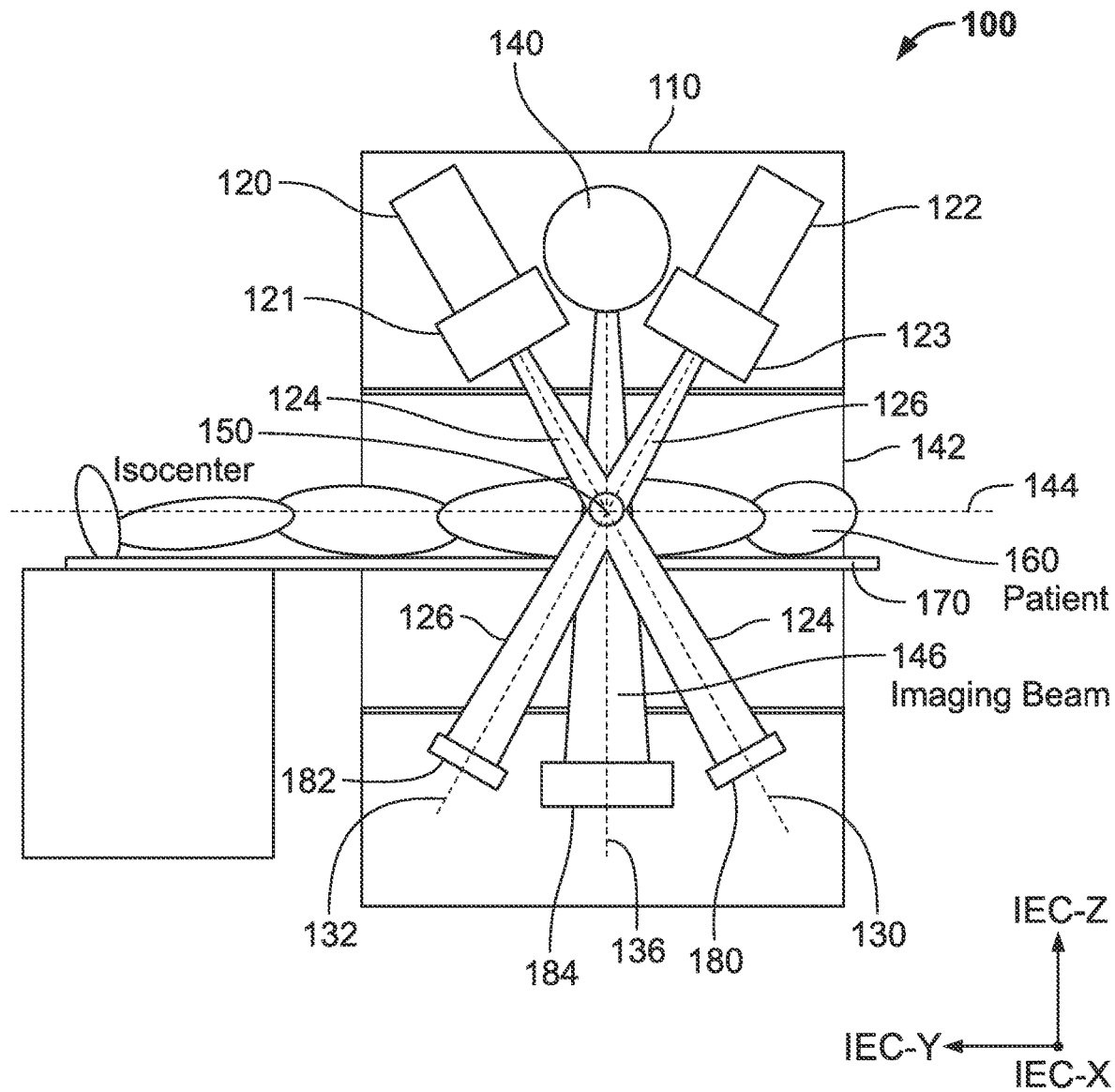
FIG. 1A depicts a schematic cross-sectional view of one variation of a system for flash radiotherapy.

Disclosed herein are systems and methods for flash radiotherapy. Systems for flash radiotherapy may comprise a plurality of therapeutic radiation sources that are arranged or oriented on a support structure such that they are directed toward a patient target region (which may be, in some variations, positioned at system isocenter) and a controller in communication with all of the therapeutic radiation sources. The controller may be configured to activate a plurality of therapeutic radiation sources simultaneously and/or in rapid succession so that the patient target region rapidly receives a high dose of radiation, for example, the entire prescribed dose of radiation for the patient target region. Alternatively or additionally, a system for flash radiotherapy may comprise a single therapeutic radiation source that is configured to emit a high dose of radiation in a brief period of time, for example, in a single pulse and/or several pulses in about 10 seconds or less (e.g., one patient breath hold). The one or more therapeutic radiation sources of a flash radiotherapy system may be able to deliver dose at a rate from about 7.5 Gy/s to about 70 Gy/s. The flash radiotherapy systems described herein may also comprise one or more beam-shaping devices disposed within the beam path of the one or more therapeutic radiation sources, and/or one or more MV detectors located opposite a corresponding therapeutic radiation source. Examples of beam-shaping devices may comprise one or more of jaws, collimators, multi-leaf collimators (e.g., binary and/or 2-D multi-leaf collimators), combinations thereof, and the like.

Also described herein are methods for flash radiotherapy. Methods for flash radiotherapy may comprise acquiring imaging data to confirm that a patient target region is located and/or oriented at the desired position relative to the therapeutic radiation source(s), e.g., confirm that the patient target region is located at the system isocenter. If the patient target region is not located at the desired location, a patient platform may be adjusted to change the position and/or orientation of the patient target region. Additional imaging data may be acquired to confirm that the adjusted position and/or orientation of the patient target region is at the desired position. The method may then comprise activating the one or more therapeutic radiation sources to emit radiation with a dose rate from about 7.5 Gy/s to about 70 Gy/s to the patient target region in a single pulse and/or a plurality of pulses in about 10 seconds or less. Optionally, some methods of flash radiotherapy may comprise providing one or more indicators or instructions to the patient to pause breathing when the therapeutic radiation sources have been activated (i.e., during the emission of therapeutic radiation pulses) and then to resume breathing after the therapeutic radiation sources have been deactivated (i.e., at the conclusion of the emission of therapeutic radiation pulses). The duration of the breath hold may be about 10 seconds or less, about 5 seconds or less, about 3 seconds or less, about 2 seconds or less, including all values and ranges in-between. Imaging data may be acquired after the patient inhales and used to calculate radiation delivery parameters (e.g., adjust the apertures of any beam-shaping devices, pulse duration, frequency, duty cycle, and/or power amplitude, etc.). After the radiation delivery parameters have been adjusted according to the calculated parameter values, the therapeutic radiation source(s) may then emit radiation to the patient target region while the patient is holding their breath in the inhaled position.

In some variations, the systems, devices, and methods disclosed herein may comprise one or more systems, devices, and methods described in International Patent Application Serial No. PCT/US2017/061848, filed on Nov. 15, 2017, the contents of which are hereby incorporated by reference in its entirety.

Delivering a large dose of radiation to a patient target region over a short period of time using any of the systems and methods described herein may provide some advantages over delivering smaller doses of radiation spaced out over a longer period of time. Since the high-dose radiation is delivered quickly, there is less time for patient motion and as a result, the treatment motion margins around a patient target region may be reduced.

Moreover, a dose is typically delivered at multiple angles to reduce skin dose and mitigate damage to healthy tissue. Accordingly, multiple breath holds and/or multiple beam pulses (e.g., beamlines) are typically required to deliver a prescribed dose. For example, up to fifteen beam pulses and up to fifteen breath holds may be required to deliver a full dose (e.g., 10 Gy) from a conventional 6 MV linac to a patient using a modulation factor of 1.5.

Conventional radiotherapy workflows involve significant setup time to image the patient and verify patient positioning and treatment parameters, which is repeated for a plurality of dose delivery cycles. For example, the patient is first grossly aligned to a patient platform (e.g., couch top) of a radiotherapy system. An imaging scan (e.g., scout scan) is performed to locate and position a patient target region relative to the radiotherapy system. A plurality of dose delivery cycles is then executed to deliver a prescribed dose to the patient. Each dose delivery cycle may include the steps of real-time imaging, treatment planning verification, and dose delivery while the patient holds their breath. For example, the patient may be instructed to perform a breath hold while acquiring a full CT imaging set of the patient target region (e.g., target volume). The acquired imaging set is fused (e.g., verified) with predetermined treatment planning images to calculate patient position offsets. The operator may review and then confirm/execute dose delivery. The patient may exhale after the dose is delivered and the cycle may be repeated until the prescribed dose is delivered. In some variations, the angle of dose delivery may be changed for different dose delivery cycles by tilting, yawing, and/or pitching the patient on the patient platform. The systems and methods for rapid delivery of high doses of radiation as described herein may simplify a radiotherapy workflow by reducing the number of dose delivery cycles and to thereby reduce treatment times, margins, and potentially improve patient outcomes.

I. Systems

Generally, the systems described herein may comprise a support structure a plurality of therapeutic radiation sources (e.g., MV X-ray source, array of sources, high-energy photon source, gamma source, electron beam, protons, etc.) mounted on the support structure, and an imaging system mounted on the support structure. In some variations, the support structure may be stationary (e.g., the therapeutic radiation sources and/or imaging system are in fixed positions) while in other variations, the support structure may be movable. A movable support structure may comprise a stationary component and a movable (e.g., translatable and/or rotatable and/or articulatable) component that is coupled to the stationary component. The therapeutic radiation source(s) and/or imaging system may be mounted on the movable component of the support structure. In some variations, a movable support structure may comprise a gantry, such as a circular gantry having a stationary frame and ring coupled to the frame. Alternatively or additionally the movable support structure may comprise a robotic arm and/or a gimbal and/or a C-arm, and the one or more therapeutic radiation sources and/or imaging system(s) may be mounted on the end of the robotic arm and/or gimbal and/or C-arm. The radiation therapy system may also comprise a corresponding radiation detector mounted on the support structure (e.g., on the movable component of the support structure) at a position opposite a respective therapeutic radiation source. The beams emitted from the plurality of therapeutic radiation sources may be shaped by one or more beam-shaping assemblies (e.g., one or more jaws, multi-leaf collimators, X-ray hardening filters, etc.). The movable support structure may define a bore or channel through the gantry where the bore includes a patient treatment area.

While some of the variations and examples of radiotherapy systems described herein comprise a gantry having a stationary frame and a rotatable ring coupled to the frame, it should be understood that the descriptions may apply to any radiotherapy systems that have a movable support structure having a stationary component (e.g., a stationary base) and a movable component (e.g., a robotic arm, one or more gimbal assemblies, etc.), and are not limited to radiotherapy systems with a gantry. For example, a radiotherapy system having multiple therapeutic radiation sources may comprise multiple arms, one for each of the therapeutic radiation sources, so that the position of each radiation source may be individually controlled. A radiotherapy system with a stationary support structure may include the features, elements, and functions described for gantry-based radiotherapy systems (e.g., at least the non-movable features, elements, and functions).

The radiation therapy systems described herein may also comprise a patient platform configured to move the patient into and out of the patient treatment area. The position of the patient platform within the bore or channel of the gantry, the position of the plurality of radiation sources (which may each be therapeutic radiation sources) around the patient treatment area (e.g., circumferential location of the radiation source around the gantry bore or channel) and the radiation beam pulses emitted from the radiation source may be synchronized by a controller such that a desired dose is delivered to a desired patient target region of the patient (e.g., tumor, lesion).

FIG. 1A depicts schematic cross-sectional side view of one variation of a radiation therapy system (100) comprising a rotatable gantry (110) and a patient platform (170) (e.g., couch top) configured to hold a patient (160) disposed on top of the patient platform (170). The patient platform (170) may be configured to move within a bore (142) of the gantry (110). The length of the bore (142) may define a central longitudinal axis (144). The longitudinal axis (144) of the bore may intersect a system isocenter (150) of the radiation therapy system, as described in more detail herein. The gantry (110) may be a circular gantry (e.g., ring gantry). In some variations, the gantry (110) may comprise one or more rings. The radiation therapy system (100) may comprise a first therapeutic radiation source (120) and a second therapeutic radiation source (122) each mounted on the gantry (110). A first beam-shaping assembly (121) may be located in a radiation beam path of the first therapeutic radiation source (120) and a second beam-shaping assembly (123) may be located in a radiation beam path of the second therapeutic radiation source (122). For example, the first beam-shaping assembly (121) may be disposed over the first therapeutic radiation source (120) along a first radiation beam axis (130), and the second beam-shaping assembly (123) may be disposed over the second therapeutic radiation source (122) along a second radiation beam axis (132).

The system (100) may further comprise an imaging system (140) mounted on the rotatable gantry (110) and an imaging detector (184) mounted on the gantry (110) opposite to the imaging system (140). The imaging system (140) may be configured to generate an imaging beam (146) having a field-of-view and a imaging central axis (136) that intersects the center of the field-of-view. The imaging beam (146) further defines an imaging plane that may be oriented, for example, along a transverse plane of the system (100) (e.g., a plane defined by IEC-Z and IEC-X axes). For example, the imaging plane within the imaging beam (146) may intersect (e.g., irradiate) a width-wise cross-section of the bore (142). In some variations, the system isocenter (150) may be defined as the intersection of the central longitudinal axis (144) and the imaging central axis (136) of the imaging field-of-view.

The first therapeutic radiation source (120) may be configured to emit a first radiation beam (124) defining a first radiation beam axis (130) and the second therapeutic radiation source (122) may be configured to emit a second radiation beam (126) defining a second radiation beam axis (132). The second radiation beam axis (132) may be oriented at an angle with respect to the first radiation beam axis (130). In some variations, the first and second therapeutic radiation sources may be positioned and configured such that the first radiation beam axis (130) and the second radiation beam axis (132) intersect at the system isocenter (150). For example, the first therapeutic radiation source (120), the second therapeutic radiation source (122), and the imaging system (140) may be positioned and/or configured such that the first and second radiation beams (124, 126) and the imaging beam (146) (e.g., imaging plane) intersect at the system isocenter (150).

A first detector (180) may be mounted on the gantry (110) opposite to the first therapeutic radiation source (120) and a second detector (182) may be mounted on the gantry (110) opposite to the second therapeutic radiation source (122). A detector may be provided to detect the collimated, high energy radiation of each radiation beam (124, 126). A detector (180, 182) provided for each therapeutic radiation source (120, 122) may improve one or more of imaging, system quality assurance, and real-time quality assurance performed by the system (100).

In some variations, one or more treatment planes may be defined by the intersection of the first and second radiation beams (124, 126) and imaging beam (146). In some variations, the patient (160) may be positioned on a patient platform (170) such that the patient target region (e.g., lesion) is located in the treatment plane and/or is located (e.g., overlapping) with the system isocenter (150). The imaging beam (146) may intersect the system isocenter (150) where a lesion of the patient (160) may be positioned. This allows the imaging system (140) to at least image the lesion and surrounding healthy tissue. The imaging system may be used to generate imaging data for use with registration, treatment planning, verification, and/or radiation delivery. For example, a lesion of the patient (160) may be positioned within the imaging plane and/or at system isocenter (150).

In some variations, the first and second radiation beams (124, 126) are not coplanar with the imaging beam (146). That is, the first and second radiation beam axis (130, 132) may be oriented at an angle with respect to the imaging central axis (136). This configuration allows the lesion positioned at system isocenter (150) to receive the first and second radiation beams (124, 126) from their respective beam delivery angles. In some variations, the first and second radiation beams (124, 126) may intersect at a system isocenter (150) to provide a spheroidal dose of radiation.

The radiotherapy system (100) may further comprise a controller (not shown) in communication with the first therapeutic radiation source (120), the second therapeutic radiation source (122), and the imaging system (140). For example, the controller may be configured to activate the first and second therapeutic radiation sources (120, 122) simultaneously to deliver up to an entire prescribed radiation dose in one pulse.

The imaging system (140) may be mounted on the gantry (110) between the first and second therapeutic radiation sources (120, 122). For example, the first and second therapeutic radiation sources (120, 122) and the imaging system (140) may be disposed along a longitudinal length of the gantry (110). For example, the first therapeutic radiation source (120) may be located at a first longitudinal position along the bore (142) and the second therapeutic source (122) may be located at a second longitudinal position along the bore (142). The imaging system (140) may be located at a third longitudinal position between the first and second longitudinal positions. Accordingly, the mounting locations of the first and second therapeutic radiation sources (120, 122) are not coplanar with the imaging plane (142).

As shown in FIG. 1A, each of the first and second therapeutic radiation sources (120, 122) and the imaging system (140) are disposed on a same side of the gantry (110). For example, the first therapeutic radiation source (120) may be located at a first circumferential position about the gantry (110) and the second therapeutic radiation source (122) may be located at a second circumferential position about the gantry (110). The imaging system (140) may be located at a third circumferential location about the gantry (110). As shown in FIG. 1A, the first circumferential location is the same as the second circumferential location. The third circumferential location is also the same as the first and second circumferential locations. Alternatively, one or more of the circumferential locations may be different from each other. In some variations, the imaging system (140) may be mounted to a side of the gantry (110) opposite to and between the first and second therapeutic radiation sources (120, 122) (see FIG. 1C).

Therapeutic Radiation Source and Radiofrequency (RF) Source

A therapeutic radiation source as used herein refers to a device configured to deliver a dose prescribed (e.g., tumorcidal dose) by a clinician to cause ablation (e.g., cell death) to a patient target region (e.g., tumor region, lesion, tissue). In some variations, a first therapeutic radiation source (120) comprises a first linear accelerator (linac) and a second therapeutic radiation source (122) comprises a second linac that may be thermally tuned to the first linac. In some variations, the first and second therapeutic radiation sources (120, 122) may be configured to emit first and second radiation beams (124, 126) each having an energy of at least about 6 MV. For example, the first and second radiation beams (124, 126) may each have an energy of about 9 MV or more. The dose delivered by a 9 MV beam may be more than double the dose delivered by a 6 MV beam. A higher dose delivery capability allows the system to deliver a prescribed dose using fewer therapeutic radiation sources and/or beams, and/or with fewer radiation pulses, thereby improving one or more of efficiency, cost, and availability of the system (100). Alternatively or additionally, one or more the therapeutic radiation sources may be configured to emit radiation beams having an energy less than about 6 MV (e.g., about 1 MV, about 2 MV, about 3 MV, about 4 MV, etc.) with a sufficient intensity level (e.g., flux) to deliver the prescribed dose. For example, a therapeutic radiation source may be configured to emit radiation beams having an energy of about 6 MV or more to deliver dose to tumors at deep locations and/or may be configured to emit radiation beams having an energy of about 3 MV or less (e.g., about 1 MV or less) to deliver dose to tumors at shallow or superficial locations (e.g., in a patient's skin, just below a patient's skin surface, etc.).

In some variations, the therapeutic radiation source may comprise a set of cold-cathodes configured to discharge stored electrical energy in a single pulse to an X-ray converter target for generating an X-ray beam. An X-ray converter target may be configured to receive high-energy electrons where the collision of the electrons with the high-density target generates high-energy photons (e.g., X-rays). For example, an energy storage bank may be configured to transmit energy to a plurality of cold-cathode heads. In some of these variations, an X-ray converter target damaged by high-energy cold-cathode pulses may be removed and replaced by the radiotherapy system while pumping down the vacuum of the cold-cathode.

In some variations, the first and second therapeutic radiation sources (120, 122) of the system (100) may comprise linear accelerators (linacs). The system (100) may comprise an RF source (not shown in FIGS. 1A-1D) configured to supply radio frequency power to the first and second therapeutic linacs (120, 122). Each linac may comprise an electron gun. The first linac (120) may comprise a first electron gun and the second linac (122) may comprise a second electron gun. The RF source may be configured to supply radio frequency power to accelerate electrons generated by the electron gun. The accelerated electrons may be directed to a heavy-metal target of a linac, and the collision of the electrons with the heavy-metal target (e.g., X-ray converter target, tungsten target) may generate high-energy photons or X-rays. In some variations, a single RF source may be used to accelerate the electrons from both electron guns or each therapeutic radiation source may have its own RF source. The intensity of the first and second radiation beams (124, 126) may be independently modulated using the respective first and second electron guns. For example, an electron gun may be configured to provide intensity modulation based on one or more of pulse width, gating pulses, combinations thereof, and the like. In some embodiments, an RF source and electron gun may be collectively configured to intensity modulate (e.g., gate) each radiation beam (124, 126).

The RF source and electron gun may be independently configured to modulate an intensity (e.g., dose, fluence) of a radiation beam emitted by the therapeutic radiation source. For example, the RF source and electron gun may be independently configured to control a pulse frequency of an emitted radiation beam. For example, each radiation beam may modulate the number of radiation pulses (e.g., dose, fluence) by one or more of gating the RF source, gating the electron gun, and offsetting the RF source and electron gun pulses.

In some variations, one or more RF sources may be coupled to one or more linacs of a radiotherapy system. RF sources coupled to a linac must output energy that dynamically matches the resonant frequency of the linac due to thermal drift. The resonant frequency of the linac may be controlled based on the temperature of the linac and a predetermined resonant frequency-to-temperature relationship. In some variations, a plurality of RF sources may be coupled to a plurality of linacs such that each therapeutic radiation source is dynamically coupled (e.g., interleaved) to one or more RF sources so as to match with the resonant frequency of the linac.

In some variations, a single RF source may be coupled to a plurality of linacs such that the output of the RF source matches the resonant frequencies of the plurality of linacs. For example, the plurality of linacs may be thermally matched to each other and to the single RF source in order to match the resonant frequencies of the plurality of linacs to the output of the single RF source. In particular, the plurality of linacs may first be thermally matched to each other using predetermined thermal mapping for each of the linacs. The output of the RF source may then be matched to the common resonant frequency of the plurality of linacs.

Beam-Shaping Assembly

Generally, a therapeutic radiation beam may be generated by a linac and shaped by a beam-shaping assembly. In some variations, the beam-shaping assembly may comprise one or more of a primary collimator, secondary collimator, multi-leaf collimator, first jaw, second jaw, X-ray hardening filter, combinations thereof, and the like. A primary collimator and/or secondary collimator may comprise a fixed beam-shaping aperture (e.g., shape and/or size of the aperture is constrained to a predetermined shape or size) or a variable beam-shaping aperture (e.g., shape and/or size of the aperture may be varied as desired before, and/or during, and/or after treatment). In some variations, the primary collimator may comprise a tungsten substrate or base with a trapezoidal-shaped slot that may define a general shape of the radiation beam. Similarly, the first jaw and/or second jaw may comprise a fixed beam-shaping aperture or a variable beam-shaping aperture. The collimators and/or jaws may shape the beam along two axes (e.g., x-axis and y-axis) or may shape the beam along one axis (e.g., x-axis only or y-axis only). The multi-leaf collimator may be configured to shape the beam along two axes (e.g., x-axis and y-axis), and/or may be configured to shape the beam along one axis (e.g., x-axis only or y-axis only). In some variations, an X-ray hardening filter may be configured to shape received X-rays and output a flattened X-ray beam (e.g., a beam with a substantially consistent fluence or energy level across the irradiation field). For example, the X-ray hardening filter may be composed of metal (e.g., tungsten, steel, lead, uranium, aluminum) and may have a conical shape. In some variations, a radiation therapy system may further comprise a target converter comprising a target and a primary collimator, a dose chamber, upper jaws, a multi-leaf collimator (MLC) (e.g., a binary MLC), and lower jaws. The primary collimator, upper jaws, the binary MLC, and lower jaws may shape the radiation beam emitted by the linac. The upper and lower jaws may move on curved rails that loosely focus to the virtual point spot of the target converter.

In some variations, the first beam-shaping assembly (121) comprises a first dynamic multi-leaf collimator and the second beam-shaping assembly (122) comprises a second dynamic multi-leaf collimator. In some variations, the dynamic multi-leaf collimator may be a two-dimensional multi-leaf collimator or a binary multi-leaf collimator. The two-dimensional multi-leaf collimator may be a variable circular collimator and optionally, an iris collimator. In some variations, an iris collimator may be configured to shape a beam with a circular cross-section useful for delivery to patients having multiple spherical lesions common in stage IV cancer. In some variations, a location of the therapeutic radiation source may be fixed relative to the gantry and a corresponding beam-shaping assembly may be gimbaled in one or two dimensions such that an emitted radiation beam may be configured to cover a larger portion of the imaging system field-of-view. In other variations, the gantry may be gimbaled while the locations of the therapeutic radiation source and beam-shaping assembly may be fixed relative to the gantry. Any of the radiation beam components and subsystems described herein may be gimbaled in one or two dimensions.

As described previously, radiation therapy systems may comprise a multi-leaf collimator disposed in the beam path of the therapeutic radiation source. In some variations, the multi-leaf collimator may be a binary multi-leaf collimator, such as any of the binary multi-leaf collimators described in U.S. patent application Ser. No. 15/179,823, filed Jun. 10, 2016, which is hereby incorporated by reference in its entirety. In one variation, the multi-leaf collimator may comprise a plurality of leaves and a corresponding number of pneumatic leaf actuation mechanisms. Each leaf actuation mechanism may be configured to independently move its corresponding leaf, and a air supply grid may be coupled to one or more of the pneumatic leaf actuation mechanisms. The compressed air supplied to each pneumatic leaf actuation mechanism is provided by an air supply grid that comprises separately and independently-controlled valves (i.e., first and second valves of a plurality of pneumatic leaf actuation mechanisms). The compressed air within the air supply grid may be provided by a compressor or compressed air source mounted on the gantry. Each of the pneumatic leaf actuation mechanisms may comprise a barrel comprising a longitudinal lumen, a first side opening, and a second side opening, and a piston that extends within the longitudinal lumen of the barrel. The piston may comprise a shaft and a piston seal coupled to the shaft within the barrel, where movement of the piston within the barrel translates the collimator leaf between the first location and the second location. The first and second openings may be fluidly connected to compressed air. The compressed air supplied to each pneumatic leaf actuation mechanism is provided by an air supply grid that comprises separately and independently-controlled valves (i.e., first and second valves of a plurality of pneumatic leaf actuation mechanisms). The compressed air within the air supply grid may be provided by a compressor or compressed air source mounted on a ring of the gantry. For example, the air supply grid may comprise a first valve disposed between the first opening and the compressor and a second valve disposed between the second opening and the compressor. The first and second valves of the air supply grid may selectively regulate fluid flow into and out of the barrel lumen. Compressed air may be distributed to each of the leaf pneumatic mechanism barrels (one for each leaf) via the air supply grid and/or an array of air conduits, where each valve of the air supply grid may be individually controlled to regulate the air flow into each barrel. Some variations of an on-board compressor system may comprise accumulator tanks, filters, dryers, and aftercoolers. Systems that comprise an optional kV radiation source for imaging and/or patient position registration may comprise a similar multi-leaf collimator having pneumatic leaf actuation mechanisms, which may be driven by the same or different compressed air system as for the therapeutic radiation source.

Imaging System

Imaging data may be acquired and used to register the position of the patient relative to the gantry (110) and the therapeutic radiation sources (120, 122). Accurate registration of the patient to the radiotherapy system facilitates the accurate delivery of the radiation treatment. Images and/or data acquired by the imaging system (140) may also be used to identify the positions of target volumes and sensitive structures that are to be avoided. In some variations, the imaging system (140) of the radiotherapy system may be an MM imaging system, kVCT imaging system, PET imaging system, CT/PET imaging system, MVCT imaging system, combinations thereof, and the like. Imaging systems coplanar with a treatment plane may comprise one or more of portal kV, kVCT, PET, MM, SPECT, and MVCT. The field-of-view of the imaging beam (140) may be configured to include one or more of the system isocenter (150) and treatment plane. This may reduce margins as the patient platform (170) and patient (160) are stationary throughout imaging and dose delivery. In some variations, the imaging system (140) may be configured to use different imaging systems for different steps of a radiotherapy procedure. For example, a set of patient registration images may be acquired using a low dose kVCT or PET/CT system while a set of high-resolution dose delivery images (e.g., tomographic snapshots) may be acquired using a high-dose kVCT system.

In some radiation therapy systems, an imaging system (140) may comprise a kV radiation source and corresponding detector provided for imaging purposes (e.g., CT imaging). The kV radiation source and detector may both be mounted on the rotatable gantry. The kV radiation source and detector may be located at different circumferential and/or longitudinal locations from the therapeutic radiation sources such that the imaging beam generated by the kV radiation source is in a different plane from the therapeutic radiation source.

In some variations, an imaging system (140) may comprise a kV radiation source, a kV detector (184), and a series of static and dynamic collimator elements (not shown) to control the shape of the radiation beam emitted from the kV radiation source. For example, a series of two static collimators may define an aperture profile along two axes (e.g., X-axis, Y-axis) whose geometry may be defined by their relative location to system isocenter and the kV detector (184). Additionally, an imaging system (140) may comprise a collimation mechanism mounted on the rotatable gantry and disposed in the beam path of the kV detector. The collimation mechanism may be configured to adjust the kV beam irradiation field size and/or shape incident on the patient and kV detector (184). The collimation mechanism may comprise an electrical actuator, a collimator comprising beam-limiting elements or collimator leaves, and a position-sensing circuit. The collimation mechanism may be configured to rapidly adjust the position of its beam-limiting elements via an electrical actuator and position-sensing circuit.

Figure 1B:
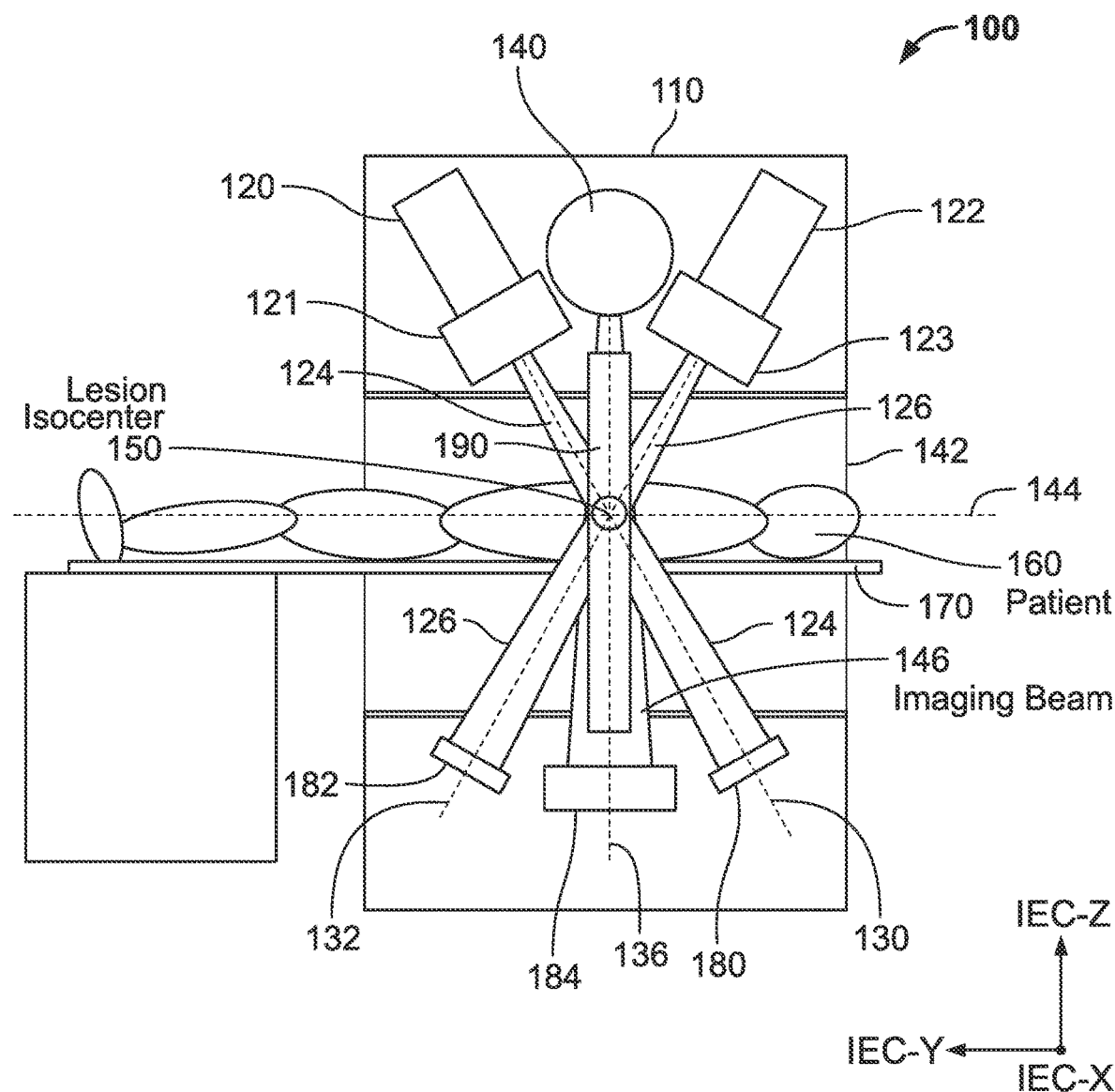
FIG. 1B depicts a schematic cross-sectional view of one variation of a system for flash radiotherapy.

FIG. 1B depicts a schematic cross-sectional side view of another variation of a radiation therapy system (100) similar to the system (100) depicted in FIG. 1A where similar elements and reference numbers are not repeated. The system (100) in FIG. 1B includes an imaging system (140) further comprising a set of PET detectors (190) disposed circumferentially around the gantry (110) at different circumferential positions than the first and second therapeutic radiation sources (120, 122). The kV radiation source (140) and PET detector (190) of the imaging system (140) may be disposed at the same longitudinal location of the gantry (110) such that their imaging planes intersect, overlap, and/or co-localize with the system isocenter (150). A kV radiation source (140) and PET detector (190) may be configured to image a plurality of parameters of a patient target region (e.g., physiological state, location, shape, size, SUV) and may provide imaging modality redundancy and additional confirmation and/or checks of patient and/or patient target positioning.

The systems described herein comprising multiple radiation beam subsystems that emit non-coplanar radiation beams may be useful in increasing radiotherapy system availability and improving patient workflow. As used herein, availability generally refers to the ability of a radiotherapy system as a whole to operate at or above a minimum level of functionality. Reliability generally refers to the ability of a specific subsystem to operate properly. For example, a system comprising multiple radiation beam subsystems will still be available for a radiotherapy treatment session if at least one of subsystems remain functional. Assuming, for the sake of example, that a single radiation beam subsystem of the radiotherapy system has a subsystem reliability (e.g., up-time) of 95%, then a radiotherapy system with multiple radiation beam subsystems will have an aggregate total system reliability of less than 95% (e.g., 90%) because the chance that at least one subsystem will malfunction increases as the number of subsystems increases. However, increasing the number of radiation beam subsystems also increases the availability of the system (e.g., increase from 95% to 97.5%) since radiotherapy may still be performed, albeit at lower efficiency, when at least one of the radiation beam subsystems is functioning. This may be important to reduce total dose exposure for patients who have received a dose of PET tracer for radiotherapy. For example, a patient who has been injected with a dose of PET tracer may be unnecessarily exposed to radiation (i.e., from the PET tracer) if their radiotherapy treatment session must be delayed due to the failure in a single radiation beam subsystem that renders the entire system inoperable. However, if another radiation beam subsystem is available, then the patient may optionally proceed to receive radiation treatment.

Figure 1C:
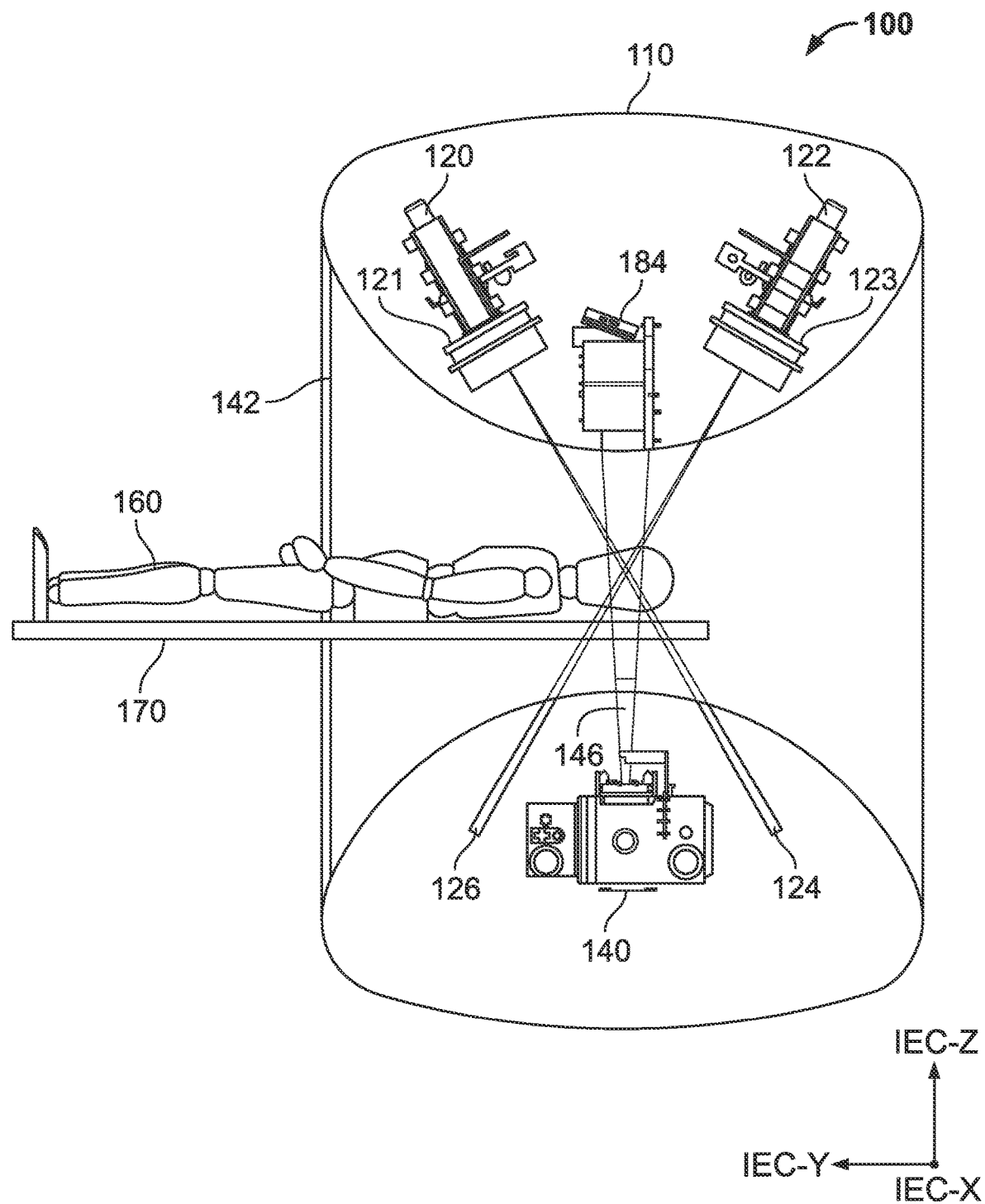
FIG. 1C depicts a schematic partial cutaway side view of one variation of a system for flash radiotherapy.
Figure 1D:
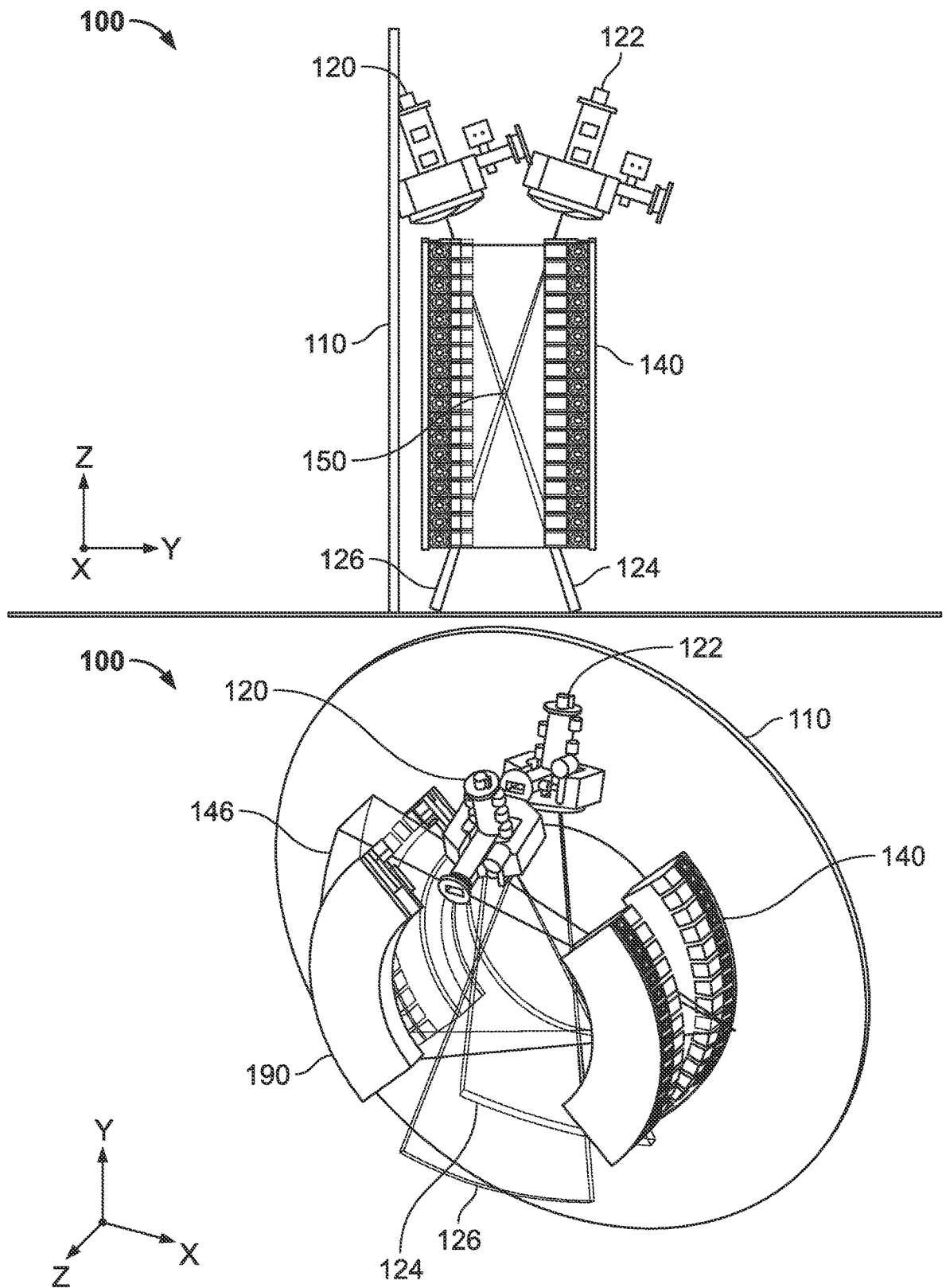
FIG. 1D depicts side and perspective component views of one variation of a system for flash radiotherapy.

FIG. 1D depicts a schematic cross-sectional side view and perspective view of another variation of a radiation therapy system (100) similar to the system (100) depicted in FIG. 1B where similar elements and reference numbers are not repeated.

The system (100) in FIG. 1D includes an imaging system (140) further comprising a first set of PET detectors (190) mounted to a portion of the gantry (110). In some variations, the PET detectors (190) may span along at least a portion of a circumference of the gantry (110), for example, along an inner circumference, outer circumference, or any location between the inner and outer circumference of the gantry (110). In some variations, the PET detectors may span a subset of a circumference of the gantry (110) (e.g., 180 degrees). For example, a first array of PET detectors may be mounted on a first arc segment or length of the gantry (110) having a length of about 25% of the circumference of the gantry (110) and a second array of PET detectors may be mounted on a second arc segment or length of the gantry (110) having a length of about 25% of the circumference of the gantry (110). In this variation, the portion of the gantry (110) circumference that is covered by PET detectors is about 50% of the circumference.

The first and second arrays of PET detectors may be located generally opposite each other (e.g., directly opposite each other, such that the center of each of the PET detector arrays are about 180 degrees from each other), or alternatively, the first array of PET detectors may be offset from the second array of PET detectors so that they are not opposite each other (e.g., the center of each of the PET detector arrays are less than about 180 degrees from each other, for example, about 45 degrees, about 90 degrees, or about 120 degrees, or about 150 degrees, etc.). In variations where the PET detectors are not on the same plane or "slice" of the ring as the therapeutic radiation source (i.e., where the PET detectors are not coplanar with the therapeutic radiation source), the PET detectors may span the entire circumference of its ring (e.g., 360 degrees). Optionally, some systems may comprise fourth and fifth arrays of PET detectors. The fourth and fifth PET detector arrays may not be coplanar with the therapeutic radiation source and/or the first and second PET detector arrays (i.e., may be on a different plane or "slice" of the ring as the therapeutic radiation source and/or the first and second PET detector arrays). For example, the first and second PET detector arrays may be mounted opposite each other on a first ring, and the third and fourth PET detector arrays may be mounted opposite each other on a second ring that is not coplanar with the first ring (e.g., center point of the first and second rings do not overlap in space).

In some variations, a system with one or more PET detector arrays may comprise one or more PET calibration sources disposed on the gantry and/or any structures of the system such that the calibration source(s) do not co-localize with a patient treatment region of the system. For example, the one or more PET calibration sources may comprise a positron-emitting capsule that is located on a stationary portion of the gantry and/or may be co-planar with the PET detector arrays. The location of the calibration source and the rate of positron emission may be known to the system, and the PET detectors may be configured to constantly and/or routinely polled to identify positron annihilation emission events (i.e., emission paths or lines-of-response or LORs) that correspond with the known location and emission rate of the calibration source in order to confirm that the PET detector arrays are functioning within specified tolerances. If the PET detector arrays are unable to detect positron annihilation events that match the profile of emission events that would have originated from a PET calibration source, the system controller may be configured to generate a notification and/or warning to indicate that the PET detector arrays may faulty, serviced, calibrated, and/or replaced. Additional details of such PET detector calibration and fault detection mechanism are described in International Patent Application Serial No. PCT/US2018/046132, filed on Aug. 9, 2018, the contents of which are hereby incorporated by reference in its entirety.

Gantry

In some variations, a radiotherapy system may comprise a gantry comprising a plurality of rings. For example, the gantry (110) may comprise three concentric rings including a first ring, a second ring, and a third ring between the first and second rings. A first therapeutic radiation source (120) may be mounted on the first ring, a second therapeutic radiation source and the imaging system (140) may be mounted on the second ring, and the imaging system may be mounted on the third ring. This configuration may provide different beam delivery angles that may intersect to form a spheroidal dose to the patient (160). Furthermore, therapeutic radiation sources mounted on offset rings at an angle to each other may reduce the overall size of the system (100).

In some variations, the radiotherapy systems described herein may comprise a circular gantry having a stationary frame and at least one rotatable ring coupled to the stationary frame via a corresponding rotating mechanism. The rotating mechanism may comprise a slip ring and a drive train that is capable of rotating the ring. In some variations, the rotatable ring may be configured to continuously rotate 360 degrees in one or more directions (e.g., clockwise and/or counterclockwise), while in other variations, the rotatable ring may be configured to rotate less than 360 degrees in one or more directions (e.g., rotate clockwise about 270 degrees and counterclockwise about 270 degrees, rotate clockwise about 150 degrees from a vertical axis and counterclockwise about 135 degrees from the vertical axis, rotate clockwise about 180 degrees from the vertical axis and about 150 degrees from the vertical axis, arcs, partial segments of a circle, etc.). A controller may be configured to adjust the rotation speed of the gantry. For example, the rotatable ring may be configured to rotate at a constant rotation speed or a variable rotation speed.

In some variations, a gantry may comprise a temperature management system configured to dissipate any heat generated due to the motion of the rotatable ring and/or the components mounted on the ring. The temperature management system may comprise two sets of heat exchangers and ducting, the first set may be configured to transfer heat from the rotating gantry to the stationary frame and a second set located on the stationary frame may be configured to transfer heat from the stationary frame to an external thermal system (e.g., a closed-loop, facility liquid system). For example, the first set may comprise forced-air heat exchangers and/or radiative heat exchangers, and the second set may comprise heat exchangers coupled to external, chilled fluid of the external thermal system.

Bore

The radiotherapy systems as described herein may comprise one or more gantries that define a bore including a patient treatment area. As shown in FIGS. 1A, 1B, and 1D, the bore (142) may be generally cylindrical. FIG. 1C depicts a schematic cross-sectional side view of a variation of a radiation therapy system (100) that may be similar to the system (100) depicted in FIG. 1A where similar elements and reference numbers are not repeated. In some variations, as shown in FIG. 1C, the bore (142) may be tapered. For example, the inward facing surfaces of the gantry (110) may be generally toroidal. The bore (142) may have a first diameter at a first longitudinal portion, a second diameter at a second longitudinal position, and a third diameter at a third longitudinal position. The third diameter may be less than or equal to at least one of the first and second diameters. For example, the first longitudinal position may correspond to a longitudinal position of the first therapeutic radiation source (120). The second longitudinal position may correspond to a longitudinal position of the second therapeutic radiation source (122). The third longitudinal position may correspond to a longitudinal position of the imaging system (140). The increased diameter at the first and second longitudinal positions of the bore (142) may accommodate the mounting of the first and second therapeutic radiation sources (120, 122) higher (i.e., further away from the central longitudinal axis of the bore) than the imaging system radiation source (140) (e.g., kVCT radiation source).

In some variations, the imaging system (140) may be mounted to the gantry (110) at a first distance from the system isocenter (150), and the therapeutic radiation sources (120, 122) may be mounted to the gantry (110) at a second distance from the system isocenter (150). In some of these variations, the first distance may be greater than the second distance. Alternatively, the first distance may be less than the second distance. A larger second distance may reduce a maximum dose rate but may improve potential penumbra and margins of the radiation beams. In some variations, the taper of a bore may generally follow the angle of the therapeutic radiation sources. A taper in the bore (142) may further aid lighting and visibility of the patient (160) and patient platform (170).

Patient Platform

In some variations, the patient platforms described herein may be configured to provide up to six degrees of freedom to improve patient alignment and/or increase the number of beam delivery angles of the system. For example, the patient platform may be configured to adjust an azimuthal range of motion of up to about ±360(N/4) degrees for each therapeutic radiation source, where N is the number of therapeutic radiation sources of the system.

In some variations, the systems, devices, and methods disclosed herein may comprise one or more patient platforms, and methods of use thereof as described in International Patent Application Serial No. PCT/US2017/061855, filed on Nov. 15, 2017, the contents of which are hereby incorporated by reference in its entirety.

Therapeutic Radiation Source Arrays

Figure 2A:
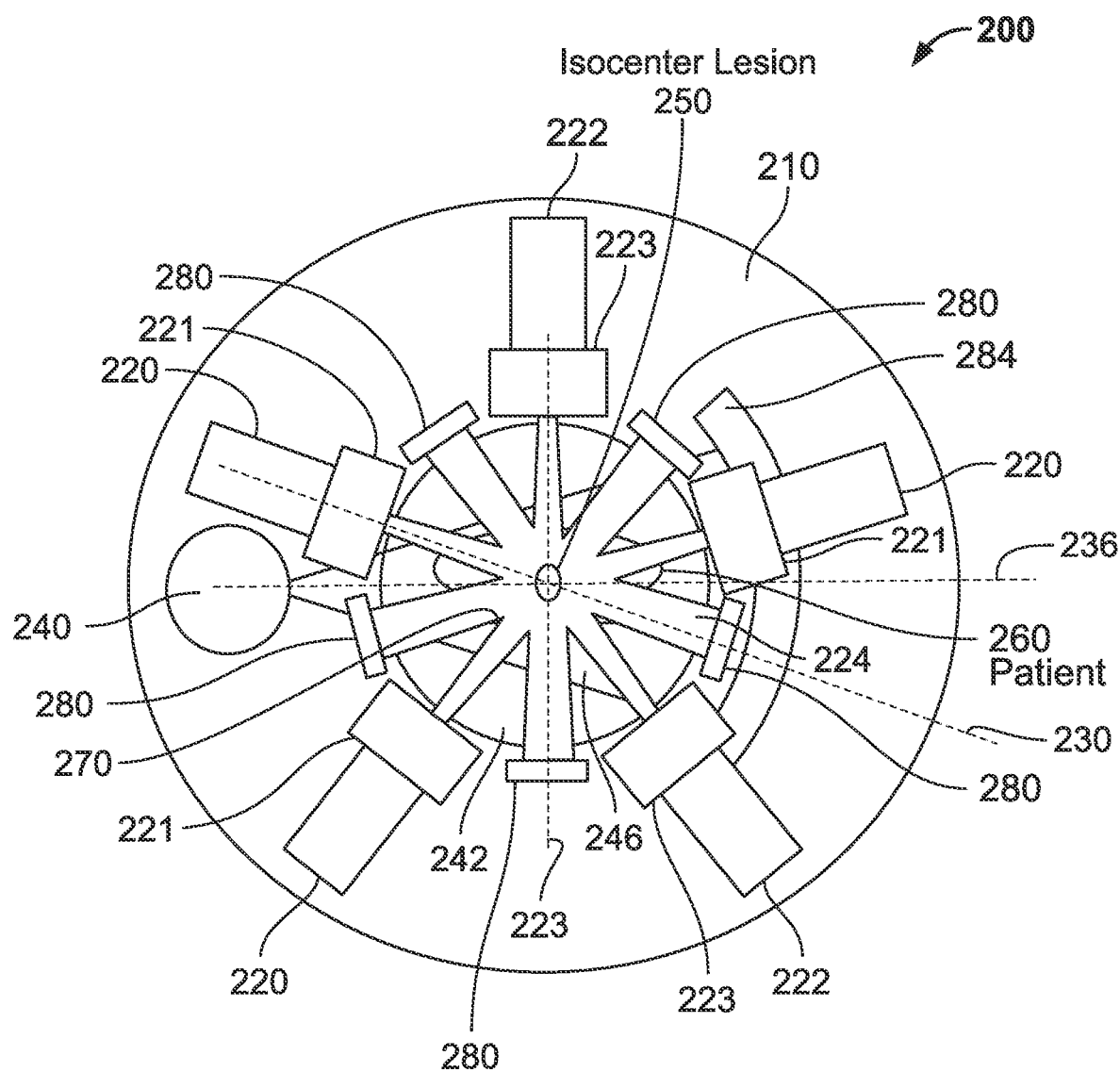
FIG. 2A depicts a schematic front view of one variation of a system for flash radiotherapy.

Some variations of the radiation therapy systems described herein may comprise a first and second array of therapeutic radiation sources (with multiple radiation sources in each array) configured to rapidly deliver a prescribed dose to a patient. FIG. 2A depicts schematic cross-sectional front view of one variation of a radiation therapy system (200) comprising a first array of therapeutic radiation sources (220) and a second array of therapeutic radiation sources (222), a gantry (210), and a patient platform (270) (e.g., couch top) configured to hold a patient (260) disposed on top of the patient platform (270). The patient platform (270) may be configured to move within a bore (242) of the gantry (210). The bore (242) may have a longitudinal axis that intersects a system isocenter (250) of the system (200). The gantry (210) may be a circular gantry (e.g., ring gantry). In some variations, the gantry (210) may comprise one or more rings (e.g., three concentric rings). The system (200) may comprise a first array of therapeutic radiation sources (220) and a second array of therapeutic radiation sources (222) each mounted on the gantry (210). A first array of beam-shaping assemblies (221) may be disposed over the first array of therapeutic radiation sources such that each beam-shaping assembly is located in a radiation beam path of a corresponding therapeutic radiation source of the first array, and a second array of beam-shaping assemblies (223) may be disposed over the first array of therapeutic radiation sources such that each beam-shaping assembly is located in a radiation beam path of a corresponding therapeutic radiation source of the second array. For example, a beam-shaping assembly (221) may be disposed over each therapeutic radiation source of the first array of therapeutic radiation sources (220) along respective first radiation beam axes (230), and a beam-shaping assembly (223) may be disposed over each therapeutic radiation source of the second array of therapeutic radiation sources (222) along respective second radiation beam axes (232).

The first array of therapeutic radiation sources (220) may be configured to emit respective first radiation beams (224) defining respective first radiation beam axes (230) and the second array of therapeutic radiation sources (222) may be configured to emit respective second radiation beams (226) defining respective second radiation beam axes (232). The second radiation beam axes (232) may be oriented at an angle with respect to the first radiation beam axes (230). A detector (280) (e.g., MV detector) may be mounted on the gantry (210) opposite to each therapeutic radiation source of the first array and second array of therapeutic radiation sources (220, 222). A detector may be provided to detect the collimated, high energy radiation of each radiation beam (224, 226). A detector (280) provided for each therapeutic radiation source may improve one or more of imaging, system quality assurance, and real-time quality assurance performed by the system (200).

The system (200) may further comprise an imaging system (240) mounted on the gantry (210) and an imaging detector (284) mounted on the gantry (210) opposite to the imaging system (240). The imaging system (240) may be configured to generate an imaging beam (246) having a field-of-view and a imaging central axis (236) that intersects the center of the field-of-view. The imaging beam (246) further defines an imaging plane that may be oriented, for example, along a transverse plane of the system (200). For example, the imaging plane within the imaging beam (246) may intersect (e.g., irradiate) a width-wise cross-section of the bore (242). In some variations, the system isocenter (250) may be defined as the intersection of a central longitudinal axis (e.g., extending out of the page in FIG. 2B) of the bore (242) and the imaging central axis (236) of the imaging field-of-view.

The first array of therapeutic radiation sources (220) may be configured to emit respective first radiation beams (224) defining respective first radiation beam axes (230) and the second array of therapeutic radiation sources (222) may be configured to emit respective second radiation beams (226) defining respective second radiation beam axes (232). The second radiation beam axes (232) may be oriented at an angle with respect to the first radiation beam axes (230). In some variations, the therapeutic radiation sources (220, 222) may be configured such that the first radiation beam axes (230) and the second radiation beam axes (232) intersect at the system isocenter (250). In some variations, the first and second radiation beams (224, 226) and the imaging beam (246) (e.g., imaging plane) may be configured to intersect at the system isocenter (250).

A first array of detectors (280) may be mounted on the gantry (210) opposite to the first array of therapeutic radiation sources (220) and a second array of detectors (282) may be mounted on the gantry (210) opposite to the second array of therapeutic radiation sources (222). A detector may be provided to detect the collimated, high energy radiation of a respective radiation beam (124, 126). A detector (280, 282) provided for each therapeutic radiation source (220, 222) may improve one or more of imaging, system quality assurance, and real-time quality assurance performed by the system (200).

In some variations, one or more treatment planes may be defined by the intersection of the first and second radiation beams (224, 226) and imaging beam (246). In some variations, he patient (260) may be positioned on a patient platform (270) such that the patient target region (e.g., lesion) is located in the treatment plane and/or is located (e.g., overlapping) with the system isocenter (250). The imaging beam (246) may intersect the system isocenter (250) where a lesion of the patient (260) may be positioned. This allows the imaging system (240) to at least image the lesion and surrounding healthy tissue. The imaging plane may be used to generate imaging data for use with registration, treatment planning, verification, and dose delivery. For example, the imaging system (240) and the patient (260) may be configured such that a lesion of the patient (260) may be positioned within the imaging plane and/or at system isocenter (250).

In some variations, the therapeutic radiation sources (220, 222) may be configured such that the first and second radiation beams (224, 226) are not coplanar with the imaging beam (246). That is, the first and second radiation beam axes (230, 232) may be oriented at an angle with respect to the imaging central axis (236). This configuration allows the lesion positioned at a system isocenter (250) to receive the first and second radiation beams (224, 226) from their respective beam delivery angles. In some variations, the first and second radiation beams (224, 226) may intersect at a system isocenter (250) to provide a spheroidal dose of radiation.

The radiation beam axes (230) of each of the first array of therapeutic radiation sources (220) may be oriented towards a first focal point within the field-of-view. The radiation beam axes (232) of each of the second array of therapeutic radiation sources (222) may be oriented towards a second focal point within the field-of-view. The imaging central axis (236), the first focal point, and the second focal point each intersect at the system isocenter (250). The first radiation beam axes (230) of the first array of therapeutic radiation sources (220) may be at a non-zero angle relative to the imaging central axis (236). The second radiation beam axes (232) of the second array of therapeutic radiation sources (222) may be at a non-zero angle relative to the imaging central axis (236). In some variations, the non-zero angle may be from about 10° to about 60°. As shown in at least FIGS. 2C and 2D, the first and second arrays of therapeutic radiation sources (220, 236) are not coplanar with the imaging plane of the imaging beam (246). Accordingly, the first and second radiation beams (224, 226) may be non-parallel to the imaging plane such that they each intersect the imaging plane at only one point.

The radiotherapy system (200) may further comprise a controller (not shown) in communication with the first array of therapeutic radiation sources (220), the second array of therapeutic radiation sources (222), and the imaging system (240). For example, the controller may be configured to activate the first and second array of therapeutic radiation sources (220, 222) simultaneously to deliver up to an entire prescribed radiation dose in one pulse.

The imaging system (240) may be mounted on the gantry (210) between the first and second array of therapeutic radiation sources (220, 222). For example, the first and second array of therapeutic radiation sources (220, 222) and the imaging system (240) may be disposed along a length of the gantry (110). In some variations, the first array of therapeutic radiation sources (220) may be located at a first longitudinal position along the bore (242) and the second array of therapeutic sources (222) may be located at a second longitudinal position along the bore (242). The imaging system (240) may be located at a third longitudinal position between the first and second longitudinal positions. For example, FIG. 2D is a cross-sectional side view of the system (200) showing the relative longitudinal positions of the first array of therapeutic radiation sources (220), the second array of therapeutic radiation sources (222), and the first imaging system (240) therebetween. Accordingly, the mounting locations of the first and second therapeutic radiation sources (220, 222) are not coplanar with the imaging plane (242). In some variations, the bore (242) may be tapered (not shown). The bore (242) may have a first diameter at a first longitudinal portion, a second diameter at a second longitudinal position, and a third diameter at a third longitudinal position. The third diameter may be less than or equal to at least one of the first and second diameters.

In some variations, a first array of therapeutic radiation sources (220) comprises a first array of linear accelerators (linacs) thermally tuned to the each other. The second array of therapeutic radiation source (222) comprises a second array of linacs thermally tuned to each other. In some variations, the first and second arrays of therapeutic radiation sources (220, 222) may be configured to emit first and second radiation beams (224, 226) having an energy of at least about 1 MV, e.g., about 3 MV, about 4 MV, about 6 MV, about 7 MV, etc. For example, the first and second radiation beams (224, 226) may have an energy of about 6 MV or more. A higher dose rate and/or a greater number of simultaneous radiation beams allows the system to deliver a prescribed dose in less time, thereby improving one or more of efficiency, cost, redundancy and availability of the system (200). Alternatively or additionally, one or more of the therapeutic radiation sources may be configured to emit radiation beams having an energy less than about 6 MV (e.g., about 1 MV, about 2 MV, about 3 MV, about 4 MV, etc.) with a sufficient intensity level (e.g., flux) to deliver the prescribed dose. For example, a therapeutic radiation source may be configured to emit radiation beams having an energy of about 6 MV or more to deliver dose to tumors at deep locations and/or may be configured to emit radiation beams having an energy of about 3 MV or less (e.g., about 1 MV or less) to deliver dose to tumors at shallow or superficial locations (e.g., in a patient's skin, just below a patient's skin surface, etc.).

In some variations, the therapeutic radiation source may comprise a cold-cathode configured to discharge stored electrical energy in a single pulse as described herein. In some variations, the system (200) may comprise a first and second RF source (not shown) configured to supply radiofrequency power to the respective first and second arrays of therapeutic linacs (220, 222). Each linac may comprise an electron gun. That is, the system (200) may comprise first array of electron guns that correspond with the first array of linacs (220) and a second array of electron guns that correspond with the second array of linacs (222). The first and second RF source may be configured to supply radio frequency power to accelerate electrons generated by a respective electron gun. The accelerated electrons may be directed to a heavy-metal target of a linac, and the collision of the electrons with the heavy-metal target (e.g., X-ray converter target, tungsten target) may generate high-energy photons or X-rays. In some variations, a single RF source may be used to accelerate the electrons from a plurality of electron guns or each therapeutic radiation source may have its own RF source. The intensity of the first and second radiation beams (224, 226) may be independently modulated using a respective electron gun. For example, an electron gun may be configured to provide intensity modulation based on one or more of pulse width, gating pulses, combinations thereof, and the like. In some embodiments, at least one of the first and second RF sources and electron guns may be collectively configured to intensity modulate (e.g., gate) at least one of the first and second radiation beams (224, 226).

In some variations, one or more RF sources may be coupled to one or more linacs of the radiotherapy system as described herein. In some variations, a set of linacs may be dynamically coupled (e.g., interleaved) to one or more RF sources that match the resonant frequency of the linacs. In some variations, an RF source and a linac comprising an electron gun may be collectively configured to modulate an intensity (e.g., dose) of a radiation beam emitted by the linac as described herein.

As described herein, a therapeutic radiation beam may be generated by a linac and shaped by a beam-shaping assembly. In some variations, the beam-shaping assembly (221, 223) may comprise one or more of a primary collimator, secondary collimator, multi-leaf collimator, first jaw, second jaw, X-ray hardening filter, combinations thereof, and the like. In some variations, a radiation therapy system may further comprise an X-ray target converter comprising a target and a primary collimator, a dose chamber, upper jaws, a multi-leaf collimator (e.g., a binary MLC), and lower jaws. The primary collimator, upper jaws, the binary MLC, and lower jaws may shape the radiation beam emitted by the linac. The upper and lower jaws may move on curved rails that loosely focus to the virtual point spot of the target converter. In some variations, an X-ray hardening filter may be configured to shape received X-rays and output a flattened X-ray beam (e.g., a beam with a substantially consistent fluence or energy level across the irradiation field). For example, the X-ray hardening filter may be composed of metal (e.g., tungsten, steel, lead, uranium, aluminum) and may have a conical shape.

In some variations, the first beam-shaping assembly (221) comprises a first dynamic multi-leaf collimator and the second beam-shaping assembly (223) comprises a second dynamic multi-leaf collimator. In some variations, the dynamic multi-leaf collimator may be a two-dimensional multi-leaf collimator or a binary multi-leaf collimator. The two-dimensional multi-leaf collimator may be a variable circular collimator and optionally, an iris collimator. In some variations, the collimation of each radiation beam may be provided by a gimbaled collimator as described herein. For example, the collimation of each radiation beam may be provided by a bMLC/Jaw collimator for each therapeutic radiation source where each of the radiation beam component may be gimbaled in one or two dimensions.

In some variations, the imaging system (240) of the radiotherapy system (200) may be an MRI imaging system, kVCT imaging system, PET imaging system, CT/PET imaging system, MVCT imaging system, combinations thereof, and the like. Imaging systems coplanar with a treatment plane may comprise one or more of portal kV, kVCT, PET, MM, SPECT, and MVCT. The field-of-view of the imaging beam (240) may be configured to include one or more of the system isocenter (250) and treatment plane. In some variations, the imaging system (240) may be configured to use different imaging systems for different steps of a radiotherapy procedure. For example, a set of patient registration images may be acquired using a low dose kVCT or PET/CT while a set of high-resolution dose delivery images (e.g., tomographic snapshots) may be acquired using a high-dose kVCT.

Figure 2B:
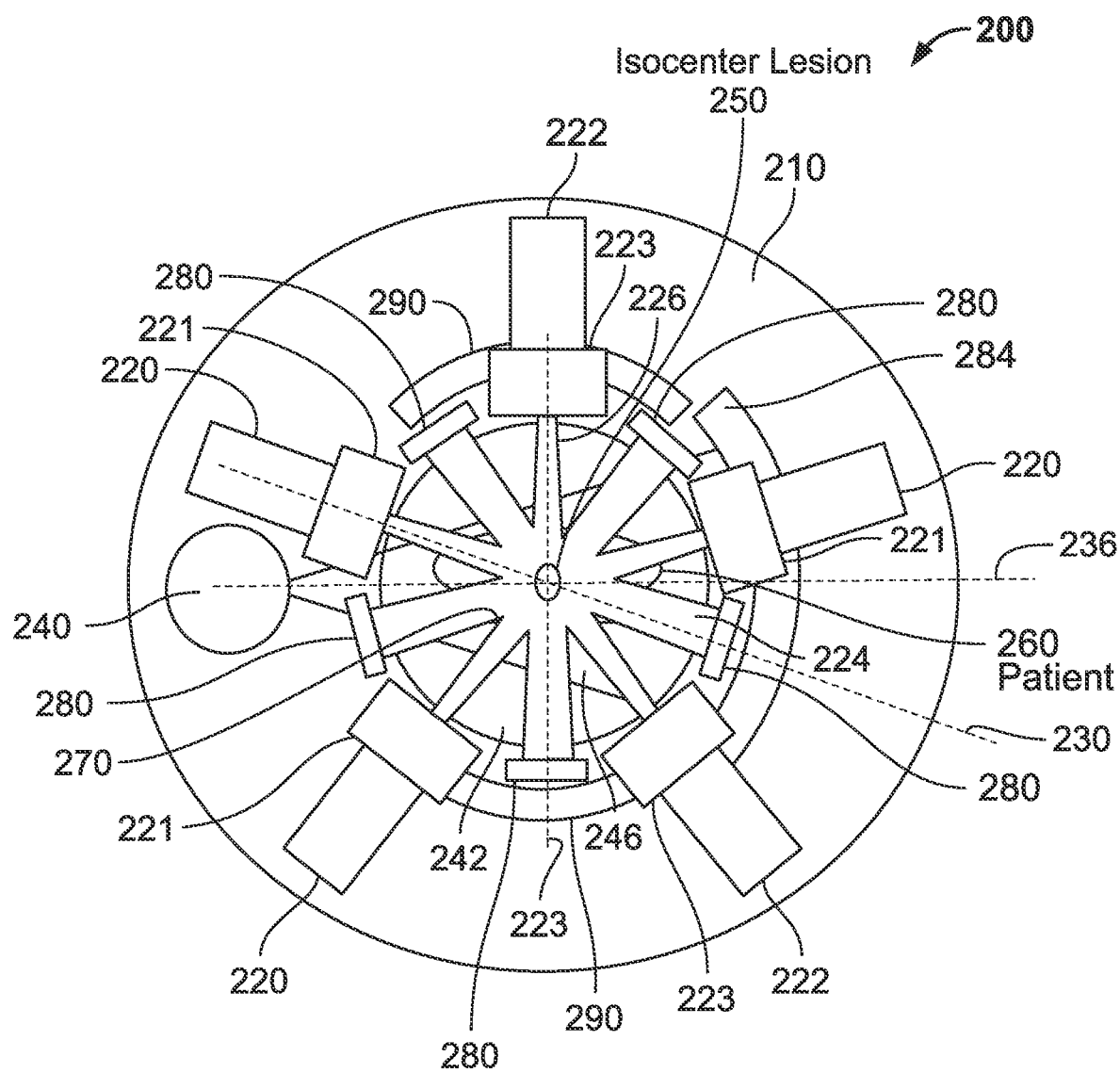
FIG. 2B depicts a schematic front view of one variation of a system for flash radiotherapy.

FIG. 2B depicts a schematic cross-sectional front view of another variation of a radiation therapy system (200) similar to the system (200) depicted in FIG. 2A where similar elements and reference numbers are not repeated. The system (200) in FIG. 2B includes an imaging system (240) further comprising a set of PET detectors (290) mounted along at least a portion of the circumference of the gantry (210) (e.g., inner circumference, outer circumference, or any location between the inner and outer circumference). In some variations, the PET detectors may span a subset of the circumference of the gantry (210) (e.g., 180 degrees). For example, a first array of PET detectors may be mounted on a first segment or length of the gantry (210) that has a length of about 25% of the circumference of the gantry (210) and a second array of PET detectors may be mounted on a second segment or length of the gantry (210) that has a length of about 25% of the circumference of the gantry (210). In this variation, the portion of the gantry (210) circumference that is covered by PET detectors is about 50% of the circumference.

The first and second arrays of PET detectors may be located generally opposite each other (e.g., directly opposite each other, such that the center of each of the PET detector arrays are about 180 degrees from each other), or alternatively, the first array of PET detectors may be offset from the second array of PET detectors so that they are not opposite each other (e.g., the center of each of the PET detector arrays are less than about 180 degrees from each other, for example, about 45 degrees, about 90 degrees, or about 120 degrees, or about 150 degrees, etc.). In variations where the PET detectors are not on the same plane or "slice" of the ring as the therapeutic radiation source (i.e., where the PET detectors are not coplanar with the therapeutic radiation source), the PET detectors may span the entire circumference of its ring (e.g., 360 degrees). Optionally, some systems may comprise fourth and fifth arrays of PET detectors. The fourth and fifth PET detector arrays may not be coplanar with the therapeutic radiation source and/or the first and second PET detector arrays (i.e., may be on a different plane or "slice" of the ring as the therapeutic radiation source and/or the first and second PET detector arrays). For example, the first and second PET detector arrays may be mounted opposite each other on a first ring, and the third and fourth PET detector arrays may be mounted opposite each other on a second ring that is not coplanar with the first ring (e.g., center point of the first and second rings do not overlap in space).

Figure 2C:
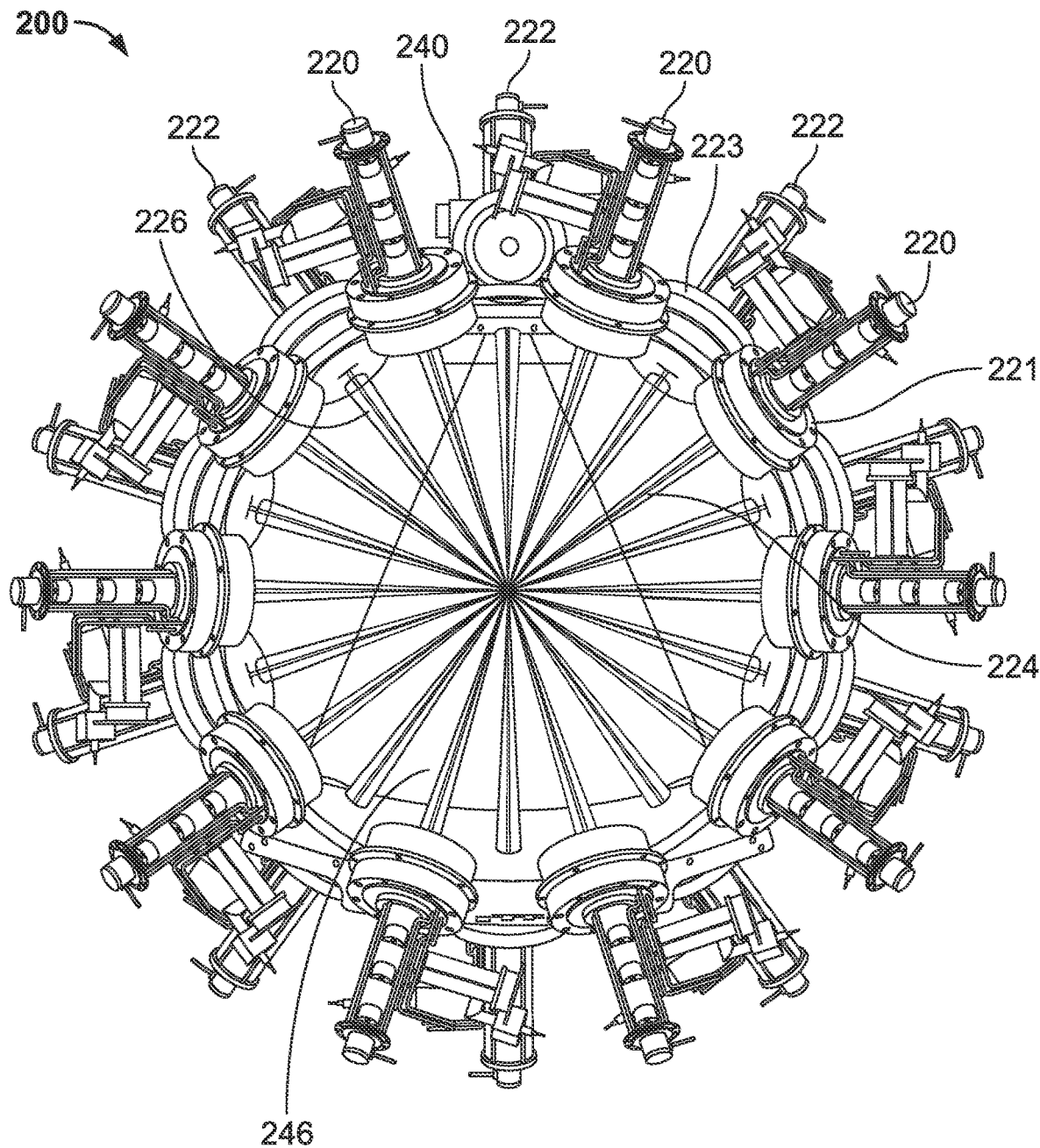
FIG. 2C depicts a perspective front view of one variation of a system for flash radiotherapy.
Figure 2D:
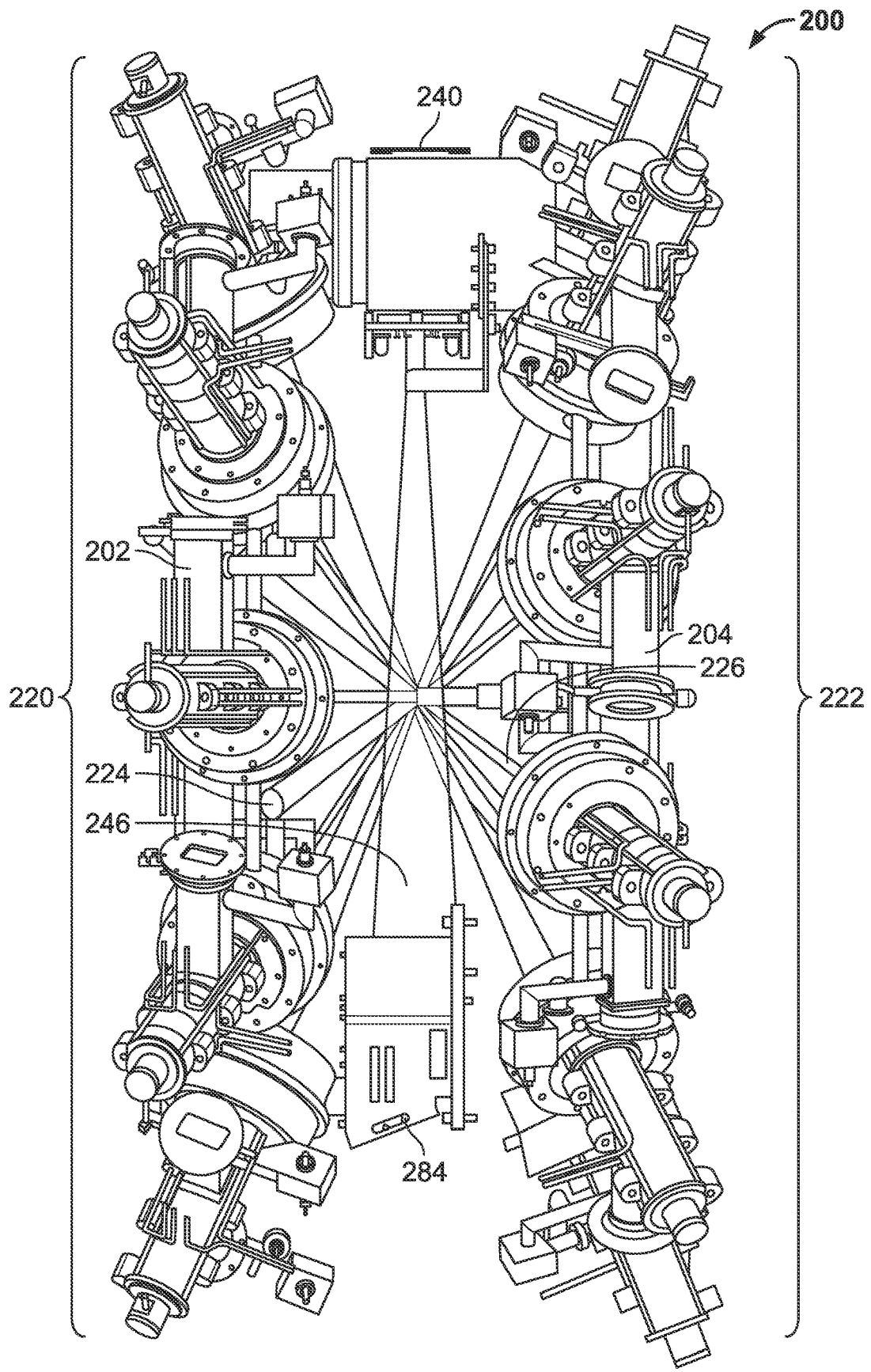
FIG. 2D depicts a perspective side view of one variation of a system for flash radiotherapy.

FIG. 2C depicts a schematic front view of another variation of the radiation therapy system (200) comprising a first array of therapeutic radiation sources (220) and a second array of therapeutic radiation sources (222). In some variations, the system (200) may comprise one or more rings. For example, as shown in the side view of FIG. 2D, the system (200) may comprise a first array of therapeutic radiation sources (220) and a second array of therapeutic radiation sources (222) each mounted on a respective ring (202, 204). Each beam-shaping assembly of a first array of beam-shaping assemblies (221) may be coupled to a corresponding therapeutic radiation source of the first array of therapeutic radiation sources (220). Each beam-shaping assembly of a second array of beam-shaping assemblies (223) may be coupled to a corresponding therapeutic radiation source of the second array of therapeutic radiation sources (222). Each beam-shaping assembly (221, 223) may be located in a radiation beam path of its respective therapeutic radiation source (220, 222). For example, a beam-shaping assembly (221) may be disposed over each therapeutic radiation source of the first array of therapeutic radiation sources (220), and a beam-shaping assembly (223) may be disposed over each therapeutic radiation source of the second array of therapeutic radiation sources (222).

The first array of therapeutic radiation sources (220) may be configured to emit respective first radiation beams (224) and the second array of therapeutic radiation sources (222) may be configured to emit respective second radiation beams (226). The second radiation beam axes (232) may be oriented at an angle with respect to the first radiation beam axes (230). The system (200) may further comprise an imaging system (240) mounted on the gantry (210). The imaging system (240) may be configured to generate an imaging beam (246) having a field-of-view and further defines an imaging plane that may be oriented, for example, along a transverse plane of the system (200).

Figure 2E:
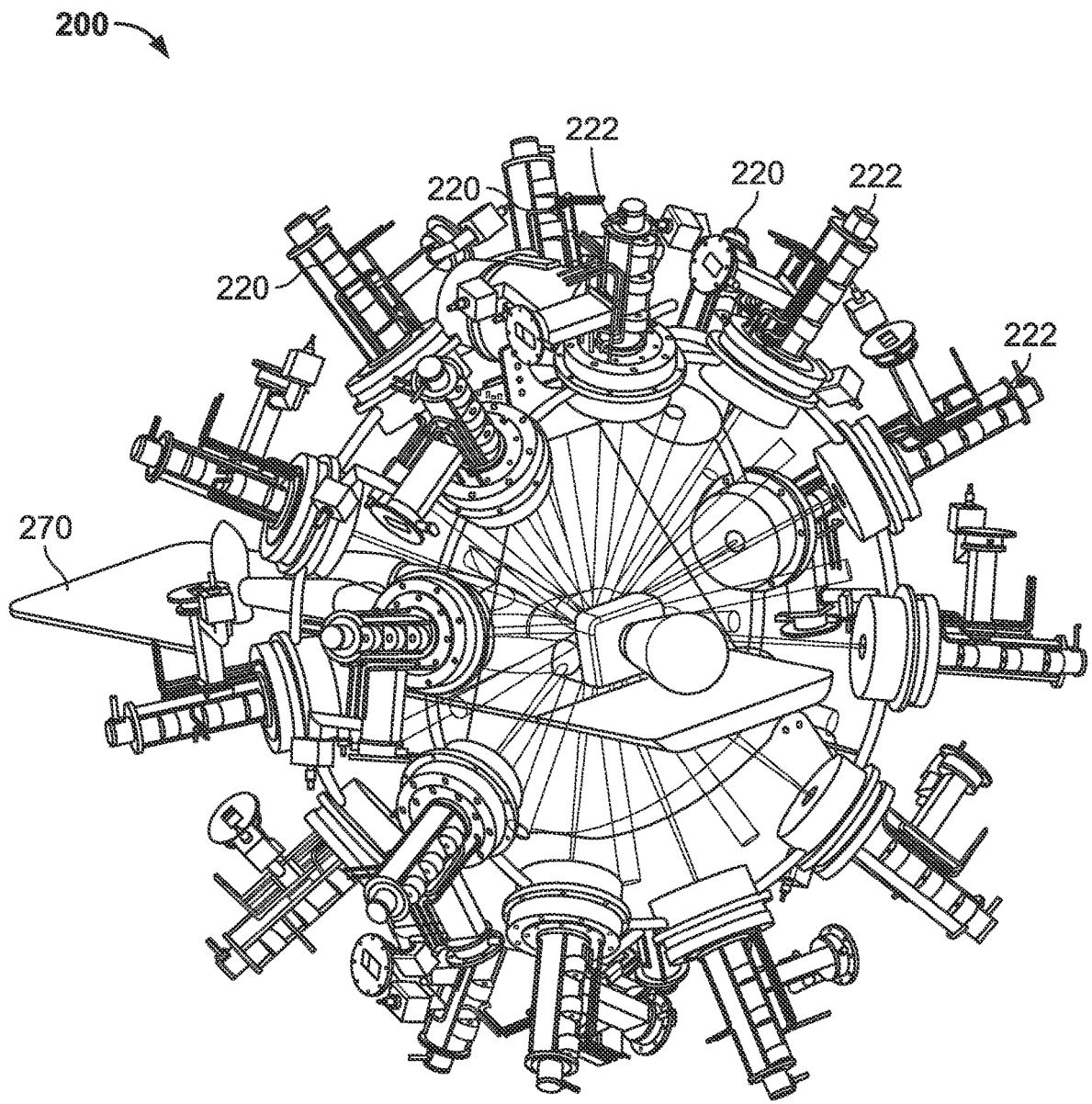
FIG. 2E depicts an elevated perspective rear view of one variation of a system for flash radiotherapy.
Figure 2F:
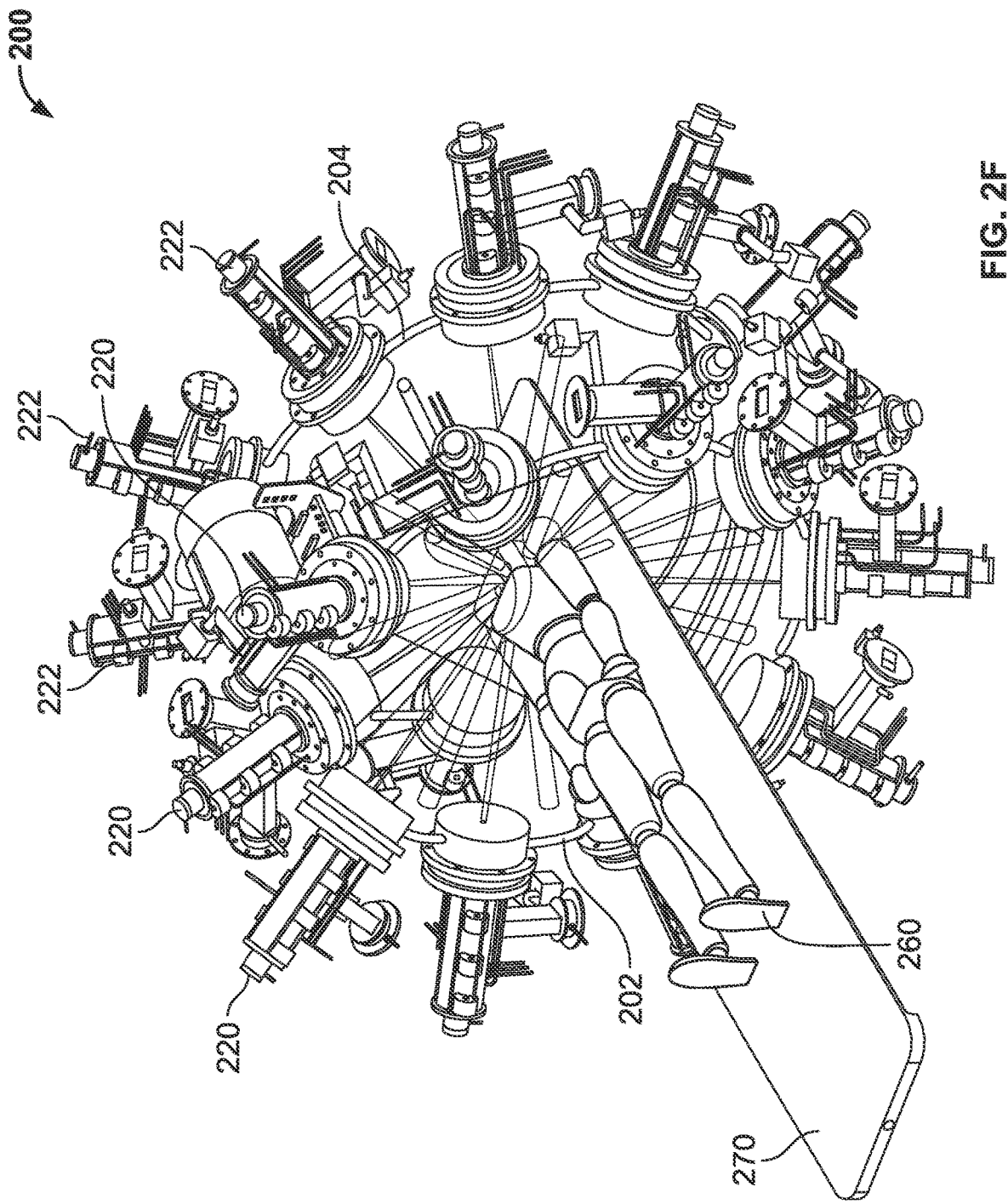
FIG. 2F depicts an elevated perspective front view of one variation of a system for flash radiotherapy.
Figure 2G:
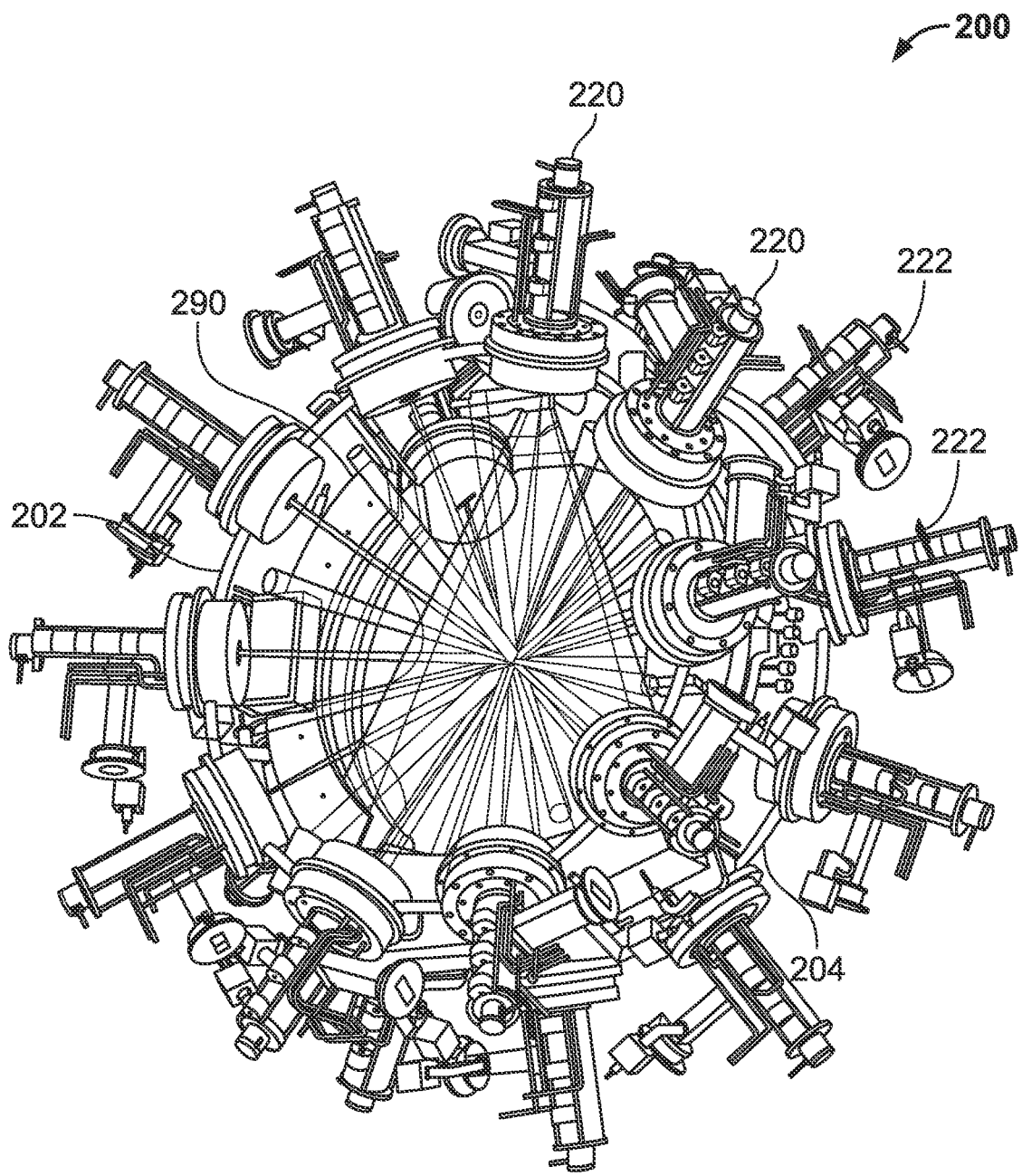
FIG. 2G depicts a perspective front view of one variation of a system for flash radiotherapy.
Figure 2H:
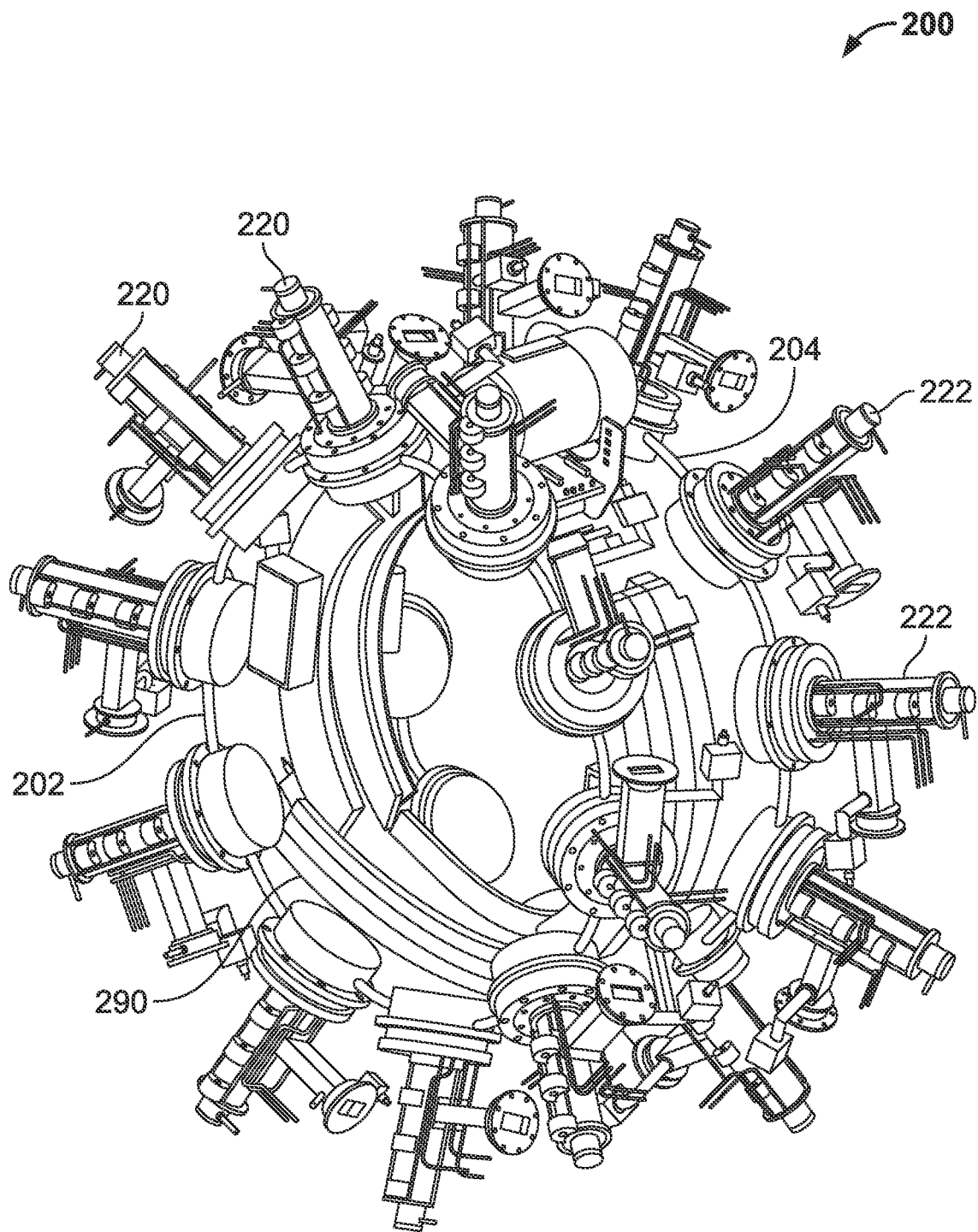
FIG. 2H depicts a perspective view of one variation of a system for flash radiotherapy.
Figure 2I:
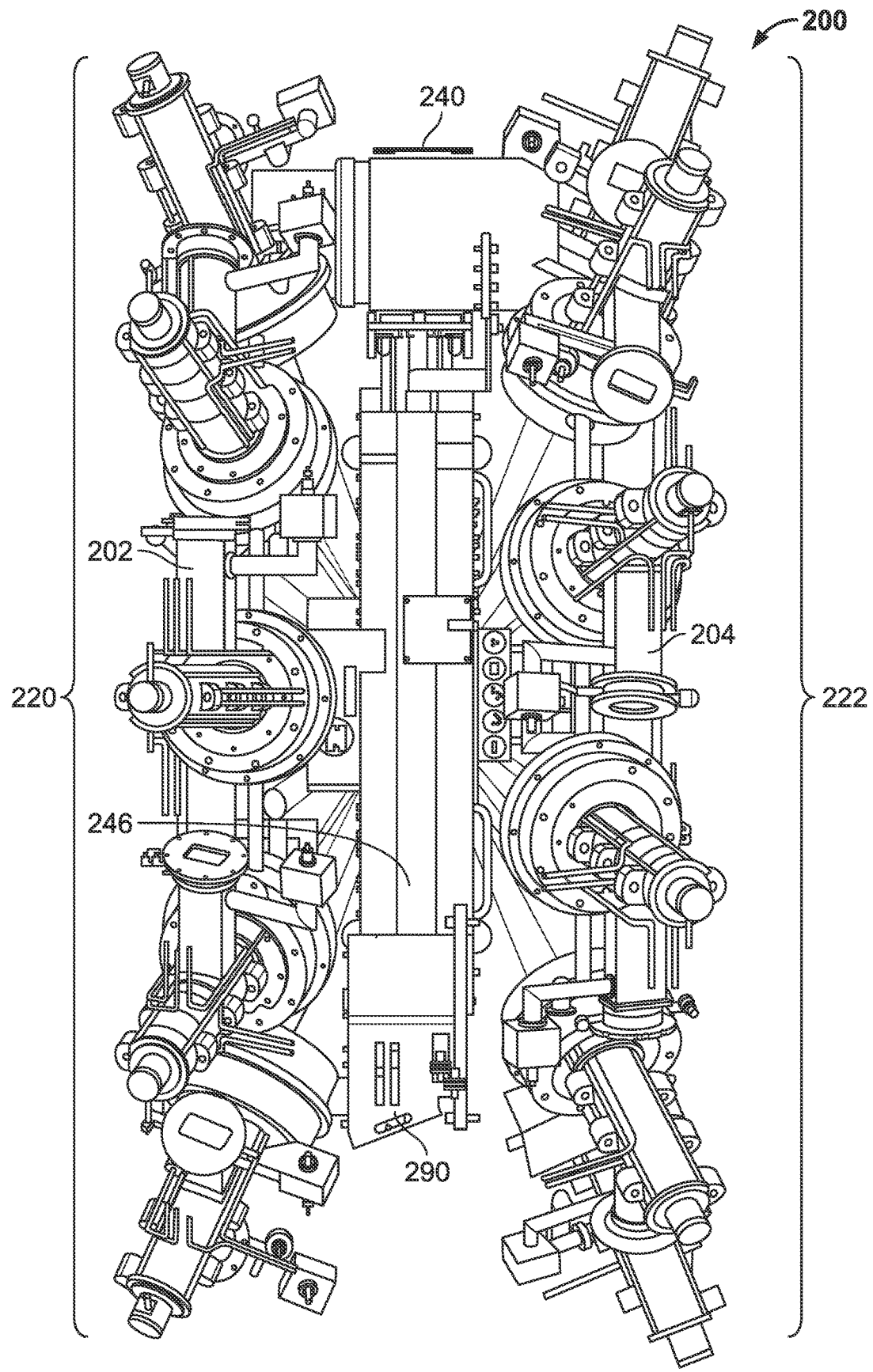
FIG. 2I depicts a perspective side view of one variation of a system for flash radiotherapy.

FIGS. 2E and 2F depict respective schematic front and back perspective views of the radiation therapy system (200) shown in FIG. 2C. FIGS. 2G and 2H depict respective schematic front and back perspective views of another variation of the radiation therapy system (200) shown in FIG. 2B. FIG. 2I depicts a cross-sectional side view of the radiation system (200) shown in FIG. 2A.

In some variations, a radiotherapy system may comprise a plurality of rings. For example, the gantry (200) may comprise three concentric rings including a first ring (202), a second ring (204), and a third ring (not shown) between the first and second rings (202, 204). The first array of therapeutic radiation sources (220) may be mounted on the first ring (202), the second array of therapeutic radiation sources (222) may be mounted on the second ring (204), and the imaging system (240) may be mounted on the third ring. This configuration may provide different beam delivery angles that may intersect to form a spheroidal dose to the patient (260). Furthermore, the array of therapeutic radiation sources mounted on offset rings at an angle to each other may reduce the overall size of the system (200).

As shown in FIG. 2D, the radiation beams (224, 226) are emitted from respective rings (202, 204) around an imaging plane of the imaging beam (246). The first radiation beams (224) of the first array of therapeutic radiation sources (220) may be at a non-zero angle relative to the imaging plane (including imaging system (240)). The second radiation beams (226) of the second array of therapeutic radiation sources (222) may be at a non-zero angle relative to the imaging plane. In some variations, the non-zero angle may be from about 10° to about 60°. Accordingly, the first and second radiation beams (224, 226) may be non-parallel to the imaging plane such that they each intersect the imaging plane at only one point.

In some variations, the systems (100, 200) described herein may be used in conjunction with emission-guided radiation delivery. Emission-guided radiation therapy (EGRT) applies radiation based on positron emission paths emitted by a positron emission tomography (PET) tracer that are localized to the tumor(s) during the treatment session. In addition to a radiation source configured to therapeutically irradiate a tumor region, an EGRT system may comprise at least one array of PET detectors configured to sense positron emission paths that originate within the tumor region, which may provide real-time location data. This may reduce the latency between the localization of a tumor and irradiation to that tumor. In order to timely respond to the detection of a positron emission path that indicates the real-time location of a tumor, one or more portions of the gantry system may rotate such that one or more PET detector arrays rotate together with a corresponding array of radiation beams. For example, each array of radiation beams may be angled with respect to each other such that the beams intersect each other in the patient (e.g., provide X-shaped beam delivery). In some variations, another imaging system (e.g., kV imaging, additional PET detector) may be provided between the first and second PET detector arrays.

Pulsed Therapeutic Radiation Source

Some variations of the radiation therapy systems described herein may comprise a single therapeutic radiation source configured to rapidly deliver a prescribed dose to a patient. A conventional therapeutic radiation source such as a linac may use microwave energy to accelerate low-current particle beams into a higher energy treatment beam. However, these sources may not be able to generate sufficient energy to deliver a prescribed dose in a single shot (e.g., single radiation beam pulse). Some of the therapeutic radiation sources described herein may comprise a pulsed power source configured to store electrical energy for rapid and controlled discharge such that a high dose, e.g., an entire prescribed dose, may be delivered to a patient in a single shot. For example, a high-voltage pulsed therapeutic radiation source may be configured to deliver a single shot radiation dose equivalent to between about 230 and about 750 conventional linac shots, based on a pulsed power source generating between about 30 kA and about 100 kA currents, a pulse width of about 50 nsec, and peak diode voltage of about 3 MV, and a linac generating about 280 mA current, a pulse width of about 3 μsec, and X-ray energy of about 6 MeV. The dose of one shot may be given by: current*voltage$^3$*pulse width.

The pulsed power therapeutic radiation sources described herein generating higher dose rates of radiation may reduce one or more margins, treatment times, the number of dose delivery cycles and/or treatment sessions, and may potentially improve patient outcomes.

Figure 3A:
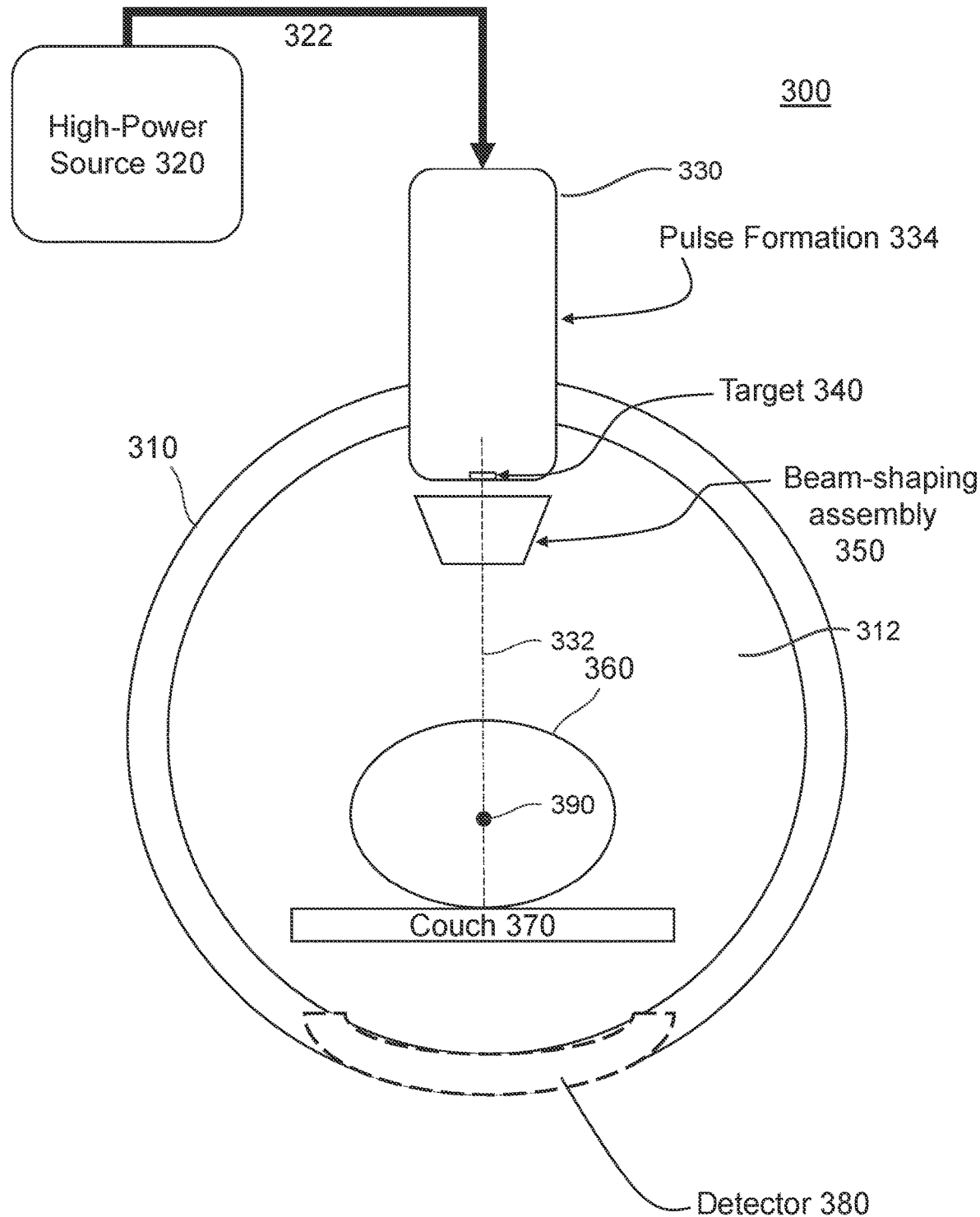
FIG. 3A depicts a schematic representation of a system for flash radiotherapy.

FIG. 3A depicts schematic cross-sectional side view of one variation of a flash radiation therapy system (300) comprising a gantry (310) and a patient platform (370) (e.g., couch top) configured to hold a patient (360) disposed on top of the patient platform (370). The patient platform (370) may be configured to move within a bore (312) of the gantry (310). The gantry (310) may be a circular gantry (e.g., ring gantry) and may comprise a therapeutic radiation source (330) mounted on the gantry (310). A beam-shaping assembly (350) may be coupled to the therapeutic radiation source (330). For example, the beam-shaping assembly (350) may be disposed over the therapeutic radiation source (330). The therapeutic radiation source (330) may comprise a pulse formation structure (334) (e.g., Pulse Forming Line (PFL), accelerator waveguide) and a target (340) (e.g., X-ray converter, target diode). The PFL (334) may be configured to accelerate pulsed electrons. The target (340) may be configured to convert a high-energy pulse or a pulse of accelerated particles into an X-ray pulse. The target (340) may be composed of a material that emits high-energy photons such as gamma rays or X-rays when impinged upon by high-energy particles/pulses. In some variations, the target (340) may comprise one or more of a self-magnetic pinch (SMP) diode and a rod-pinch (RP) diode.

In some variations, the therapeutic radiation source (330) may comprise a PFL (334) configured to generate a high-energy pulse and/or a pulse of accelerated particles (e.g., a pulse of accelerated electrons) from a high-power source (320) (e.g., Marx generator) having predetermined pulse parameters (e.g., pulse width or duration, rise time, fall time, etc.). In some variations, the PFL (334) may be configured to output a high-voltage pulse having a pulse width of about 50 ns.

Figure 3B:
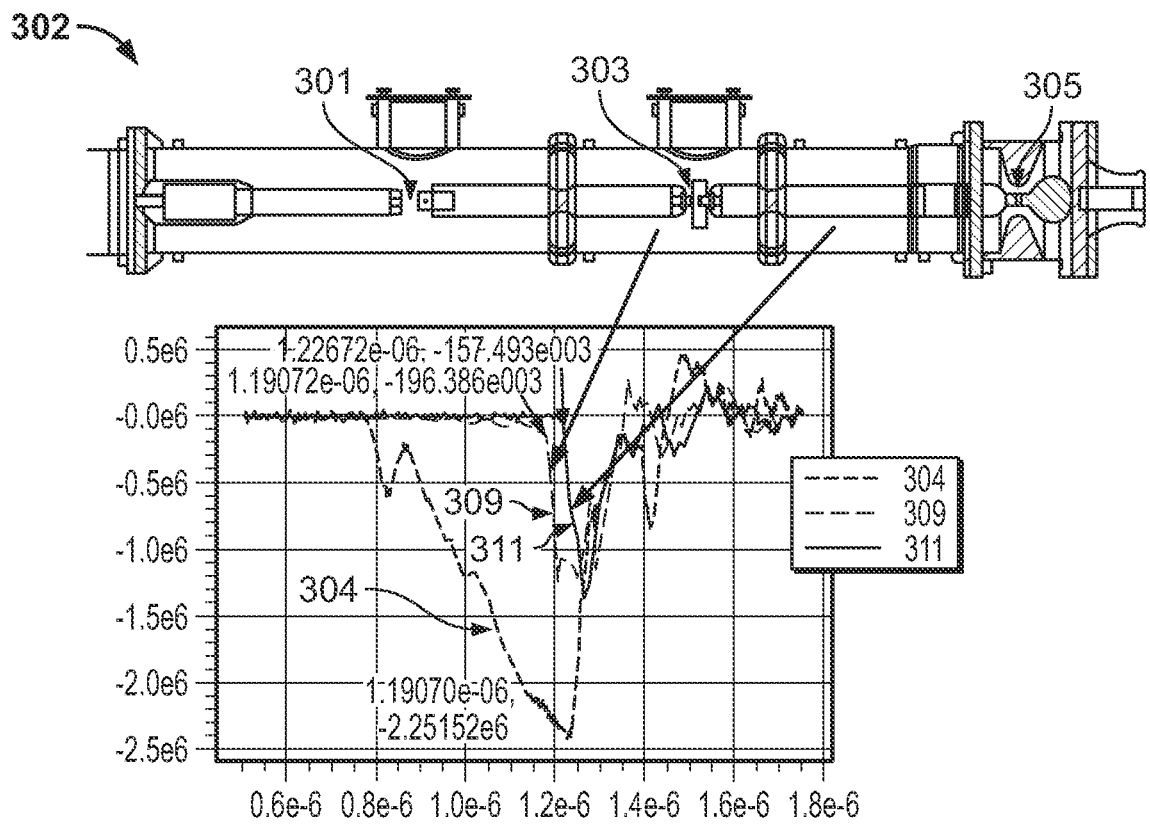
FIG. 3B depicts one variation of a multi-section pulse-formation line (PFL) and corresponding voltage waveforms at various points/nodes along the PFL.
Figure 3C:
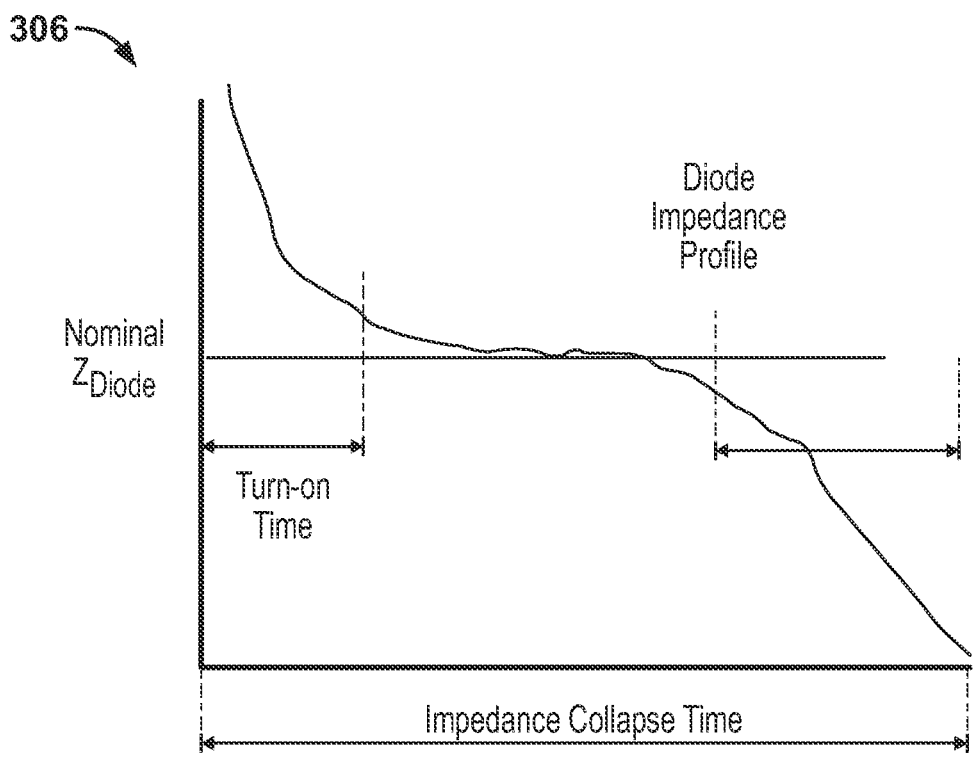
FIG. 3C depicts an exemplary impedance profile of a target (e.g., X-ray converter, target diode).

In some variations, impedance collapse of the target (340) may occur when the diode shorts out. For example, a collapse velocity may be about 1 cm/μs. In some variations, impedance collapse may be based on a diode AK gap such that only a single X-ray pulse may be produced even if a discharging PFL (334) has multiple pulse reflections appearing at the diode (340). FIG. 3C is an exemplary impedance profile (306) of a target (340) where a turn-on occurs after voltage application and the impedance falls to its nominal level and remains nearly flat. This is followed by the complete shorting of the AK gap at which time the impedance collapse is complete. In some variations, a diode (340) may have an impedance of between about 25 ohms and about 100 ohms. The impedance in FIG. 3C is about 100 ohms. In some variations, the peak diode voltage may be about 3 MV and the diode current may be between about 30 kA to about 100 kA.

The therapeutic radiation source (330) may be configured to emit a radiation beam, and may be positioned on the gantry such that a radiation beam central axis (332) crosses a system isocenter (390). A detector (380) may be mounted on the gantry (310) opposite to the therapeutic radiation source (330). The detector (380) may be provided to detect the collimated, high energy radiation of each radiation beam. The detector (380) provided for the therapeutic radiation source (330) is optional but may improve one or more of imaging, system quality assurance, and real-time quality assurance performed by the system (300). A high-power source (320) may be coupled to the therapeutic radiation source (330) via a connector (322) as described in more detail herein.

The system (300) may further comprise any of the imaging systems described herein (not shown in FIG. 3) mounted on the gantry (310) and an imaging detector (not shown) mounted on the gantry (310) opposite to the imaging system. The imaging system may be configured to generate an imaging beam having a field-of-view defining an imaging central axis. The path of the imaging beam may generate one or more imaging planes used to generate imaging data for use with treatment planning. In some variations, the system isocenter (390) may be defined as the intersection of a central longitudinal axis (e.g., extending out of the page in FIG. 3A) of the bore (312) and the imaging central axis of the imaging field-of-view (not shown in FIG. 3A for the sake of simplicity). For example, the radiation beam central axis (332) and an imaging beam (not shown in FIG. 3A) may be configured to intersect at the system isocenter (390). In some variations, the patient (360) may be positioned on a patient platform (370) such that the patient target region (e.g., lesion) is located in the treatment plane and/or is collocated (e.g., overlapping) with the system isocenter (390). A lesion of the patient (360) may be positioned within the imaging plane and/or at system isocenter (390).

In some variations, the power source (320) may comprise an intermediate store (IS) capacitor and a water cable (e.g., water dielectric capacitor) configured to charge to a predetermined voltage for discharge to the PFL (334). A short discharge path from the IS (320) to the PFL (334) via the connector (322) reduces inductance and results in a shorter charge time of the PFL (334). For example, stress times may be reduced between about 30% and about 40% relative to direct Marx generator charge times, resulting in breakdown fields increasing by about 50%. Consequently, certain dimensions of the PFL (334) may be reduced by up to about 33%. A PFL (334) configured for short charge times due to coupling with either a very low inductance Marx generator or an IS may have smaller dimensions with lower inductance of the discharge path to the target (340) resulting in faster X-ray pulse rise times. For example, FIG. 3B depicts a multi-section PFL (302) having an associated voltage waveform showing pulse compression after each stage of switching. Waveform (304) depicts the pulse output from the high-power source (e.g., Marx generator), while waveform (309) depicts the pulse after a first switch stage (e.g., output switch) and waveform (311) depicts the pulse after a second switch stage (e.g., peaking switch). In some variations, the series switching elements of the multi-section PFL (302) may generate an X-ray pulse with improved pulse shape characteristics (e.g., rise time, fall time, flat top ripple, low pre-pulse). For example, the PFL (302) may comprise an output switch (301), and/or a peaking switch (303), and/or a prebase switch (305). In some variations, the therapeutic radiation source (330) may comprise a single conductor PFL without a peaking switch or pre-pulse switch.

In some variations, a high-power source (320) and connector (322) may comprise one or more insulators including one or more of water, oil, and gas. For example, a pulse forming line may comprise water, and the pulsed feeds and direct current (DC) charged components may comprise oil. The high-power source (320) may comprise a switch comprising sulfur hexafluoride ($SF_6$) gas.

In some variations, one or more of the high-power source (320), connector (322), therapeutic radiation source (330), and target (340) may comprise respective shielding. For example, the target (340) may comprise electromagnetic shielding facing the high-power source (320) and/or PFL (334) to protect against a fault event such as a breakdown or side strike upstream of the target (340). In some variations, any high-voltage pulsed components of the system (300) may comprise electromagnetic shielding. Examples of electromagnetic shielding may comprise X-ray shielding. In some variations, high-voltage switches (such as those used in high-power source (320)) may comprise $SF_6$ gas, in order to reduce the audible switching noise and increase switch reliability. In some variations, the high-voltage switches may comprise a laser trigger configured to generate 30 mJ at a wavelength of about 266 nm.

Mistimed emission (e.g., misfire, pre-fire) of a high dose radiation beam may unintentionally harm the patient, and may be a particular concern with a pulse power radiation source that generates a limited number of high dose pulses. For example, pre-fires may deliver a pulse having a lower than intended voltage. In some variations, any of the radiotherapy systems described herein may comprise a beam emitter configured to control a timing of radiation beam emission to prevent early energy discharge and delayed energy discharge. For example, the beam emitter may comprise a swing-arm configured to retract away from a beam-shaping assembly immediately before emission in order to prevent pre-fires. In some variations, a set of high-voltage switches of a radiotherapy system may be configured to reduce the risk of pre-fire. For example, a high-voltage switch may comprise $SF_6$ gas and a laser trigger configured to operate at less than about 30% of a self-break voltage. The risk of mistimed emission may be further reduced by minimizing the voltage on components and reducing the number of DC charged switching elements in the system.

In some variations, the therapeutic radiation source (330) may comprise one or more of an inductive voltage adder (IVA), Marx generator, capacitor bank and transformer, and PFN Marx (Type E) generator each capable of generating sufficiently high dose rate radiation to deliver a prescribed dose to a patient. For example, an IVA may be configured to generate a multi-megavolt, high current, short duration (e.g., less than 200 nanoseconds), electron beam of up to hundreds of Grays/pulse. A Marx generator may be configured to charge a water cable (e.g., waterline, water dielectric capacitor) configured to directly discharge into the target (340). A capacitor bank and a step-up transformer may be configured to charge the water cable that directly discharges a target. A PFN Marx (Type E) generator may be configured to directly drive the target.

In some variations, a radiotherapy system may comprise a plurality of fixed (e.g., non-rotating) therapeutic radiation sources and a real-time PET imaging system. For example, the system may comprise between two and about eight fixed therapeutic radiation sources. In some variations, each therapeutic radiation source may be configured to emit single radiation beams having a peak X-ray pulse energy of about 3 MeV with a pulse width in the tens of nanoseconds (e.g., between about 40 ns and about 50 ns), and a dose of up to about 60 Gy. The radiotherapy system may further comprise a high-power source configured to generate between about 1 MV and about 9 MV. For example, a system may generate X-ray energy of about 6 MeV with a radiation beam current of about 280 mA and a pulse width of about 3 µs. In some variations, source jitter (i.e., the standard deviation of the arrival time) of the X-ray output pulse may be about 1 µs relative to patient movement.

In some variations, a pulsed power therapeutic radiation source may comprise a temperature management system configured to dissipate excess heat. A temperature management system may comprise heat exchangers, fans, liquid coolant circulation conduits, and/or ducting. Heated air and/or liquids may be transferred to a facility air flow and/or liquid-cooling system that receives the heat from the air and/or liquids and moves it to a facility centralized cooling reservoir. Cooled air and/or fluid may be transported back to the treatment bunker and circulated in thermal contact with heated air and/or fluid from the pulse power therapeutic radiation source.

Inductive Voltage Adder

Figure 4A:
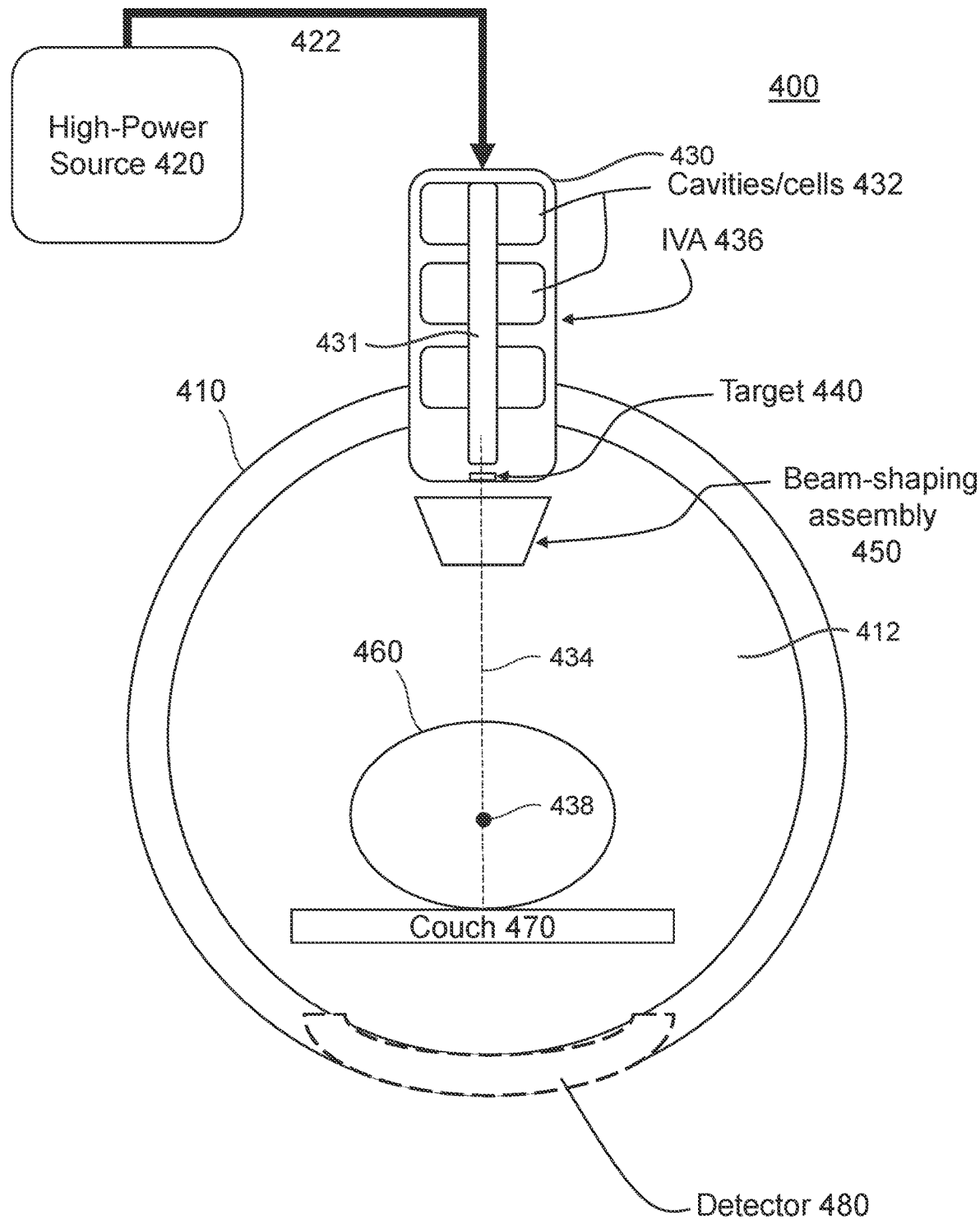
FIG. 4A depicts a schematic representation of a system for flash radiotherapy.

In some variations, a therapeutic radiation source may comprise an IVA configured to generate MV pulsed electron beam energy for conversion by an X-ray converter target into an X-ray beam. An IVA may generate lower component voltages relative to other high-power therapeutic radiation sources and may have compact dimensions suitable for mounting on a gantry. The X-ray beam may be collimated, shaped, and aligned by a beam-shaping assembly for flash radiotherapy treatment. FIG. 4A depicts schematic cross-sectional front view of one variation of a radiation therapy system (400) comprising a gantry (410) and a patient platform (470) (e.g., couch top) configured to hold a patient (460) disposed on top of the patient platform (470). The patient platform (470) may be configured to move within a bore (412) of the gantry (410). The gantry (410) may be a circular gantry (e.g., ring gantry) and comprise a therapeutic radiation source (430) mounted on the gantry (410). The therapeutic radiation source (430) may comprise an induction voltage adder (436) (IVA) and a target (440) (e.g., X-ray converter, target diode). The IVA (436) may be configured to accelerate pulsed electrodes. The target (440) may be configured to convert a high-energy pulse or a pulse of accelerated particles into an X-ray pulse. The target (440) may be composed of a material that emits high-energy photons such as gamma rays or X-rays when impinged upon by high-energy particles/pulses (e.g., any of the heavy metals described above). In some variations, the target (440) may comprise one or more of a self-magnetic pinch (SMP) diode and a rod-pinch (RP) diode.

A beam-shaping assembly (450) may be coupled to the therapeutic radiation source (430). For example, the beam-shaping assembly (450) may be a multi-leaf collimator disposed over the therapeutic radiation source (430) and in the path of the X-ray beam pulse. For example, the multi-leaf collimator may be a dynamic multi-leaf collimator having a plurality of movable leaves.

The IVA (436) may comprise a set of cells (432) each defining a cavity. In some variations, the IVA (436) is configured to generate X-ray beam pulses having an energy of about 1 MV or more, e.g., about 2 MV. The therapeutic radiation source (430) may be configured to emit an electron beam pulse (e.g., radiation beam, X-ray beam pulse) defining a radiation beam axis (434). A detector (480) may be mounted on the gantry (410) opposite to the therapeutic radiation source (430). The detector (480) provided for the therapeutic radiation source (430) is optional but may improve one or more of imaging, system quality assurance, and real-time quality assurance performed by the system (400). A high-power source (420) (e.g., Marx generator) may be coupled to the therapeutic radiation source (430) via a connector (422). The Marx generator (420) may be configured to supply power to the IVA (430). In some variations, an IVA (436) may be configured to generate energy between about 2 MV and about 20 MV with pulse lengths between about tens of nanoseconds and about 100 nanoseconds, and current of up to about 200 kA, e.g., from about 2 MV to about 5 MV, and a current of up to about 100 kA. In some variations, the system (400) may comprise a first therapeutic radiation source and a second therapeutic radiation source.

The system (400) may further comprise any of the imaging systems described herein (not shown in FIG. 4) mounted on the gantry (410) and an imaging detector (not shown) mounted on the gantry (410) opposite to the imaging system. The imaging system may be configured to generate imaging beam having a field-of-view defining an imaging central axis. The path of the imaging beam may generate one or more imaging planes used to generate imaging data for use with treatment planning. In some variations, the system isocenter (438) may be defined as the intersection of a central longitudinal axis (e.g., extending out of the page in FIG. 4A) of the bore (412) and the imaging central axis of the imaging field-of-view (not shown in FIG. 4A for the sake of simplicity). For example, the radiation beam central axis (434) and an imaging beam (not shown in FIG. 4A) may be configured to intersect at the system isocenter (438). In some variations, the patient (460) may be positioned on a patient platform (470) such that a patient target region (e.g., lesion) is located in the treatment plane and/or is collocated (e.g., overlapping) with the system isocenter (438). A lesion of the patient (460) may be positioned within the imaging plane and/or at system isocenter (438).

In some variations, the X-ray beam pulse has a duration of about 200 ns or less. In some variations, the X-ray beam pulse has a duration of about 40 ns to about 50 ns. In some variations, the X-ray beam pulse delivers a dose value from about 1 Gy to about 200 Gy within a single breath hold. In some variations, the dose value is about 60 Gy. In some variations, the X-ray beam pulse has a pulse energy of about 1 MeV or more, e.g., about 3 MeV.

Figure 4B:
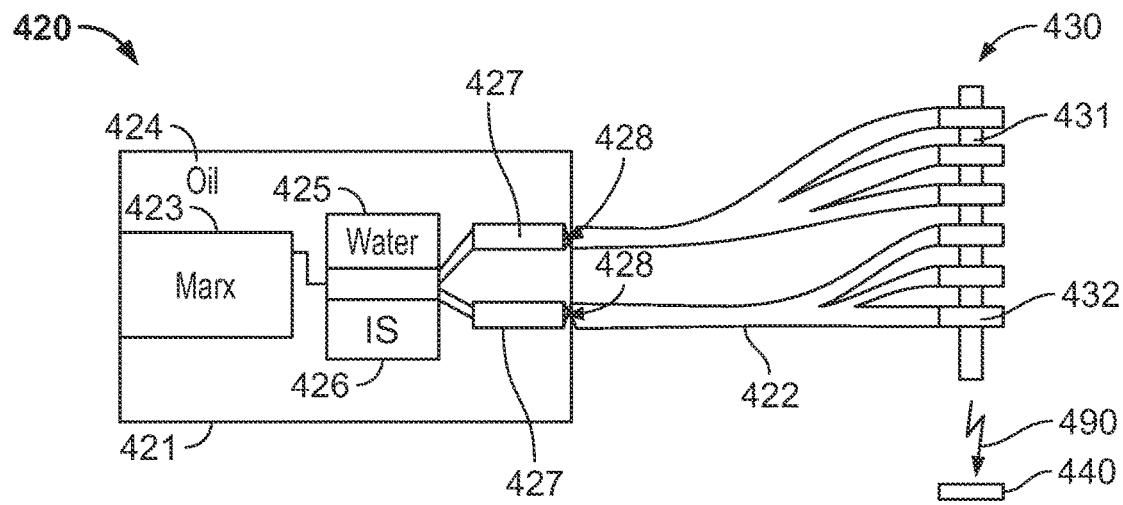
FIG. 4B depicts a schematic block diagram of one variation of a high-power source for a flash radiotherapy system.

FIG. 4B depicts a schematic block diagram of one variation of a high-power source (420) and IVA (430) coupled by a connector (422) (e.g., cables, discharge path). In some variations, the high-power source (420) may comprise a Marx generator (423), water cable (425), IS capacitor (426) (e.g., storage capacitor), and a set of PFLs (427). The Marx generator, water cable, IS capacitor, and PFLs may be enclosed within an enclosure (421) (e.g., tank, housing). The water cable (425) may be disposed between the Marx generator (423) and the IVA (430). The enclosure (421) may be configured to hold oil (424) and may have a volume of about 13 m³. In some variations, the enclosure (421) may have a width of about 6 feet and a length of about 13 feet. The set of PFLs (427) may include, for example, six pulse forming lines. The Marx generator (423) may be configured to charge the IS (426), which in turn is configured to charge the set of PFLs (427). A set of high-voltage switches (428) may be coupled to a corresponding output of the set of PFLs (427). For example, the set of switches (428) may comprise a set of laser-triggered switches as described herein, and in some variations, there may be two sets of switches (as shown in FIG. 4B), where each set of switches may comprise about six switches. In some variations, a controller (not shown) may be in communication with the Marx generator (423) and a plurality of lasers (not shown). Each laser may correspond to a laser-triggered switch (428) of each IVA stage. The controller may be configured to serially activate the lasers to serially close the laser-triggered switches (428) of each stage of the IVA (430).

In some variations, the connector (422) comprises a set of oil-filled coaxial cables disposed between the Marx generator (423) and the IVA (430). For example, the oil-filled coaxial cables may be coupled between the set of PFLs (427) and a respective set of cells (432) of the IVA (430). The set of cells (432) may include, for example, six cells. The IVA (430) may further comprise a metallic transmission line (431) (e.g., stalk, Magnetic Insulated Transmission Line (MITL)) coupled to each of the cells (432) and configured to transmit voltage and current to an AK spacing of an X-ray converter target (440) (e.g., x-ray diode) such that the X-ray converter target (440) is in a beam path of the electron beam pulse (490). When the electron beam pulse strikes the X-ray converter target (440), an X-ray beam pulse is generated. The Magnetic Insulated Transmission Line or MITL current may generate magnetic fields that function to insulate a vacuum region of the target (440) against breakdown. The IVA (430) may advantageously provide voltages upstream of the vacuum transmission line that are a fraction of the target's diode voltage. In some variations, the IVA (430) may be about 2 meters long (e.g., about 7 feet long) and about 0.15 meters wide (e.g., about 24 inches), and each cell (432) may have an outer diameter of about 0.6 meters (e.g., about 6 inches) to accommodate the cores and feeds to a vacuum region. In some variations, the MITL (431) may be tapered to match the cell drive impedance to the MITL (431) and target (440) (e.g., diode). For example, the MITL (431) may be tapered from a first cell's position impedance of about 12 ohms to a sixth cell's position impedance of about 42 ohms. In some variations, the MITL (431) may taper to about 7.5 cm outer diameter at the sixth cell position (closest to the target (440)).

Figure 4C:
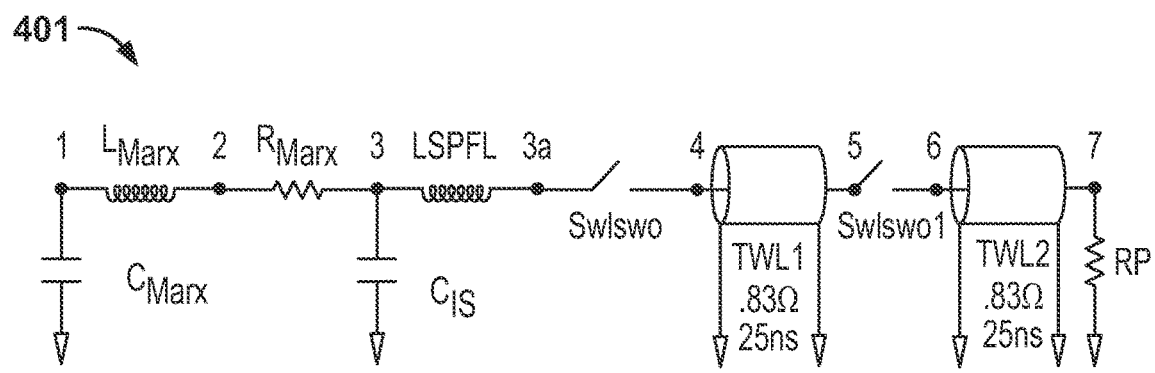
FIG. 4C depicts an equivalent circuit model of a therapeutic radiation source comprising an inductive voltage adder (IVA).
Figure 4E:
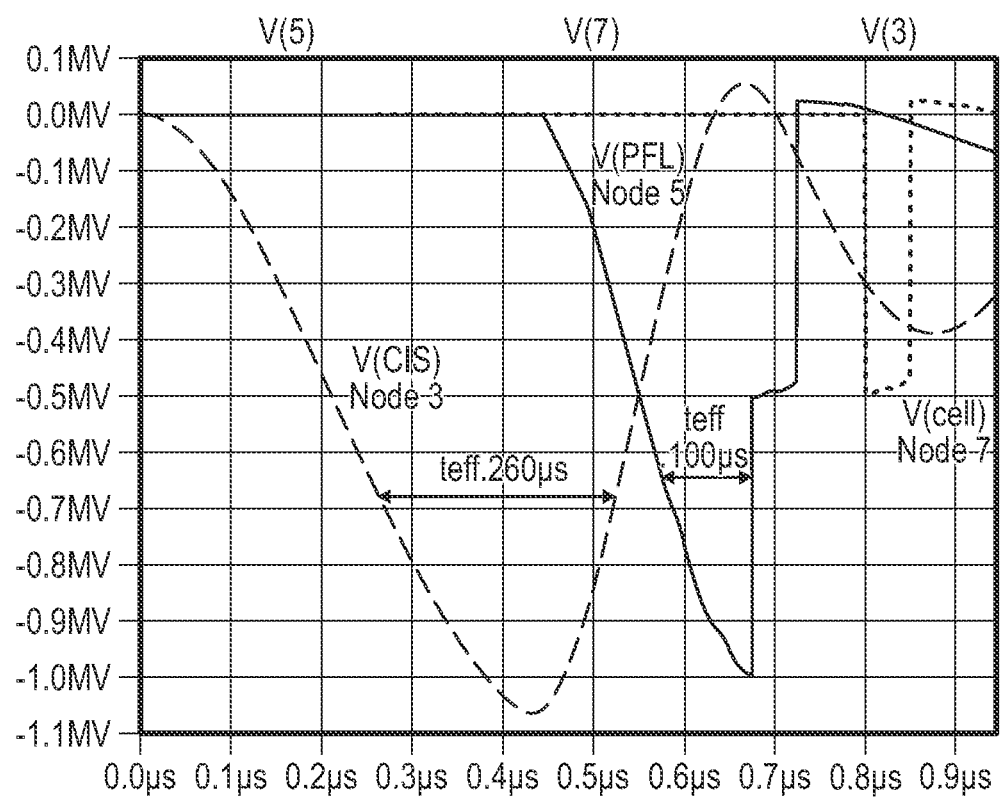
FIG. 4E depicts a PSPICE simulation of the voltage waveforms of an intermediate store (IS) capacitor, PFL, and output voltage delivered to the cells of an IVA.
Figure 4F:
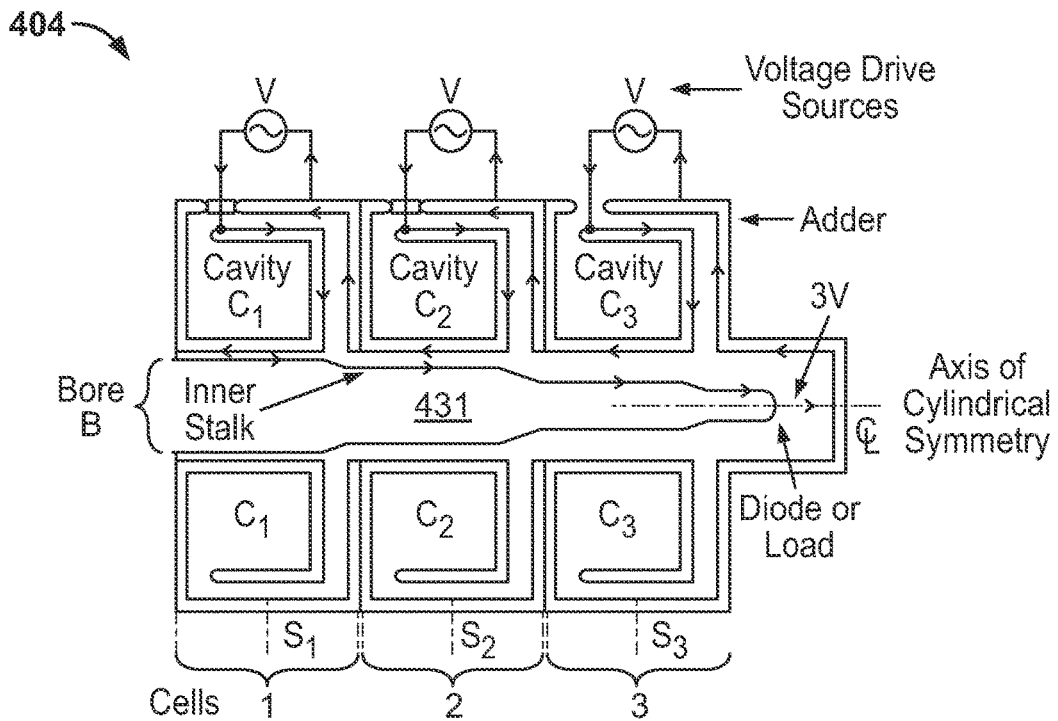
FIG. 4F depicts a schematic circuit block diagram of one variation of a three stage (e.g., three serially-arranged cells) IVA.

FIG. 4F depicts a schematic circuit block diagram of one variation of a three stage (e.g., three serially-arranged cells) IVA (404). In some variations, the IVA (404) may be enclosed by a grounded outer metal cylinder (not shown). The IVA (404) may comprise a set of three annular cells ($C_1$, $C_2$, $C_3$) encircling a bore B and vacuum region comprising a Magnetic Insulated Transmission Line or MITL (431) (e.g., conductive transmission line, stalk). The MITL (431) is coupled to one end of the grounded bore B. When each of the cells ($C_1$, $C_2$, $C_3$) is driven with a pulsed voltage V, the voltage appears across each of the three annular gaps in the bore B and causes a current I to flow into the bore B. These pulsed voltages sum along the MITL (431) resulting in the voltage V being multiplied by N cells and transmitted to the ungrounded end of the MITL (431) and to the target (440) (e.g., diode, load). The voltage N*V is applied to the target (440) and the electrons are accelerated with a current of I. In some variations, each stage of the IVA (404) may comprise a voltage source V, a current loop, and a switch (e.g., laser-triggered switch). In some variations, a Marx generator (not shown in FIG. 4F) may be configured to supply power to each voltage source in the three or more stages of the IVA (404).

In some variations, each of the cells ($C_1$, $C_2$, $C_3$) may comprise a core composed of a ferromagnetic material configured to prevent empty cells ($C_1$, $C_2$, $C_3$) from shorting when pulsed by voltage drive sources V. The core functions more as an energy absorbing resistor than an inductive element. For example, the ferromagnetic material may be sized to prevent saturation during the duration of a driving pulse. With respect to a magnetic flux density to magnetic field strength relationship of the core (e.g., B-H curve), the core may be reset before the application of a voltage pulse such that a AB swing of $2*B_{sat}$ or greater than 3T is possible before saturation is reached. The size of the core area A may be calculated as $A=(V*t)/\Delta B$, where A has units of $m^2$ and V*t has units of volt*seconds of the applied pulse to the cell.

Figure 4G:
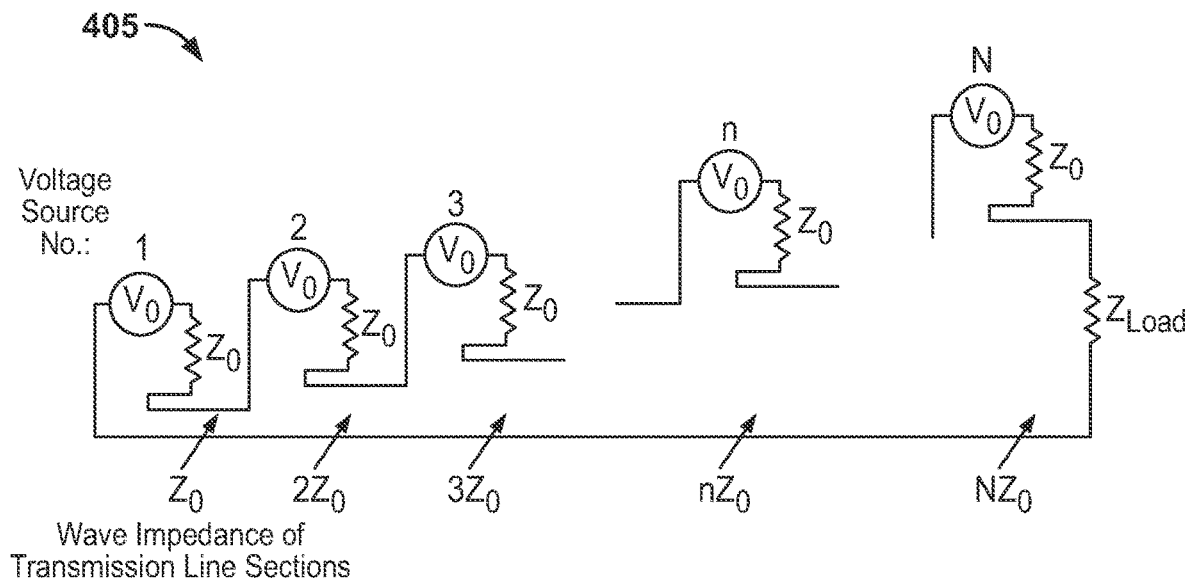
FIG. 4G depicts a schematic circuit block diagram of one variation of a set of impedance matched cells.

FIG. 4G depicts a schematic circuit block diagram of one variation of a set of impedance matched cells (405). In some variations, the drive impedance of each cell may be equal to $Z_{load}/N$ (where N is the number of cells) in order to match the impedance of the drivers to the load. Furthermore, the MITL (e.g., stalk) may be configured to taper where the output end matches the load impedance. In some variations, the stepped impedances of the MITL may be multiplied by a constant m, although this would generate a slight mismatch. In some of these variations, where each cell driver impedance is Zo, as shown in FIG. 4G, an adjacent MITL impedance may be m*n*Zo where n is the $n^{th}$ cell of the N number of cells.

Figure 4H:
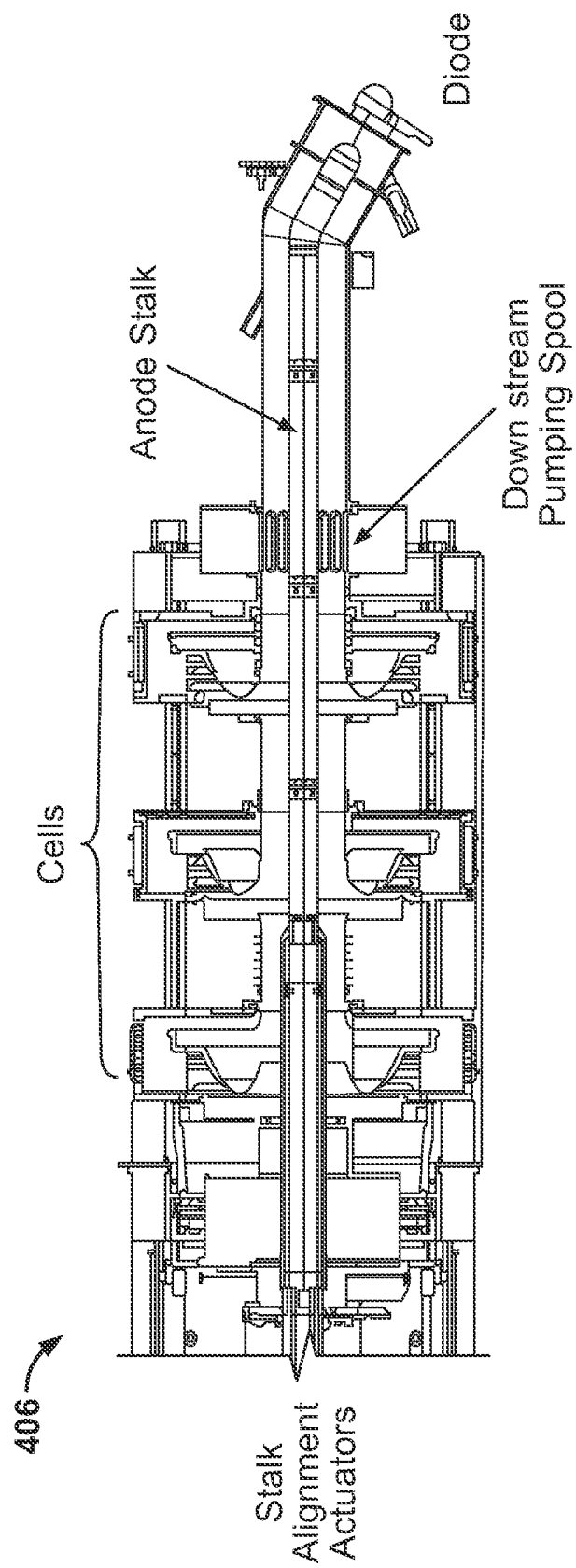
FIG. 4H depicts a schematic representation of one variation of a three-cell IVA.

In some variations, a therapeutic radiation source may comprise an IVA without an IS capacitor. In some of these variations, the radiotherapy system may comprise a low inductance Marx generator (423) directly driving a PFL (430) (see FIG. 4A) through an oil-filled connector (422) (e.g., transmission line). The IVA (430) may comprise a MITL (431) that extends beyond the IVA cells (432) towards a target (440) (e.g., diode). For example, a three-cell IVA (406) as depicted in FIG. 4H may be configured to drive a target (e.g., diode) to a voltage of about 2.25 MV, current of about 60 kA, and a pulse width of about 60 nsec.

FIG. 4C depicts an equivalent circuit model (401) of a therapeutic radiation source comprising an IVA. A PSPICE netlist is depicted in FIG. 4D corresponding to the circuit model of FIG. 4C. In some variations, the IVA corresponding to the circuit model (401) may comprise a ten stage Marx generator, an IS capacitor, six IVA cells, six waterline PFLs, and six gas insulated high-voltage switches. In some variations, a ten stage Marx generator is sufficient to drive each IVA cell to between about 500 kV and about 600 kV. This configuration allows ample space for the IS capacitor to thereby reduce the stress time on the PFL to $\frac{1}{8}^{th}$ of a corresponding system not including an IS capacitor. Thus, the generated electric fields may be twice as large with similar safety thresholds.

In some variations, each IVA cell may be driven by a water cable PFL having a resistance of about 16.7 ohms, which is $\frac{1}{6}^{th}$ the load impedance being driven. The sum total capacity of the six PFLs is represented in the circuit model by a value of about 18 nF. The IS capacitance pulse charging the PFLs is represented by a value of about 35 nF. The IS capacitor comprises a water cable (e.g., water dielectric coaxial capacitor). In some variations, a high-voltage switch comprise a six stage, gas insulated 100 kV switch. Four parallel 200 nF capacitors rated at about 60 kV comprise each half stage. Charged to only 80% of their rating, the expected life may be about $6\times10^5$ pulses. The erected capacitance of this Marx generator may be about 67 nF. In some variations, the ten stage Marx generator with an erected capacitance of about 67 nF may comprise twenty half-stages of about 60 kV rated capacitors, where 1.34 μF per half-stage is required. For example, the Marx generator may comprise seven parallel capacitors each charged to 48 kV or about 80% of its rating. The resulting lifetime may be about $6\times10^4$ shots. The Marx voltage into an open circuit is thus about 960 kV in order to achieve a desired diode voltage.

In some variations, the IS capacitor may comprise a water-filled coaxial capacitor having a capacitance value of about 25 nF. In some variations, the coaxial dimensions may include an outer diameter of about 91 cm, an inner diameter of about 79 cm, and a length of about 84 cm. The IS capacitor may be configured to operate at about 32% of breakdown at 1 MV. The IS capacitor may be configured to charge six parallel PFLs of 5 ohms each. The PFLs may be resonant charged by the IS capacitor with a one-way electrical length of about 25 nsec to about 1 MV. The PFLs may be configured to operate at about 40% of breakdown with coaxial dimensions including an outer diameter of about 15 cm and an inner diameter of about 7.2 cm. In some variations, each IVA cell may be configured to receive a 500 kV having a 50 nsec FWHM pulse through the 5 Ohm transmission lines via laser-triggered switch. The laser trigger timing may be adjusted to compensate for unequal transmission line length to the IVA cells.

FIG. 4E depicts a PSPICE simulation (403) of voltage waveforms of an IS capacitor (dashed line), PFL (solid line), and cell output voltage (dotted line) delivered to the cells of an IVA. For example, each core of each IVA cell may receive a pulse of about 0.03 Volt-secs and may comprise a ferrite core of about 0.1 m$^2$ and/or an annular cross-section of about 10 cm by 10 cm. Each cell may be driven by a current of about 100 kA at a voltage of about 500 kV. In some variations, the IVA may be driven to a voltage of about 3 MV (e.g., 6*500 kV) with the current of any given cell or about 100 kA.

Water Cable

Figure 5A:
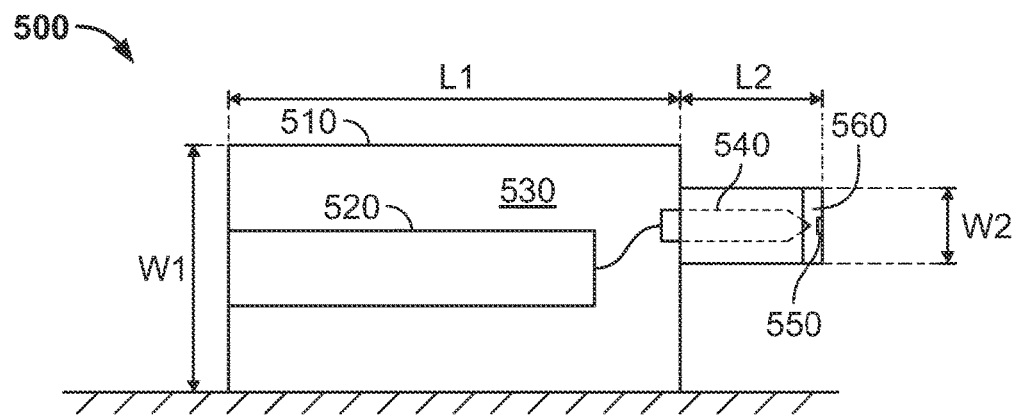
FIG. 5A depicts a block diagram of a high-power source (500) configured to couple to a target (e.g., X-ray converter target).

In some variations, a high-power source may be configured to charge a target for emission of an X-ray beam using an intermediate water line or cable configured as a PFL. The lack of an IVA may reduce the number of components in the radiotherapy system. FIG. 5A depicts a schematic circuit block diagram of one variation of a high-power source (500) configured to couple to a target (550) (e.g., X-ray converter target) without an IVA. In some variations, the high-power source (500) may comprise a Marx generator (520) enclosed within an enclosure (510) (e.g., tank, housing) and a water cable (540) (e.g., waterline). For example, the enclosure (510) may be configured to hold oil (530) and may have a volume of about 13 m$^3$. In some variations, the enclosure (510) may have a width W1 of about 6.5 feet (e.g., from about 5 feet to about 15 feet, about 10 feet) and a length L1 of about 12.5 feet (e.g., from about 7 feet to about 17 feet, about 8 feet). The Marx generator (520) may be configured to resonantly charge the water cable (540), which in turn is configured to charge the target (550). The water cable (540) may be coupled to a target (550) (e.g., diode) comprising a vacuum enclosure (560). For example, a diode or target element may be disposed within the vacuum enclosure (560). The water cable (540) and vacuum enclosure (560) may together have a length L2 of about 4 feet (e.g., about 1.5 feet to about 5 feet, about 3 feet). The vacuum enclosure (560) may have a width W2 of about 2.5 feet, for example. A high-voltage switch or set of switches (not shown) may be coupled to the water cable (540) and configured to discharge energy directly to the target (550). For example, the switch may comprise a single or a set of 3 MV gas insulated, laser triggered switches as described herein.

In some variations, a capacitance of the Marx generator (520) may be configured to be sufficiently greater than a capacitance of the water cable (540) so as to generate about a 1.5 times voltage gain of the water cable relative to the Marx generator voltage. For example, the high-power source may comprise a thirty stage, 2.5 MV Marx generator with four 50 kV parallel capacitors per half stage. In some variations, the Marx generator may have a length of about 2.9 m, a width of about 0.75 m, and a height of about 0.6 m. In some variations, the enclosure (510) may have a length of about 3.6 m, a width of about 2 m, and a height of about 1.8 m. In some variations, the water cable (540) may have a length of about 0.9 m and a diameter of about 0.6 m. The target (550) may have a length of about 0.3 ft.

Figure 5B:
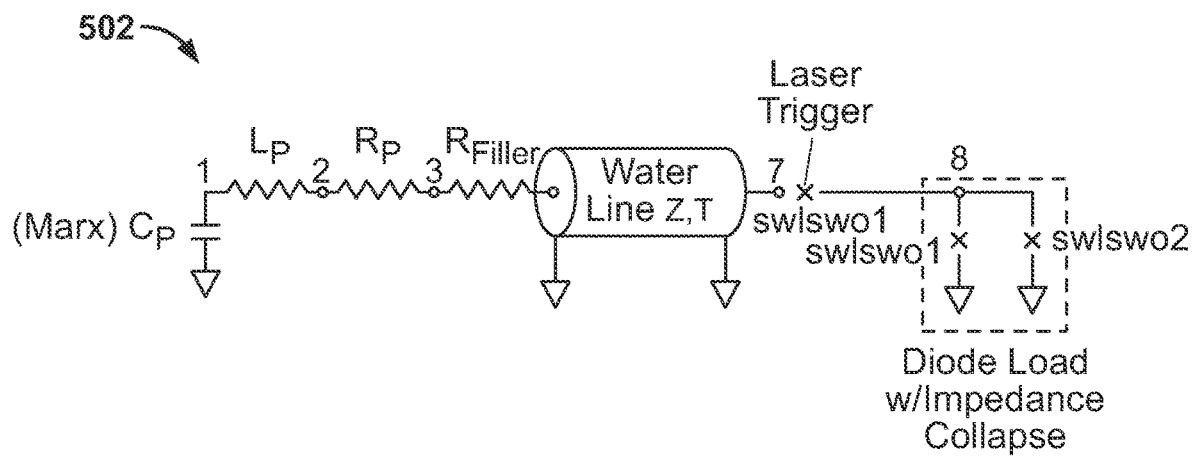
FIG. 5B depicts an equivalent circuit model of a high-power source and water cable (e.g., waterline, water dielectric).
Figure 5D:
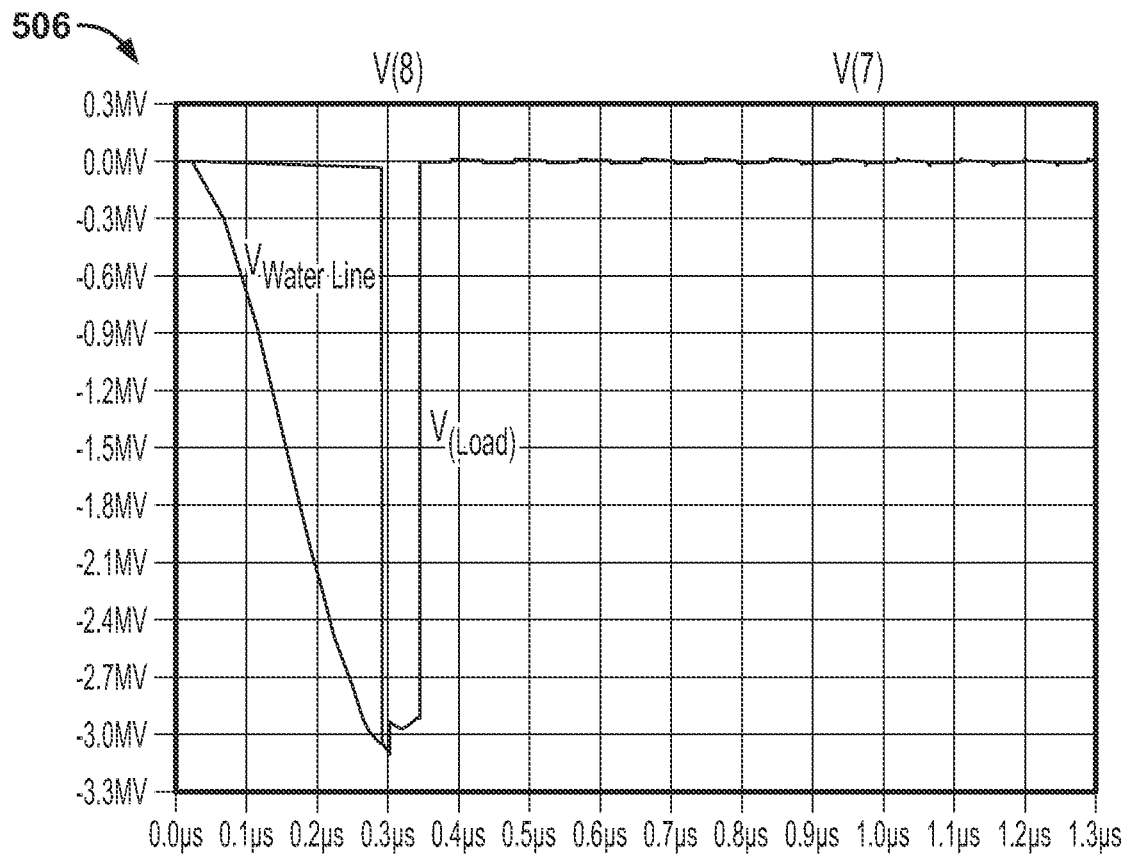
FIG. 5D depicts a PSPICE simulation of voltage waveforms of the water cable and output voltage delivered to the target (e.g., diode).
Figure 5E:
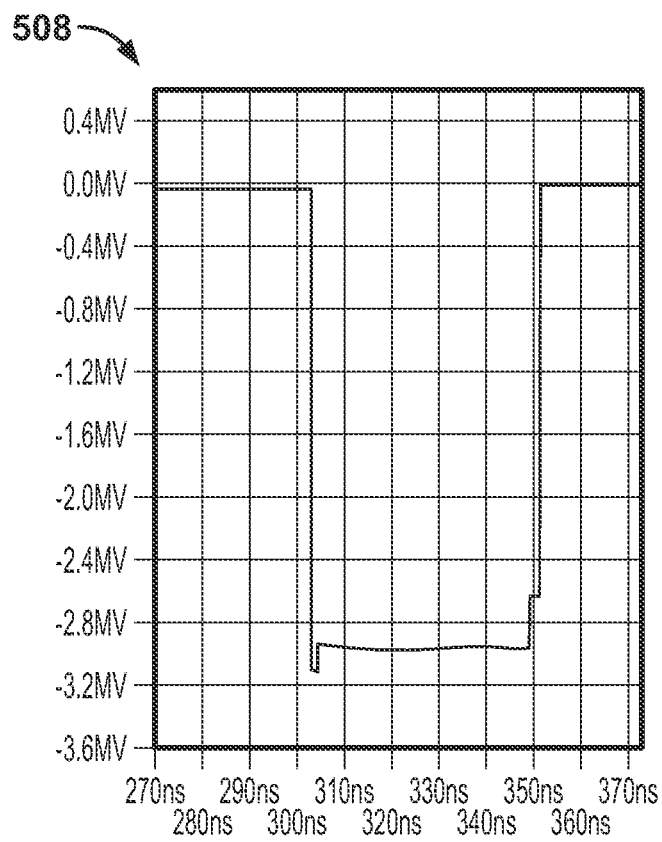
FIG. 5E depicts another PSPICE simulation of a voltage waveform of the output voltage to the target.

FIG. 5B depicts an equivalent circuit model (502) of a high-power source and water cable (e.g., waterline, water dielectric), and FIG. 5C depicts the corresponding PSPICE netlist for simulation. FIG. 5D depicts a PSPICE simulation (506) of voltage waveforms of the water cable and output voltage delivered to the target (e.g., diode). FIG. 5E depicts another PSPICE simulation (508) of a voltage waveform of the output voltage to the target. The target is modeled to have the impedance collapse as described herein. In some variations, the voltage at the diode may be increased to compensate for circuit losses. For example, the target voltage may be raised with a corresponding reduction in diode impedance or increase in pulse length.

In some variations, a thirty stage Marx generator with a nominal erected capacitance of about 14.6 nF may comprise sixty capacitive half-stages charged to a maximum of about 41.5 kV or 83% of each capacitor's 50 kV voltage rating. The voltage output may be into an open circuit of about 2.5 MV. In some variations, a set of four parallel 220 nF, 50 kV rated capacitors may each comprise a half stage and provide a capacitance of about 880 nF or 14.6 nF for the fully erected Marx capacitance. Operating at only about 41.5 kV charge voltage per capacitor may extend the life of the capacitors by about 4.4 times their ratings, equating to a predicted capacitor life of about $4.4 \times 10^5$ shots. A Marx generator of this class may have a stray capacitance of about 130 nH per stage. In some variations, the impedance of the water cable may be about 6 ohms with a one-way electrical length of about 22.5 nsec. In some of these variations, a square 3 MV, 45 nsec pulse may be applied to the target. Additionally, the system disclosed in FIG. 5A may comprise an IS capacitor which may allow the system to be reduced in size.

Capacitor Bank and Transformer

Figure 6A:
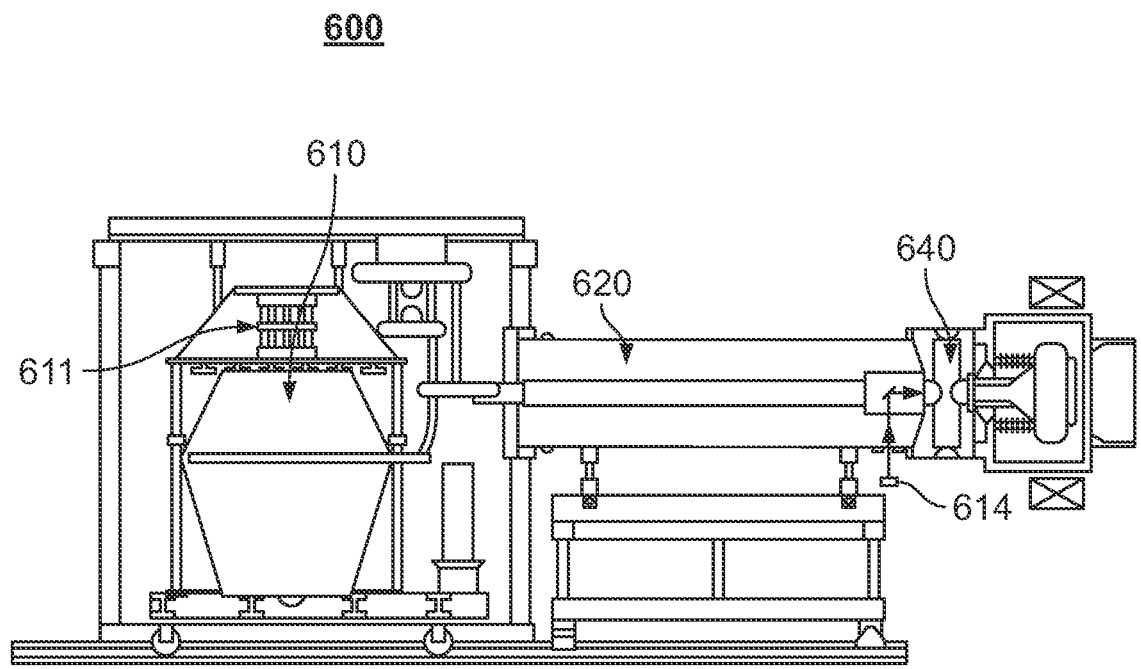
FIG. 6A depicts a schematic partial cutaway side view of one variation of a flash radiotherapy system.
Figure 6B:
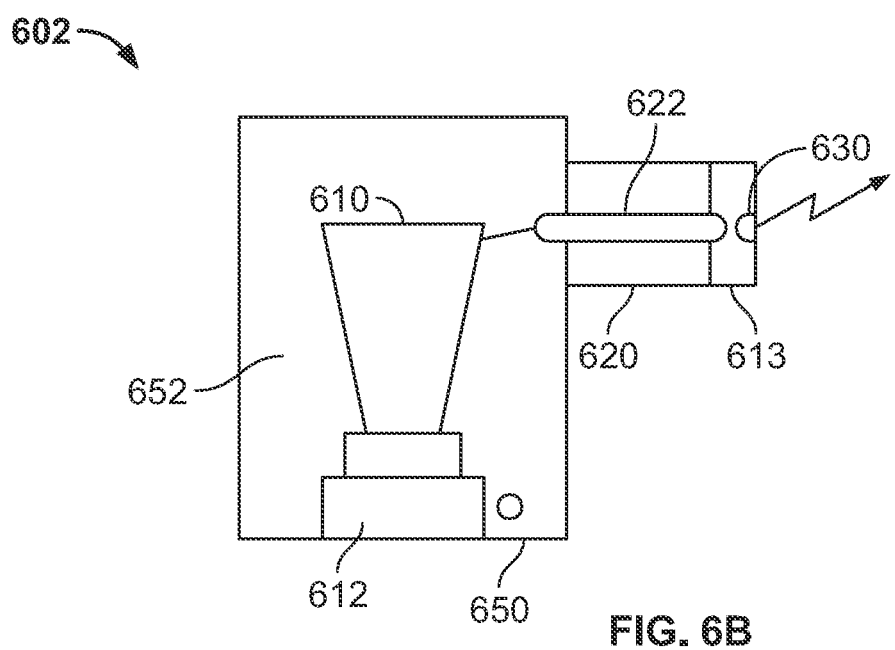
FIG. 6B depicts a schematic side view of one variation of a flash radiotherapy system.

In some variations, a therapeutic radiation source may comprise a capacitor bank with a step-up transformer configured to charge a water cable pulse forming line for conversion by a target into an X-ray beam. Such a system may provide pulsed power for radiotherapy with relatively fewer parts (e.g., fewer switching elements) that may improve reliability. FIG. 6A depicts a schematic cross-sectional view of one variation of a radiotherapy system (600) comprising a transformer (610), PFL (620), and laser-triggered switch (640) that may be activated by a trigger laser (614). The radiotherapy system (600) may also comprise a first switch (611) that is connected to the transformer (610), where the first switch (611) may be a prime switch that is air-insulated. FIG. 6B depicts a schematic cross-sectional view of another variation of a radiotherapy system (602) comprising a transformer (610), capacitor bank (612), PFL (620) comprising a water cable (622) (e.g., water dielectric capacitor), and an X-ray converter target (630) (e.g., diode), which may be within a vacuum enclosure (613). The dimensions of the PFL (620) may be from about 3 feet to about 4 feet. For example, the water cable (622) may have a length of about 3 feet, and the vacuum enclosure (613) may have a length of about 1 foot. The transformer (610) and capacitor bank (612) may be enclosed within an enclosure (650) (e.g., tank, housing). For example, the enclosure (650) may be configured to hold oil (652). The dimensions of the enclosure (650) may be similar to the dimensions of any of the previously-described enclosures (e.g., having the same or similar width and length). In some variations, a high-voltage switch (not shown in FIG. 6B) may be coupled to an output of the PFL (620). For example, the high-voltage switch may comprise a laser-triggered switch as described herein comprising $SF_6$ gas.

FIG. 6C is an equivalent circuit diagram of one variation of a high-dose therapeutic radiation source (604) comprising a transformer and capacitor bank and laser-triggered gas switch, and FIG. 6D is the corresponding PSPICE simulation netlist (606).

In some variations, the transformer (610) may be a repetitive pulse voltage step-up transformer having an output greater than 1.5 MV (e.g., about 3 MV). In some variations, the enclosure (650) may have a length of about 2.4 m, a width of about 2.4 m, and a height of about 3 m to hold the transformer (610) in oil (652). In some variations, the PFL (620) may have a length of about 0.9 m and a diameter of about 0.6 m. In some variations, the target (630) may have a length of about 0.3 m and a diameter of about 0.6 m. In some variations, the capacitor bank (612) may comprise a set of 100 kV metal can capacitors. For example, a set of four capacitors may be configured in a series array of two rows of two parallel capacitors where each capacitor may have a capacitance of about 2.2 µF. In some variations, the capacitor bank (612) may be charged to about ±85 kV such that switching into an open circuit produces about 170 kV. This output may correspond to an operating level of about 85% of rated voltage resulting in a projected capacitor life of about 3.7 times its projected life at a rated voltage of about 100 kV, equating to a predicted capacitor life of about $1\times10^4$ shots. In some variations, the capacitor bank (612) may comprise a 200 kV gas switch configured for a 60 kA peak discharge current. In some variations, the capacitor bank (612) may be configured to discharge into the primary turns of a 1:20 pulse transformer (610). The secondary turns of the transformer (610) may be configured to charge the water cable (622) having an impedance of about 6 ohms and a one-way electrical length of about 22.5 nsec. In some of these variations, a 45 nsec pulse may be applied to the target (630). The target (630) may have an impedance of about 100 ohms. A laser triggered, high-pressure $SF_6$ gas-filled switch may be configured to switch out the water cable (622) at near peak voltage resulting in a 3 MV pulse on a 100 ohm diode with a pulse width of about 45 nsec, as shown in FIGS. 6E and 6F.

Figure 6E:
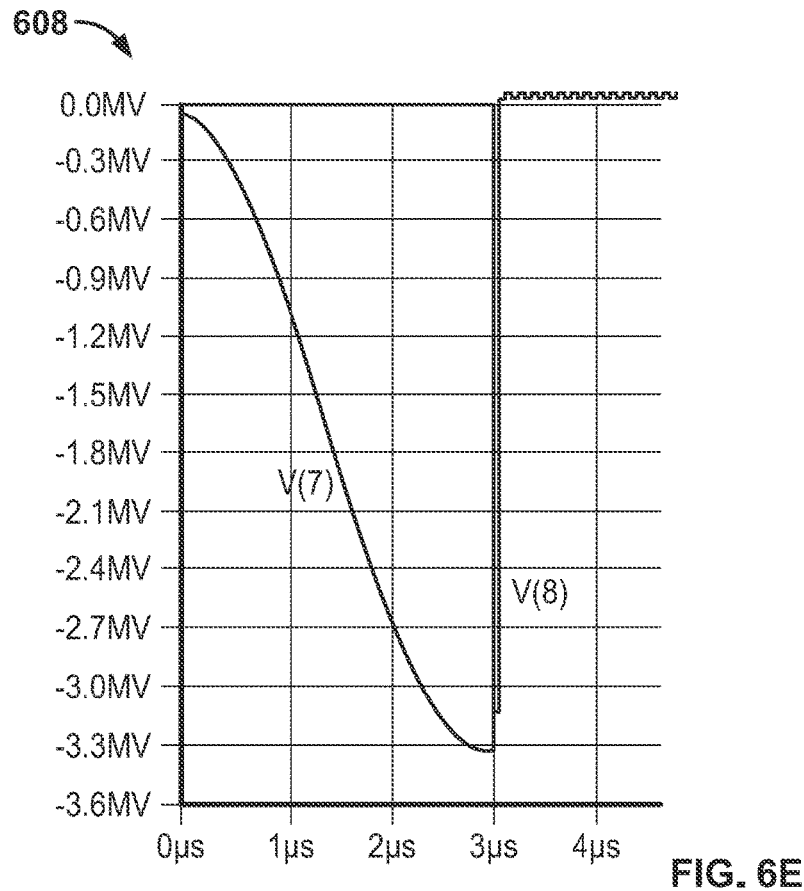
FIG. 6E depicts a PSPICE simulation of voltage waveforms of a pulse charge voltage on a water cable and an output pulse on a target (e.g., X-ray converter target) for a flash radiotherapy system.
Figure 6F:
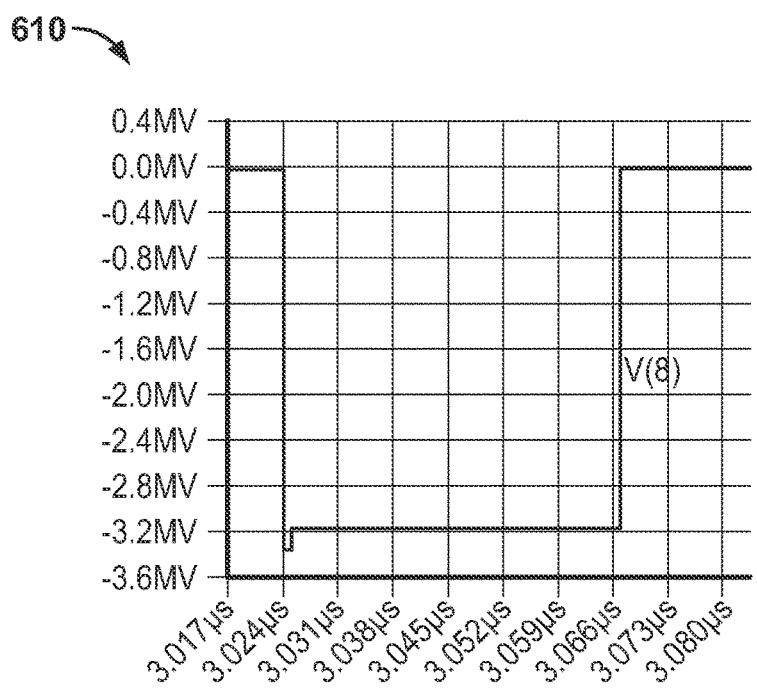
FIG. 6F depicts another PSPICE simulation of a voltage waveform of the output pulse into a target (e.g., X-ray converter target).

FIG. 6E depicts a PSPICE simulation (608) of voltage waveforms of a pulse charge voltage on the water cable (622) and an output pulse on the target (630) (e.g., diode). FIG. 6F depicts another PSPICE simulation (610) of a voltage waveform of the output pulse into the target (630) (e.g., diode). The target is modeled to have the impedance collapse as described herein.

Additionally, or alternatively, an IVA (e.g., six cell IVA) as described with respect to FIGS. 4A-4E may be coupled between the target (630) and PFL (620) of the system (600). This may allow the transformer (610) to output about 1.5 MV, which may allow a reduction in the size of the tank (650).

Pulse Forming Network Marx Generator

In some variations, a therapeutic radiation source may comprise a Pulse Forming Network (PFN) (Type E) Marx generator configured to directly drive an X-ray converter target (e.g., 100 ohm diode) for conversion into an X-ray beam without a water cable or an IVA. For example, a matched impedance PFN Marx generator may drive a 100 ohm diode where the PFN Marx generator may be charged to an open circuit equivalent voltage of about 6 MV. In some variations, the PFN Marx generator may comprise sixty 100 kV stages or one hundred twenty half-stages rated at about 50 kV. For example, each half stage may comprise a six-section type E PFN. Each full stage may have a stray inductance of about 130 nH. In some variations, the PFN Marx generator may be disposed in an enclosure having a length of at least 6 m.

Figure 7A:
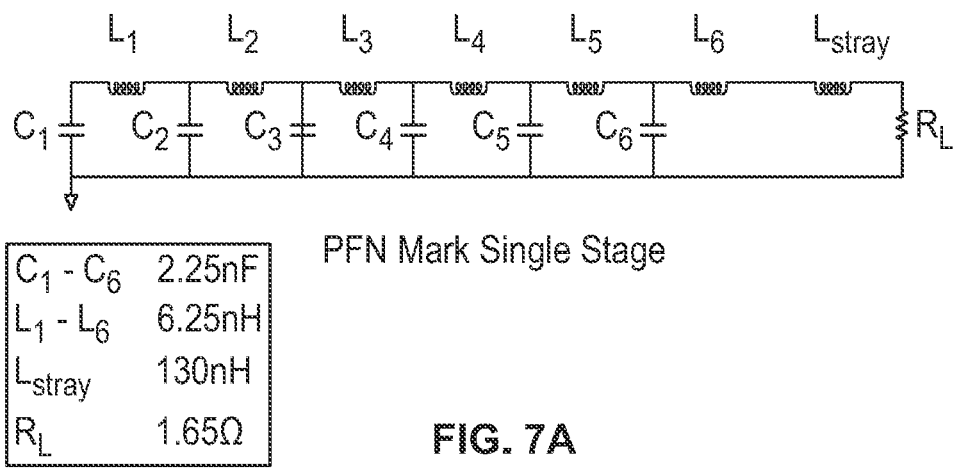
FIG. 7A depicts an equivalent circuit model of a single stage pulse forming network (PFN) Marx generator.

FIG. 7A depicts an equivalent circuit model (700) of a single stage PFN Marx generator. Each stage of the generator may include an impedance of about 1.65 Ohm charged to 6 MV to drive a matched 1.65 Ohm load. For these short pulses, the stray inductance of each stage may dominate the series inductance of the PFN Marx generator having six sections. For example, a 130 nH inductance per stage may be nearly 4 times the total series inductance of the six sections of the PFN Marx generator, and may be more than twenty times greater than the inductance of any given section of the PFN Marx generator. In some variations, the circuit model may comprise multiple LC circuits (each comprising an inductor and a capacitor) and an RLC circuit (comprising a resistor, inductor, and a capacitor). For example, the circuit model (700) may comprise five LC circuits that are serially connected to each other ($L_1C_1$ circuit, $L_2C_2$ circuit, $L_3C_3$ circuit, $L_4C_4$ circuit, $L_5C_5$ circuit) and one RLC circuit, where the inductance may be modeled as $L_6$ and a stray inductance $L_{stray}$, and includes a capacitor $C_6$ and a $R_L$ resistor.

Figure 7B:
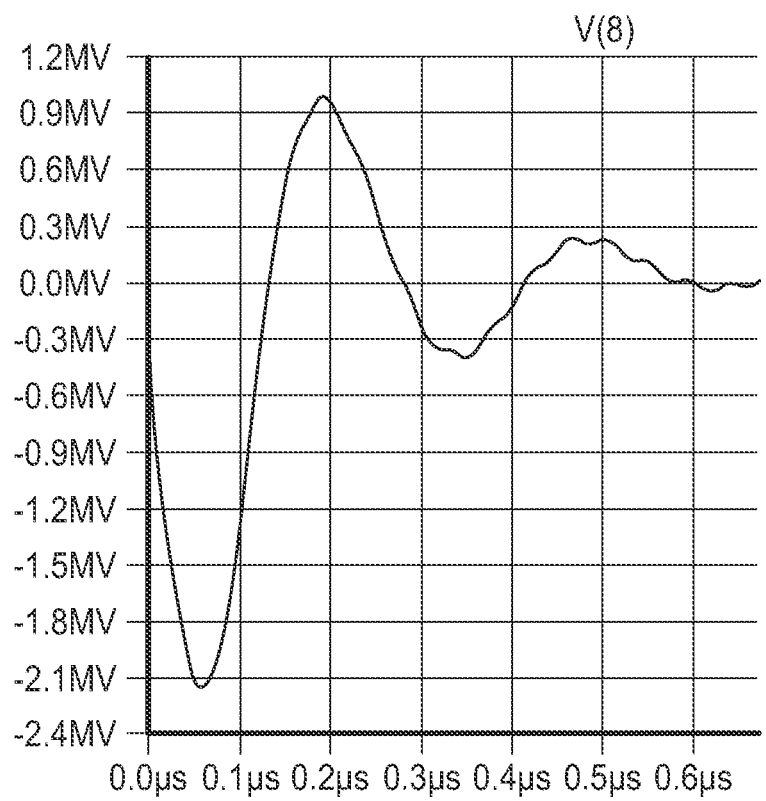
FIG. 7B depicts a PSPICE simulation of voltage waveforms of output voltage delivered to a target (e.g., X-ray converter target).
Figure 7C:
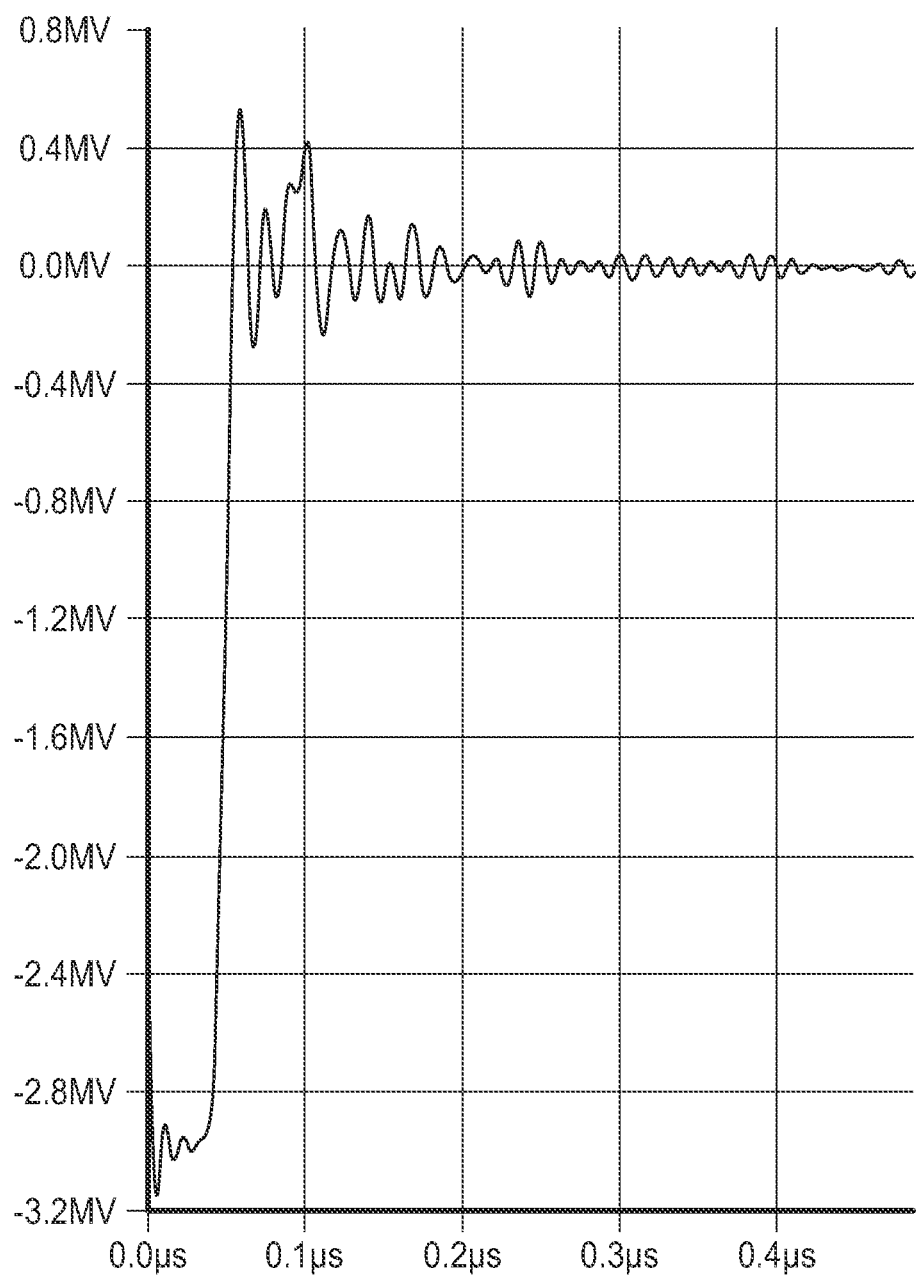
FIG. 7C depicts another PSPICE simulation of voltage waveforms of output voltage delivered to a target (e.g., X-ray converter target).

FIG. 7B depicts a PSPICE simulation (702) of voltage waveforms of output voltage delivered to the target (e.g., diode) based on a realistic model of stage inductance of about 130 nH per stage. FIG. 7C depicts another PSPICE simulation (704) of voltage waveforms of output voltage delivered to the target (e.g., diode) based on an unrealistic model of stage inductance of about 2 nH per stage.

In the circuit models described herein where multiple elements within a pulsed power source are synchronized, timing jitter or variations in arrival times of a trigger pulse is assumed to be zero. Furthermore, the circuit models described herein do not include second order details such as stray capacitance, circuit losses, and circuit parameter values more closely matching physical dimensions dictated by voltage hold-off considerations.

II. Methods

Also described here are methods for rapidly delivering high doses of radiation using the systems and devices described above. In some variations, the methods may be used to deliver a prescribed radiation dose to a desired region of a patient within a predetermined time period (e.g., one breath hold). Generally, the methods described here comprise registering a patient loaded onto a patient platform and treating the patient using a radiotherapy system having a plurality of therapeutic radiation sources emitting radiation beams at predetermined dose rates. The prescribed radiation dose may be delivered within a single breath hold or as fractions across multiple breath holds. For example, a 20 Gy dose may be delivered across 10 breath holds such that 2 Gy is delivered for each breath hold.

One variation of flash dose delivery may comprise a single breath hold where the system or operator instructs the patient to hold their breath, and the patient holds their breath and may optionally use a cue or signal to indicate that they have achieved a stable breath hold. A high-resolution image is acquired and the system reconstructs the image and performs a fusion of the image with a planning image. The operator may manually offset the acquired image to match the planning image, and decides whether the image fusion is within acceptable ranges of error. The system delivers the prescribed dose (e.g., whole dose, dose fraction). The system or operator may instruct the patient to resume breathing, and the patient resumes breathing.

Figure 8:
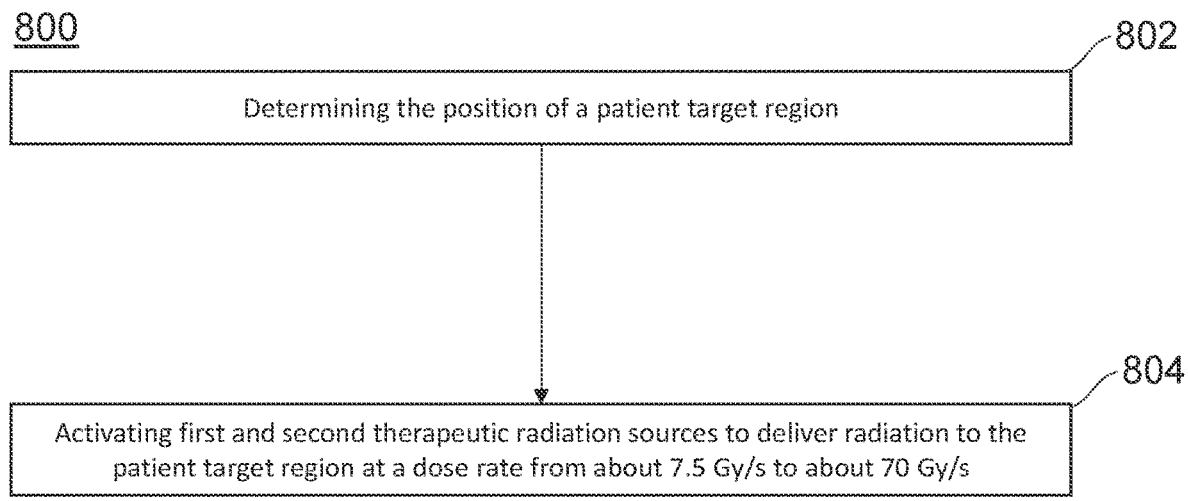
FIG. 8 depicts a flowchart representation of one method for flash radiotherapy.

In some variations, a method of flash dose delivery may comprise registering a patient to a patient platform to detect a position of a patient target region. First and second therapeutic radiation sources are activated to deliver radiation to the patient target region at a flash dose delivery rate. As depicted in FIG. 8, method (800) may comprise determining (802) the position of a patient target region. The position of a patient target region may be confirmed on a patient platform of a radiotherapy system using one or more imaging modalities. For example, the position of the patient target region may be verified just prior to (e.g., seconds) the high dose radiation beam is emitted. In some variations, the radiotherapy system may comprise a support structure (e.g., gantry, arm, robotic arm, C-arm, gimbal) disposed about the patient platform, a first therapeutic radiation source, a second therapeutic radiation source, and an imaging system. The first and second therapeutic radiation sources and the imaging system may be mounted on the support structure, which may be, in some variations, a gantry. The imaging dose/resolution for determining patient positioning may vary to provide different functions during different parts of the procedure. For example, low dose kVCT or PET/CT may be used for patient registration while high dose kVCT or PET/CT may be used for flash dose delivery. Based on the acquired imaging data, one or more beam delivery parameters may be modified including patient positioning and radiation beam parameters. For example, one or more of the pitch, roll, and yaw of the platform and beam parameters (e.g., beam delivery angle) of a beam shaping assembly (e.g., MLC) may be adjusted based on the imaging data.

The method (800) may further comprise activating (804) first and second therapeutic radiation sources to deliver radiation to the patient target region at a dose rate from about 7.5 Gy/s to about 70 Gy/s. In some variations, activating the first and second therapeutic radiation sources comprises generating a single pulse from each radiation source. In some variations, activating the first and second therapeutic radiation sources comprises generating a plurality of pulses from each radiation source over about 10 seconds such that the cumulative dose rate is from about 7.5 Gy/s to about 70 Gy/s. In some variations, activating the first and second therapeutic radiation sources comprises generating a plurality of pulses from each radiation source over about 2 seconds such that the cumulative dose rate is from about 7.5 Gy/s to about 70 Gy/s. In some variation, the method optionally comprises notifying to engage patient participation (e.g., breath hold).

In some variations, another method of flash dose delivery may comprise generating a first indicator to a patient to pause breathing after an inhale, and acquiring imaging data of the patient while breathing is paused. The acquired imaging data may be combined with treatment planning imaging data to calculate a patient position offset. A treatment plan parameter may be adjusted according to the calculated patient position offset. A second indicator may be generated to the patient to pause breathing after an inhale. A radiation pulse may be emitted to the patient in accordance with the adjusted treatment plan parameter while breathing is paused.

Figure 9:
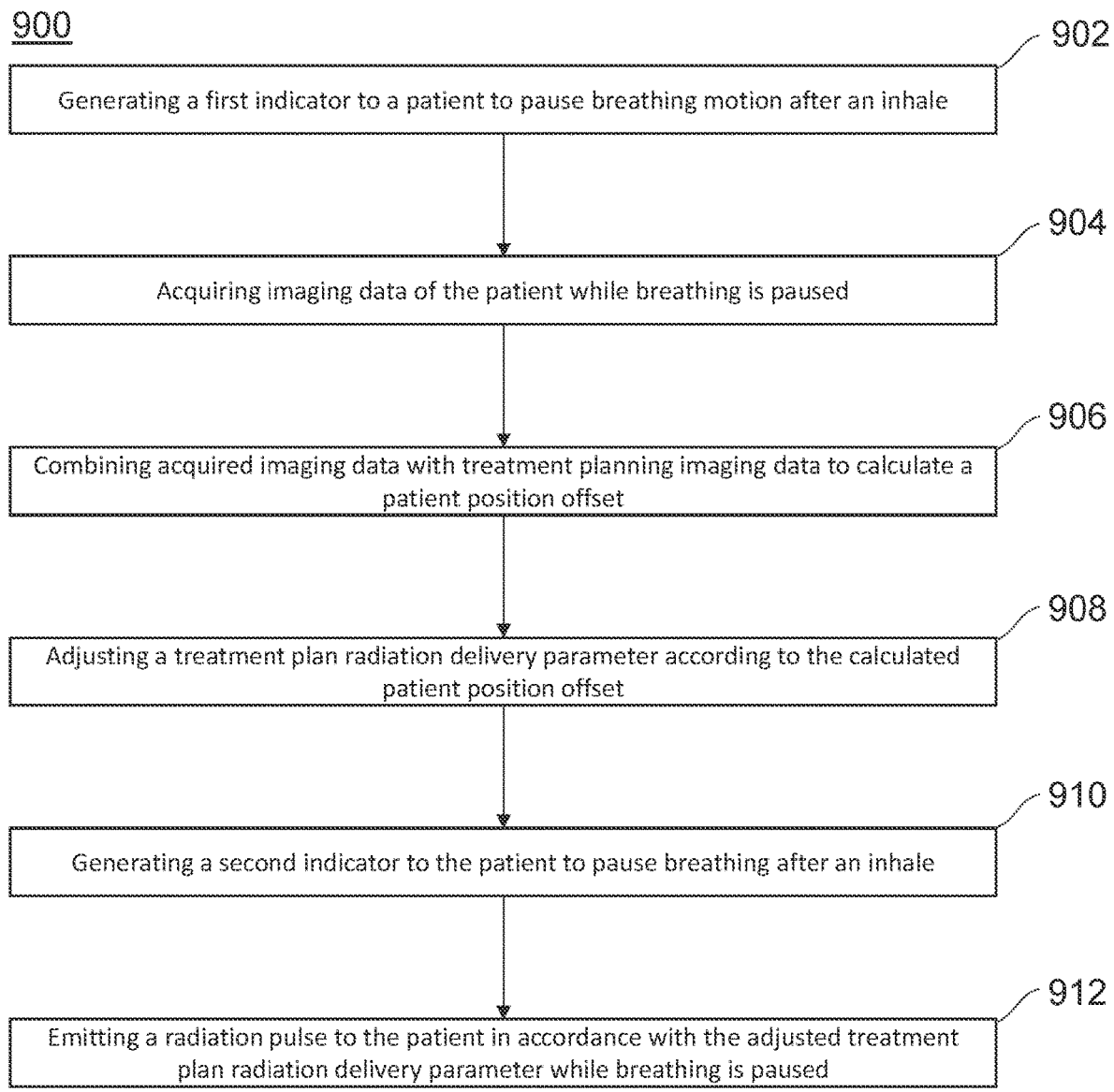
FIG. 9 depicts a flowchart representation of one method for flash radiotherapy.

As depicted in FIG. 9, method (900) may comprise generating (902) a first indicator to a patient to pause breathing after an inhale. The method (900) may further comprise acquiring (904) imaging data of the patient while breathing is paused. The method (900) further comprises combining (906) acquired imaging data with treatment planning imaging data to calculate a patient position offset. The method (900) further comprises adjusting (908) a treatment plan delivery parameter according to the calculated patient position offset. The method (900) may further comprise generating (910) a second indicator to the patient to pause breathing after an inhale. The method (900) may further comprise emitting (912) a radiation pulse to the patient in accordance with the adjusted treatment plan radiation delivery parameter while breathing is paused.

In some variations, the first indicator and the second indicator may comprise one or more indicators selected from the list consisting of a visual indicator, an audio indicator, and a tactile indicator. In some variations, the method (900) may further comprise determining whether the patient position offset exceeds a pre-determined threshold value, and generating a third indicator if the patient position offset exceeds the pre-determined threshold value. In some variations, emitting the radiation pulse comprises emitting radiation from a plurality of therapeutic radiation sources mounted on a gantry disposed around the platform. In some variations, emitting the radiation pulse comprises delivering a dose from about 1 Gy to about 200 Gy in one pulse. In some variations, the emitted radiation pulse has a pulse energy of about 1 MeV or more, e.g., about 3 MeV.

In some variations, a method of flash dose verification (e.g., virtual patient QA) may be performed prior to delivering radiation therapy to a patient. One or more verification cycles may be performed prior to dose delivery in order to iteratively improve the offsets calculated during image fusing. Multiple verification cycles may be needed to align patient, patient treatment region, lesion, organs-at-risk, patient platform, radiation beam, and the like. The operator or system may determine when the calculates offsets are within an acceptable range for dose delivery. For example, the system or operator instructs the patient to hold their breath, and the patient holds their breath. A high-resolution image is acquired, the system indicates that the patient may resume breathing, and the patient resumes breathing. The system reconstructs the image and performs a fusion of the image with a planning image. The operator may manually offset the acquired image to match the planning image, and decides whether the fusion is within acceptable ranges of error. If not, the system again indicates that the patient should hold their breath, and the patient holds their breath. Another high-resolution image is acquired, the system indicates that the patient may resume breathing, and the patient resumes breathing. The system reconstructs the image and performs a fusion of the image with a planning image. The operator may manually offset the acquired image to match the planning image, and the operator decides whether the fusion is within acceptable ranges of error. If so, the system delivers the fraction of the dose and thereafter indicates that the patient may resume breathing, and the patient resumes breathing.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described above, the steps of the methods may not be performed sequentially. Some steps are optional such that every step of the methods may not be performed.

The invention claimed is:

1. A flash radiotherapy system comprising:
   a support structure;
   an imaging system mounted on the support structure;
   a therapeutic radiation source mounted on the support structure, wherein the therapeutic radiation source is powered by a pulsed high-power source and is configured to generate an X-ray beam pulse that delivers radiation at a dose rate from about 7.5 Gy/s to about 70 Gy/s, wherein the high-power source comprises an inductive voltage adder (IVA) that generates an electron beam, and the therapeutic radiation source further comprises an X-ray converter target that converts the electron beam into the X-ray beam pulse, and wherein the high-power source comprises a Marx generator configured to supply power to the IVA and is configured to generate a pulse having an amplitude of about 500 kV and a pulse width (FWHM) of about 50 ns; and a beam-shaping assembly disposed over the therapeutic radiation source and in a path of the X-ray beam pulse.

2. The system of claim 1, wherein the X-ray beam pulse delivers a dose value from about 1 Gy to about 200 Gy.

3. The system of claim 2, wherein the dose value is about 60 Gy.

4. The system of claim 1, wherein the X-ray beam pulse has a duration of about 200 ns or less.

5. The system of claim 4, wherein the X-ray beam pulse duration is about 40 ns to about 50 ns.

6. The system of claim 1, wherein the X-ray beam pulse has a pulse energy of at least about 1 MeV.

7. The system of claim 1, wherein the support structure is rotatable.

8. The system of claim 1, wherein the support structure is stationary.

9. The system of claim 1, wherein the IVA is configured to generate X-ray beam pulses having an energy of about 2 MV.

10. The system of claim 1, further comprising a high-voltage insulant disposed between the Marx generator and the IVA.

11. The system of claim 10, wherein the high-voltage insulant comprises a water cable and/or an oil-filled coaxial cable.

12. The system of claim 1, wherein the IVA comprises an energy storage capacitor or capacitor bank.

13. The system of claim 1, wherein the beam-shaping assembly comprises a dynamic multi-leaf collimator having a plurality of movable leaves.

14. The system of claim 1, wherein the beam-shaping assembly comprises a variable circular collimator.

15. The system of claim 1, wherein the therapeutic radiation source is a first therapeutic radiation source and the system further comprises a second therapeutic radiation source.

16. The system of claim 1, wherein the support structure comprises a gantry.

17. The system of claim 1, wherein the support structure comprises a robotic arm.

18. The system of claim 1, wherein the support structure comprises a gimbal.

19. A flash radiotherapy system comprising:

a support structure;

an imaging system mounted on the support structure;

a therapeutic radiation source mounted on the support structure, wherein the therapeutic radiation source is powered by a pulsed high-power source and is configured to generate an X-ray beam pulse that delivers radiation at a dose rate from about 7.5 Gy/s to about 70 Gy/s, wherein the high-power source comprises an inductive voltage adder (IVA) that generates an electron beam, and the therapeutic radiation source further comprises an X-ray converter target that converts the electron beam into the X-ray beam pulse and wherein the high-power source comprises a plurality of serially-arranged Marx generators that are configured to discharge synchronously to supply power to the IVA; and a beam-shaping assembly disposed over the therapeutic radiation source and in a path of the X-ray beam pulse.

* * * * *